United States Patent
Inoue et al.

(10) Patent No.: US 10,079,350 B2
(45) Date of Patent: *Sep. 18, 2018

(54) ORGANOMETALLIC COMPLEX, COMPOSITION AND LIGHT EMITTING ELEMENT INCLUDING THE ORGANOMETALLIC COMPLEX

(71) Applicant: Semiconductor Energy Laboratory Co., Ltd., Kanagawa-ken (JP)

(72) Inventors: Hideko Inoue, Kanagawa (JP); Satoko Shitagaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,538

(22) Filed: Jul. 25, 2016

(65) Prior Publication Data

US 2016/0336521 A1    Nov. 17, 2016

Related U.S. Application Data

(63) Continuation of application No. 14/688,429, filed on Apr. 16, 2015, now Pat. No. 9,406,895, which is a (Continued)

(30) Foreign Application Priority Data

May 18, 2007   (JP) ................................. 2007-133341

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 6,316,064 B1   11/2001   Onozawa et al.
6,821,645 B2   11/2004   Igarashi et al.
(Continued)

FOREIGN PATENT DOCUMENTS

CN    001517427 A    8/2004
CN    001866576 A    11/2006
(Continued)

OTHER PUBLICATIONS

Machine English translation of Kimura et al. (JP 2002-105055 A).*
(Continued)

*Primary Examiner* — J. L. Yang
(74) *Attorney, Agent, or Firm* — Husch Blackwell LLP

(57) ABSTRACT

To provide a novel organometallic complex, and light emitting elements, light emitting devices, and electronic devices which include the organometallic complex. In addition, to provide a composition in which the organometallic complex is dissolved and to provide a method for manufacturing light emitting elements using the composition. An organometallic complex has high solubility in a solvent. In the organometallic complex, the ligand including a pyrazine skeleton is bound to an atom belonging to Group 9 (Co, Rh, or Ir) or an atom belonging to Group 10 (Ni, Pd, or Pt). In addition, the light emission efficiency is high. Therefore, the organometallic complex is preferably used for manufacturing a light emitting element.

24 Claims, 16 Drawing Sheets

Related U.S. Application Data continuation of application No. 12/120,337, filed on May 14, 2008, now Pat. No. 9,012,036.

(51) Int. Cl.

| | |
|---|---|
| *C07F 15/00* | (2006.01) |
| *H05B 33/14* | (2006.01) |
| *H01L 51/50* | (2006.01) |
| *H01L 51/52* | (2006.01) |
| *H01L 51/56* | (2006.01) |

(52) U.S. Cl.
CPC ...... *H05B 33/14* (2013.01); *C09K 2211/1007* (2013.01); *C09K 2211/1029* (2013.01); *C09K 2211/1044* (2013.01); *C09K 2211/185* (2013.01); *H01L 51/504* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 51/5278* (2013.01); *H01L 51/56* (2013.01); *H01L 2251/301* (2013.01); *H01L 2251/306* (2013.01)

(56) References Cited

U.S. PATENT DOCUMENTS

| | | |
|---|---|---|
| 7,238,437 B2 | 7/2007 | Igarashi et al. |
| 7,265,224 B2 | 9/2007 | Park et al. |
| 7,306,856 B2 | 12/2007 | Igarashi et al. |
| 7,378,162 B2 | 5/2008 | Jeong et al. |
| 7,470,928 B2 | 12/2008 | Jeong et al. |
| 7,951,472 B2 | 5/2011 | Igarashi et al. |
| 7,951,945 B2 | 5/2011 | Igarashi et al. |
| 7,951,946 B2 | 5/2011 | Igarashi et al. |
| 7,951,947 B2 | 5/2011 | Igarashi et al. |
| 7,960,038 B2 | 6/2011 | Ohsawa et al. |
| 7,994,319 B2 | 8/2011 | Igarashi et al. |
| 8,034,935 B2 | 10/2011 | Igarashi et al. |
| 8,053,974 B2 | 11/2011 | Seo et al. |
| 8,084,145 B2 | 12/2011 | Inoue et al. |
| 8,247,964 B2 | 8/2012 | Igarashi et al. |
| 8,389,132 B2 | 3/2013 | Seo et al. |
| 8,742,108 B2 | 6/2014 | Igarashi et al. |
| 8,889,266 B2 | 11/2014 | Inoue et al. |
| 8,999,520 B2 | 4/2015 | Inoue et al. |
| 9,012,036 B2 * | 4/2015 | Inoue .............. C07F 15/0033 428/690 |
| 9,406,895 B2 * | 8/2016 | Inoue .............. C07F 15/0033 |
| 2004/0127710 A1 | 7/2004 | Park et al. |
| 2005/0056856 A1 | 3/2005 | Yamazaki et al. |
| 2005/0123792 A1 * | 6/2005 | Deaton .............. C09K 11/06 428/690 |
| 2005/0191527 A1 | 9/2005 | Fujii et al. |
| 2005/0221123 A1 | 10/2005 | Inoue et al. |
| 2005/0253135 A1 | 11/2005 | Stossel et al. |
| 2006/0036097 A1 | 2/2006 | Qiu et al. |
| 2006/0127696 A1 | 6/2006 | Stossel et al. |
| 2006/0263636 A1 | 11/2006 | Ohsawa et al. |
| 2007/0104979 A1 | 5/2007 | Kim et al. |
| 2007/0129545 A1 | 6/2007 | Inoue et al. |
| 2007/0231602 A1 | 10/2007 | Igarashi et al. |
| 2007/0244320 A1 | 10/2007 | Inoue et al. |
| 2007/0273273 A1 * | 11/2007 | Kim .............. C08G 61/02 313/504 |
| 2008/0132701 A1 | 6/2008 | Igarashi et al. |
| 2008/0233432 A1 | 9/2008 | Inoue et al. |
| 2009/0015143 A1 | 1/2009 | Inoue et al. |
| 2009/0033209 A1 * | 2/2009 | Seo .............. C07F 15/0033 313/504 |
| 2010/0145044 A1 | 6/2010 | Inoue et al. |
| 2010/0174071 A1 | 7/2010 | Igarashi et al. |
| 2011/0298360 A1 | 12/2011 | Ohsawa et al. |
| 2015/0214484 A1 | 7/2015 | Inoue et al. |

FOREIGN PATENT DOCUMENTS

| | | |
|---|---|---|
| EP | 1 424 382 A2 | 6/2004 |
| EP | 1 431 288 A2 | 6/2004 |
| EP | 1 431 289 A2 | 6/2004 |
| EP | 1 873 163 A1 | 1/2008 |
| EP | 2 147 006 A | 1/2010 |
| EP | 2 254 173 A1 | 11/2010 |
| EP | 2 299 785 A1 | 3/2011 |
| EP | 2 306 788 A1 | 4/2011 |
| EP | 2 306 789 A1 | 4/2011 |
| JP | 2000-212744 A | 8/2000 |
| JP | 2001-247859 A | 9/2001 |
| JP | 2002-105055 A | 4/2002 |
| JP | 2002-117978 A | 4/2002 |
| JP | 2005-314414 A | 11/2005 |
| JP | 2006-120762 A | 5/2006 |
| JP | 2006-151887 A | 6/2006 |
| JP | 2006-290988 A | 10/2006 |
| JP | 2006-352102 A | 12/2006 |
| JP | 2007-153865 A | 6/2007 |
| JP | 2007-176917 A | 7/2007 |
| JP | 2007-284432 A | 11/2007 |
| JP | 4657320 B2 | 3/2011 |
| JP | 5298065 B2 | 9/2013 |
| JP | 5624177 B2 | 11/2014 |
| JP | 5851005 B2 | 2/2016 |
| TW | I402328 | 7/2013 |
| WO | WO 2002/002714 A1 | 1/2002 |
| WO | WO 2003/063555 A1 | 7/2003 |
| WO | WO 2005/075597 A2 | 8/2005 |
| WO | WO 2006/095943 A1 | 9/2006 |
| WO | WO 2006/098460 A1 | 9/2006 |
| WO | WO 2006/104177 A1 | 10/2006 |
| WO | WO 2007/066556 A1 | 6/2007 |
| WO | WO 2008/143113 A1 | 11/2008 |

OTHER PUBLICATIONS

International Search Report re Application No. PCT/JP2008/058893, dated Jun. 10, 2008.
Written Opinion re Application No. PCT/JP2008/058893, dated Jun. 10, 2008.
Zhang, G-L. et al., "Synthesis and Phosphorescence of a New Iridium(III) Pyrazine Complex," Wuli Huaxue Xuebao (Acta Physico-Chimica Sinica), Oct. 19, 2003, vol. 19, No. 10, pp. 889-891.
Zhang, G-L. et al., "Synthesis and Luminescence Property of a New Yellow Phosphorescent Iridium(III) Pyrazine Complex" Chemical Journal of Chinese Universities, Mar. 1, 2004, vol. 25, No. 3, pp. 397-403
Inoue, H. et al., "A Reaction of Singlet Oxygen With an Unsaturated Organic Molecule, 6.1.4, Quencher and Photosensitizer," Basic Chemistry Course Photochemistry I, Sep. 30, 1999, pp. 106-110, Maruzen.
Adachi, C. et al., "High-Efficiency Red Electrophosphorescence Devices," Applied Physics Letters, Mar. 12, 2001, vol. 78, No. 11, pp. 1622-1624.
Tao, X.T. et al., "Metal Complex Polymer for Second Harmonic Generation and Electroluminescence Applications," Applied Physics Letters, Mar. 24, 1997, vol. 70, No. 12, pp. 1503-1505.
Taiwanese Office Action re Application No. TW 97118144, dated Jan. 24, 2013.
Taiwanese Office Action re Application No. TW 101150503, dated Aug. 20, 2014.
Korean Office Action re Application No. KR 2009-7025050, dated Sep. 16, 2014.

* cited by examiner

ORGANOMETALLIC COMPLEX, COMPOSITION AND LIGHT EMITTING ELEMENT INCLUDING THE ORGANOMETALLIC COMPLEX

This application is a continuation of copending application Ser. No. 14/688,429 filed on Apr. 16, 2015 which is a continuation of application Ser. No. 12/120,337 filed on May 14, 2008 (now U.S. Pat. No. 9,012,036 issued Apr. 21, 2015), which are all incorporated herein by reference.

TECHNICAL FIELD

The present invention relates to organometallic complexes and compositions including the organometallic complexes. Further, the present invention relates to light emitting elements, light emitting devices, and electronic devices which use electroluminescence, and a method for manufacturing the light emitting elements.

BACKGROUND ART

Organic compounds absorb light to be in an excited state. Organic compounds cause various reactions (such as photochemical reactions) or emit light (luminescence) in some cases through this excited state. Therefore, various applications of the organic compounds have been being made.

As one example of the photochemical reactions, there is a reaction (oxygen addition) of singlet oxygen with an unsaturated organic molecule (for example, see Non-patent Document 1: Haruo INOUE, et al., Basic Chemistry Course PHOTOCHEMISTRY I (published by Maruzen Co., Ltd.), pp. 106-110). Since the ground state of an oxygen molecule is a triplet state, oxygen in a singlet state (singlet oxygen) is not generated by direct photoexcitation. Singlet oxygen is generated in the presence of any other triplet excited molecule, which leads to an oxygen addition reaction. A compound which can be the triplet excited molecule is referred to as a photosensitizer.

As described above, a photosensitizer that can make a triplet excited molecule by photoexcitation is necessary in order to generate singlet oxygen. However, since the ground state of an ordinary organic compound is a singlet state, photoexcitation to a triplet excited state is a forbidden transition and a triplet excited molecule is unlikely formed. Therefore, a compound that can easily cause intersystem crossing from a singlet excited state to a triplet excited state (or a compound that allows a forbidden transition and is directly photoexcited to the triplet excited state) is required as a photosensitizer. In other words, such a compound can be used as a photosensitizer and is useful.

The compound often exhibits phosphorescence. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). Fields of application of a compound capable of exhibiting phosphorescence, that is, a compound capable of converting the triplet excited state into luminescence (hereinafter, referred to as a phosphorescent compound), include a light emitting element including an organic compound as a light emitting substance.

Such a light emitting element has a simple structure in which a light emitting layer including an organic compound which is a light emitting substance is provided between electrodes. This light emitting element attracts attention as a next-generation flat panel display element because of its characteristics such as a thin shape, lightweight, high response speed, and direct current low voltage driving. Further, a display device including this light emitting element is superior in contrast, image quality, and has a wide viewing angle.

In a light emitting element including an organic compound as a light emitting substance, an emission mechanism is a carrier injection type. In other words, when voltage is applied between electrodes which sandwich a light emitting layer, electrons and holes are injected from the electrodes and recombined to make the light emitting substance excited, and then, light is emitted when the electrons and holes return from the excited state to the ground state. As in the case of photoexcitation described above, types of the excited state include a singlet excited state (S*) and a triplet excited state (T*). The statistical generation ratio thereof in the light emitting element is considered to be S*:T*=1:3.

A compound capable of converting the singlet excited state to luminescence (hereinafter, referred to as a fluorescent compound) exhibits only luminescence from the singlet excited state (fluorescence), and does not exhibit luminescence from the triplet excited state (phosphorescence) at room temperature. Accordingly, the internal quantum efficiency (the ratio of generated photons to injected carriers) of a light emitting element including a fluorescent compound is assumed to have a theoretical limit of 25% based on S*:T*=1:3.

On the other hand, if the above-described phosphorescent compound is used, the internal quantum efficiency can be improved up to 75 to 100% in theory; that is, the light emission efficiency can be 3 to 4 times as high as that of a fluorescent compound is possible. Therefore, light emitting elements including a phosphorescent compound has been actively developed in recent years in order to realize highly-efficient light emitting elements (for example, see Non-patent Document 2: Chihaya ADACHI, et al., Applied Physics Letters, Vol. 78, No. 11, pp. 1622-1624. (2001)). An organometallic complex that includes iridium or the like as a central metal is particularly attracting attention as a phosphorescent compound because of its high phosphorescence quantum efficiency.

DISCLOSURE OF INVENTION

An organometallic complex like the organometallic complex disclosed in Non-patent Document 2 is expected to be used as a photosensitizer because it causes intersystem crossing easily. Further, since the organometallic complex exhibits luminescence (phosphorescence) from a triplet excited state easily, application of the organometallic complex to a light emitting element raises expectations for a highly-efficient light emitting element. However, in the present state, the number of kinds of such organometallic complexes is small.

Furthermore, a film of an organometallic complex such as the organometallic complex disclosed in Non-patent Document 2 is typically formed by a vacuum evaporation method and used for a light emitting element. However, a vacuum evaporation method has problems such as low material use efficiency and limitation on substrate size. Therefore, a film forming method other than a vacuum evaporation method has been examined for productization and mass production of light emitting elements.

A droplet discharge method or a spin coating method has been proposed as a method for forming an organic compound film over a large substrate. In such film formation, a solution in which an organic compound is dissolved in a solvent is used.

However, the above-described organometallic complex has low solubility, and accordingly, it has been impossible to prepare a solution with a sufficiently high concentration which can be used for film formation by a droplet discharge method or a spin coating method.

Thus, it is an object of the present invention to provide a novel organometallic complex.

It is another object of the present invention to provide a composition in which the organometallic complex is dissolved and to provide a method for manufacturing light emitting elements using the composition.

Furthermore, another object of the present invention is to provide a light emitting element, a light emitting device, and an electronic device which are manufactured using the organometallic complex.

The inventors of the present invention have found that an organometallic complex represented by a general formula (G1) has high solubility in a solvent.

An aspect of the present invention is an organometallic complex represented by the general formula (G1).

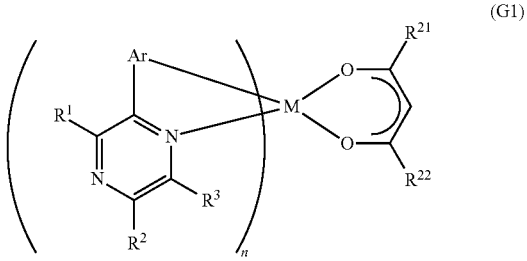

(G1)

In the formula, Ar represents an arylene group; $R^1$ represents an alkyl group or an aryl group; $R^2$ represents any one of hydrogen, an alkyl group, or an aryl group; and $R^3$ represents hydrogen or an alkyl group. Note that $R^2$ and $R^3$ may be bound to each other to form an alicyclic ring. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

Another aspect of the present invention is an organometallic complex represented by the general formula (G1).

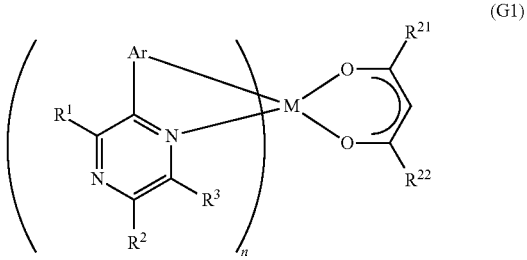

(G1)

In the formula, Ar represents an arylene group; $R^1$ represents an alkyl group or an aryl group; $R^2$ represents any one of hydrogen, an alkyl group, or an aryl group; and $R^3$ represents hydrogen or an alkyl group. Note that $R^2$ and $R^3$ may be bound to each other to form an alicyclic ring. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 4 carbon atoms or a haloalkyl group having 2 to 4 carbon atoms and the other one represents an alkyl group having 1 to 4 carbon atoms or a haloalkyl group having 1 to 4 carbon atoms.

An aspect of the present invention is an organometallic complex represented by the general formula (G1).

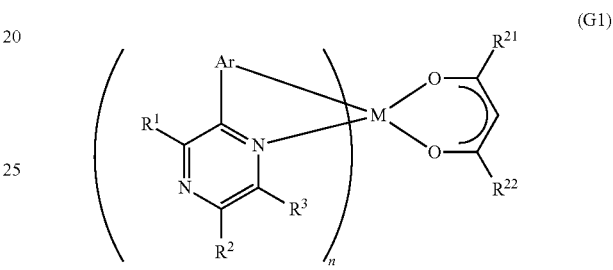

(G1)

In the formula, Ar represents an arylene group; $R^1$ represents an alkyl group or an aryl group; $R^2$ represents any one of hydrogen, an alkyl group, and an aryl group; and $R^3$ represents hydrogen or an alkyl group. Note that $R^2$ and $R^3$ may be bound to each other to form an alicyclic ring. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents a branched alkyl group having 3 to 4 carbon atoms and the other one represents an alkyl group having 1 to 4 carbon atoms or a haloalkyl group having 1 to 4 carbon atoms.

Another aspect of the present invention is an organometallic complex represented by the general formula (G1).

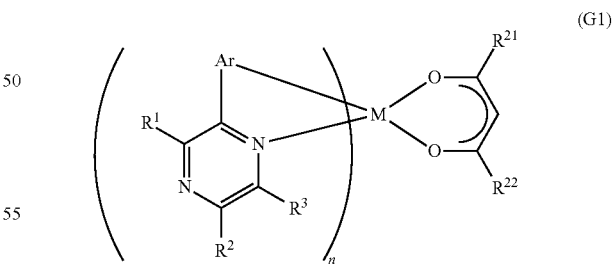

(G1)

In the formula, Ar represents an arylene group; $R^1$ represents an alkyl group or an aryl group; $R^2$ represents any one of hydrogen, an alkyl group, or an aryl group; R3 represents hydrogen or an alkyl group. Note that $R^2$ and $R^3$ may be bound to each other to form an alicyclic ring. In addition, M is a central metal and represents either an element belonging to Group 9 or an element belonging to Group 10. In addition, n is 2 when M is an element belonging to Group 9, and n is 1 when M is an element belonging to Group 10. Each of $R^{21}$ and $R^{22}$ represents a branched alkyl group having 3 to 4 carbon atoms.

Another aspect of the present invention is an organometallic complex represented by a general formula (G2).

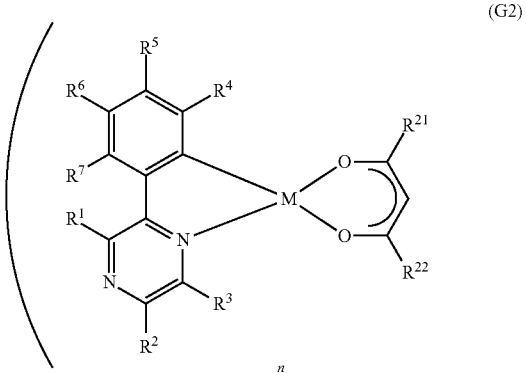

(G2)

In the formula, $R^1$ represents any one of an alkyl group, a phenyl group, or a phenyl group having a substituent; $R^2$ represents any one of hydrogen, an alkyl group, a phenyl group, or a phenyl group having a substituent; and $R^3$ represents hydrogen or an alkyl group. Note that $R^2$ and $R^3$ may be bound to each other to form an alicyclic ring. In addition, each of $R^4$ to $R^7$ represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

Another aspect of the present invention is an organometallic complex represented by the general formula (G2).

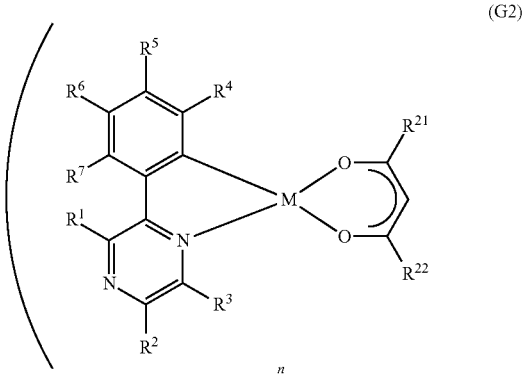

(G2)

In the formula, $R^1$ represents any one of an alkyl group, a phenyl group, or a phenyl group having a substituent; $R^2$ represents any one of hydrogen, an alkyl group, a phenyl group, or a phenyl group having a substituent; and $R^3$ represents hydrogen or an alkyl group. Note that $R^2$ and $R^3$ may be bound to each other to form an alicyclic ring. In addition, each of $R^4$ to $R^7$ represents any one of hydrogen, an alkyl group, a halogen group, a haloalkyl group, an alkoxy group, or an alkoxycarbonyl group. M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 4 carbon atoms or a haloalkyl group having 2 to 4 carbon atoms and the other one represents an alkyl group having 1 to 4 carbon atoms or a haloalkyl group having 1 to 4 carbon atoms.

Another aspect of the present invention is an organometallic complex represented by the general formula (G2).

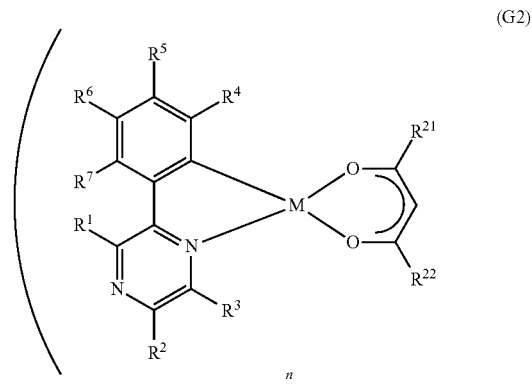

(G2)

In the formula, $R^1$ represents any one of an alkyl group, a phenyl group, or a phenyl group having a substituent; $R^2$ represents any one of hydrogen, an alkyl group, a phenyl group, or a phenyl group having a substituent; and $R^3$ represents hydrogen or an alkyl group. Note that $R^2$ and $R^3$ may be bound to each other to form an alicyclic ring. In addition, each of $R^4$ to $R^7$ represents any one of hydrogen, an alkyl group, a halogen group, a haloalkyl group, an alkoxy group, or an alkoxycarbonyl group. M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents a branched alkyl group having from 3 to 4 carbon atoms and the other one represents an alkyl group having 1 to 4 carbon atoms or a haloalkyl group having 1 to 4 carbon atoms.

Another aspect of the present invention is an organometallic complex represented by the general formula (G2).

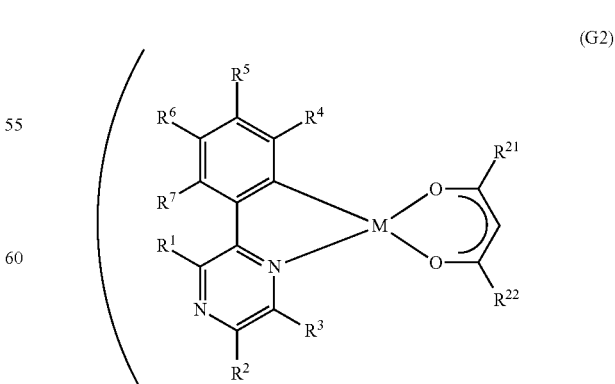

(G2)

In the formula, R¹ represents any one of an alkyl group, a phenyl group, or a phenyl group having a substituent; R² represents any one of hydrogen, an alkyl group, a phenyl group, or a phenyl group having a substituent; and R³ represents hydrogen or an alkyl group. Note that R² and R³ may be bound to each other to form an alicyclic ring. In addition, each of R⁴ to R⁷ represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. Each of $R^{21}$ and $R^{22}$ represents a branched alkyl group having 3 to 4 carbon atoms.

Another aspect of the present invention is an organometallic complex represented by a general formula (G3).

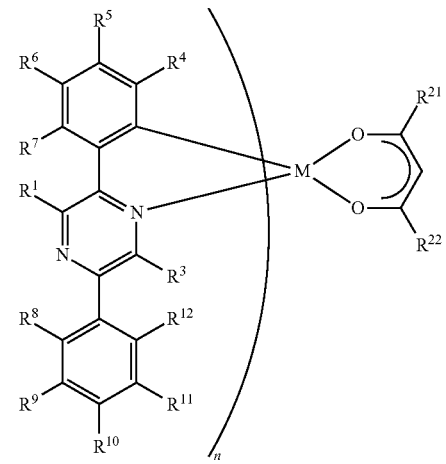

(G3)

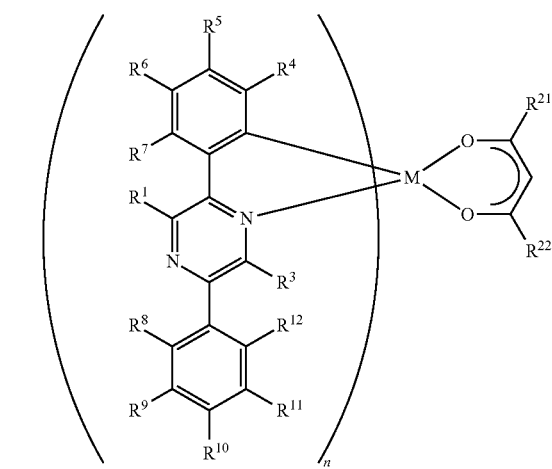

(G3)

In the formula, R¹ represents any one of an alkyl group, a phenyl group, or a phenyl group having a substituent; R³ represents hydrogen or an alkyl group; and each of R⁴ to R¹² represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

Another aspect of the present invention is an organometallic complex represented by the general formula (G3).

In the formula, R¹ represents any one of an alkyl group, a phenyl group, or a phenyl group having a substituent; R³ represents hydrogen or an alkyl group; and each of R⁴ to R¹² represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 4 carbon atoms or a haloalkyl group having 2 to 4 carbon atoms and the other one represents an alkyl group having 1 to 4 carbon atoms or a haloalkyl group having 1 to 4 carbon atoms.

Another aspect of the present invention is an organometallic complex represented by the general formula (G3).

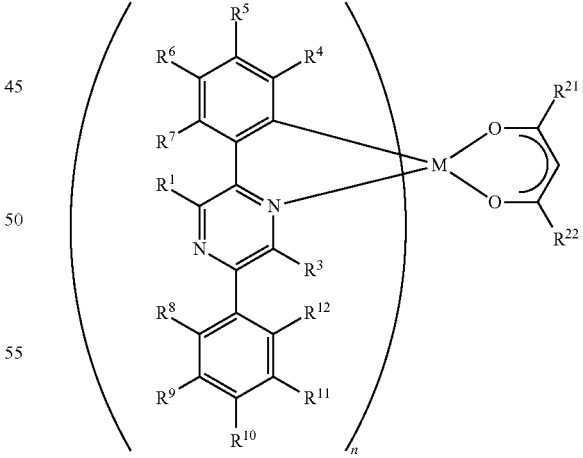

(G3)

In the formula, R¹ represents any one of an alkyl group, a phenyl group, or a phenyl group having a substituent; R³ represents hydrogen or an alkyl group; and each of R⁴ to R¹² represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents a branched alkyl group having 3 to 4 carbon atoms and the other one represents an alkyl group having 1 to 4 carbon atoms or a haloalkyl group having 1 to 4 carbon atoms.

Another aspect of the present invention is an organometallic complex represented by the general formula (G3).

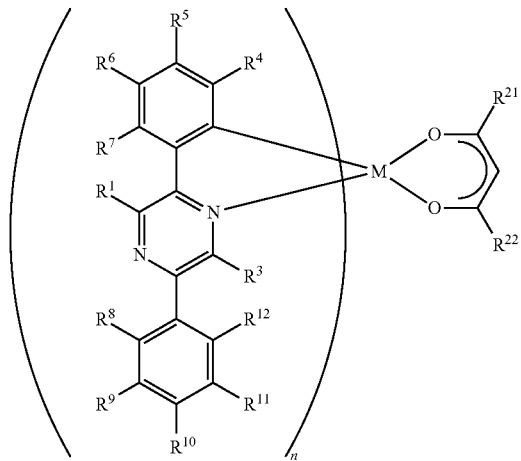

(G3)

In the formula, $R^1$ represents any one of an alkyl group, a phenyl group, or a phenyl group having a substituent; $R^3$ represents hydrogen or an alkyl group; and each of $R^4$ to $R^{12}$ represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. Each of $R^{21}$ and $R^{22}$ represents a branched alkyl group having 3 to 4 carbon atoms.

In the above-described structures, the central metal M is preferably iridium or platinum in terms of emission efficiency.

Another aspect of the present invention is a composition including the above-described organometallic complex and a solvent.

Note that any of the above-described organometallic complexes is preferably dissolved in a solvent at a concentration of equal to or higher than 0.6 g/L, in consideration of using the above-described composition for manufacturing light emitting elements. More preferably, any of the above-described organometallic complexes is preferably dissolved in a solvent at a concentration of equal to or higher than 0.9 g/L.

In the above-described composition, any of a variety of solvents can be used as the solvent. The above-described organometallic complexes are soluble even in an organic solvent not including an aromatic ring. Further, the organometallic complexes are soluble even in ether or alcohol.

In consideration of using the above-described composition for manufacturing light emitting elements, it is preferable that the solvent be an organic solvent having a boiling point of equal to or higher than 50° C. and equal to or less than 200° C. because the solvent needs to be removed for film formation.

In the above-described composition, an organic semiconductor material may further be included.

Further, in the above-described composition, a binder may further be included.

The present invention includes a light emitting element manufactured using the above-described organometallic complex. In other word, another aspect of the present invention is a light emitting element including the above-described organometallic complex between a pair of electrodes.

The above-described organometallic complex has high light emission efficiency, and therefore, is preferably used for a light emitting layer. Accordingly, another aspect of the present invention is a light emitting element including a light emitting layer between a pair of electrodes, in which the light emitting layer includes the above-described organometallic complex.

Another aspect of the present invention is a light emitting element including a layer including the above-described organometallic complex and a high molecular compound between a pair of electrodes. In the above-described structure, the high molecular compound is an organic semiconductor material.

In the above-described structure, the high molecular compound is a binder. In addition, the layer including an organometallic complex and a high molecular compound further includes an organic semiconductor material.

In the above-described structure, the layer including an organometallic complex and a high molecular compound is preferably a light emitting layer.

In addition, a hole-transporting layer which is in contact with the light emitting layer includes a low molecular compound. Further, an electron-transporting layer which is in contact with the light emitting layer includes a low molecular compound.

A light emitting device of the present invention includes the above-described light emitting element. Further, a light emitting device of the present invention includes a control circuit which controls light emission of the light emitting element. Note that a light emitting device in this specification refers to an image display device, a light emitting unit, or a light source (including a lighting device). Further, the light emitting device also refers to a module in which a connector such as a flexible printed circuit (FPC), a tape automated bonding (TAB) tape, or a tape carrier package (TCP) is attached to a panel or a module in which a printed wiring board is provided at an end of a TAB tape or a TCP. Further, the light emitting device in this specification also refers to a light emitting element on which an integrated circuit (IC) is directly mounted by a chip on glass (COG) method.

The present invention also includes an electronic device which includes a light emitting element of the present invention in its display portion. Accordingly, an electronic device of the present invention includes a display portion, in which the display portion includes the above-described light emitting element and control circuit which controls light emission of the light emitting element.

The present invention also includes a method for manufacturing a light emitting element using the above-described composition. Thus, another aspect of the present invention is a method for manufacturing a light emitting element, including forming a first electrode, applying the above-described composition and removing a solvent, and forming a second electrode.

Another aspect of the present invention is a method for manufacturing a light emitting element, including forming a first electrode, forming a layer including an organic compound by an evaporation method, applying the above-described composition including a solvent and removing the solvent, and forming a second electrode.

Another aspect of the present invention is a method for manufacturing a light emitting element, including forming a first electrode, applying the above-described composition including a solvent and removing the solvent, forming a layer including an organic compound by an evaporation method, and forming a second electrode.

An organometallic complex of the present invention has a high solubility in a solvent. In addition, an organometallic complex of the present invention has high light emission efficiency.

Further, a composition of the present invention has an organometallic complex dissolved therein and is preferably used for manufacturing light emitting elements.

A method for manufacturing a light emitting element, which is suitable for industrial application, can be realized using a composition of the present invention for manufacturing light emitting elements.

Light emitting elements manufactured using a composition of the present invention can have high emission efficiency.

A light emitting device and an electronic device of the present invention includes a light emitting element having high emission efficiency, and therefore consumes less power.

BEST MODE FOR CARRYING OUT THE INVENTION

Figure 1:
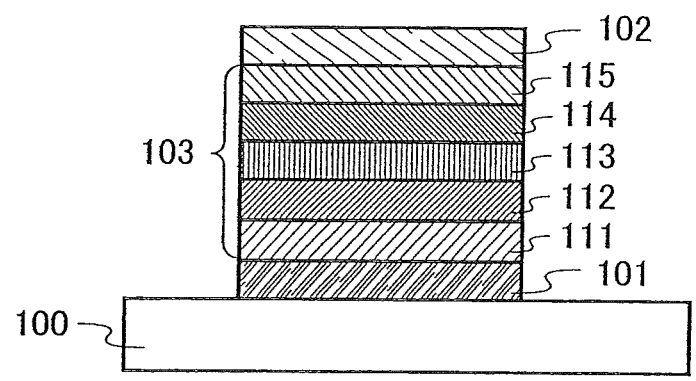
FIG. 1 illustrates a light emitting element of the present invention.

Hereinafter, embodiment modes and examples of the present invention will be described with reference to the drawings. Note that modes and details of the present invention can be modified in various ways without departing from the spirit and scope of the present invention. Accordingly, the present invention should not be construed as being limited to the description of the embodiment modes and the examples given below.

Embodiment Mode 1

This embodiment mode describes an organometallic complex of the present invention and a composition including the organometallic complex.

An organometallic complex of the present invention has a ligand including a pyrazine skeleton which is cyclometalated to a central metal. There are various ligands including a pyrazine skeleton, and if the ligand is a 2-arylpyrazine derivative, the ligand can be cyclometalated to a central metal. The cyclometalated complex has high phosphorescence quantum efficiency. Therefore, the ligand including a pyrazine skeleton preferably is a 2-arylpyrazine derivative.

In addition, in an organometallic complex of the present invention, a chelate ligand having a β diketone structure represented by a general formula (L0) is coordinated to the central metal as well as the above-described ligand including a pyrazine skeleton. In other words, an organometallic complex of the present invention includes two kinds of ligands: a ligand including a pyrazine skeleton and a chelate ligand represented by the general formula (L0).

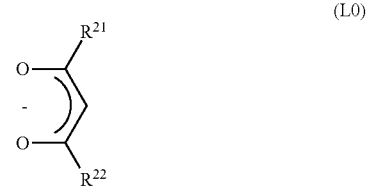

(L0)

In the general formula (L0), one of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

The inventors of the present invention have found that an organometallic complex including above-described two kinds of ligands has extremely high solubility in an organic solvent. In specific, the inventors of the present invention have found that an organometallic complex including above-described two kinds of ligands is soluble in a general alcohol solvent such as methanol, ethanol, or isopropanol as well as in a halogen-based solvent such as dichloromethane, dichloroethane, or chloroform; and an aromatic hydrocarbon-based solvent such as toluene or xylene.

Another aspect of the present invention is an organometallic complex represented by the general formula (G1).

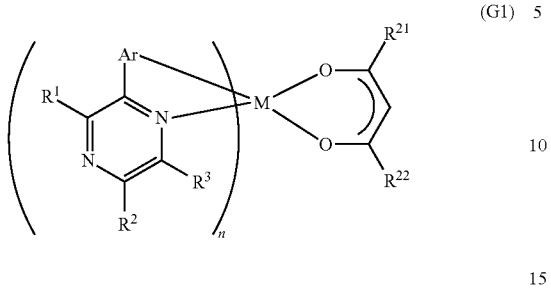

(G1)

In the formula, Ar represents an arylene group; $R^1$ represents an alkyl group or an aryl group; $R^2$ represents any one of hydrogen, an alkyl group, or an aryl group; and $R^3$ represents hydrogen or an alkyl group. Note that $R^2$ and $R^3$ may be bound to each other to form an alicyclic ring. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

In the organometallic complex represented by the general formula (G1), the ligand including a pyrazine skeleton is bound to an atom belonging to Group 9 (Co, Rh, or Ir) or an atom belonging to Group 10 (Ni, Pd, or Pt). That is, the central metal is an element belonging to Group 9 or an element belonging to Group 10. The binding of the ligand including a pyrazine skeleton to an element belonging to Group 9 or an element belonging to Group 10 can achieve high light emission efficiency.

Since an organometallic complex represented by the general formula (G1) has extremely high solubility in a solvent, the concentration of the organometallic complex in a solution can be adjusted as appropriate for forming a layer including the organometallic complex. In addition, an organometallic complex represented by the general formula (G1) is soluble in a general alcohol solvent such as methanol, ethanol, or isopropanol as well as in a halogen-based solvent such as dichloromethane, dichloroethane, or chloroform or an aromatic hydrocarbon-based solvent such as toluene or xylene; therefore, there are many choices for solvents. Accordingly, it is possible to form a layer including an organometallic complex represented by the general formula (G1) by a wet process over a layer that has been already formed.

Further, when a 2-phenylpyrazine derivative which is a kind of a 2-arylpyrazine derivative is the ligand, the ligand can be subjected to orthometallation with the central metal (orthometallation is a kind of cyclometalation). An orthometallated complex including thus orthometallated 2-phenylpyrazine can have particularly high phosphorescence quantum efficiency. Therefore, a preferred mode of the ligand including a pyrazine skeleton is a 2-phenylpyrazine derivative. An organometallic complex represented by the general formula (G2) is given as an organometallic complex including an orthometallated 2-phenylpyrazine derivative.

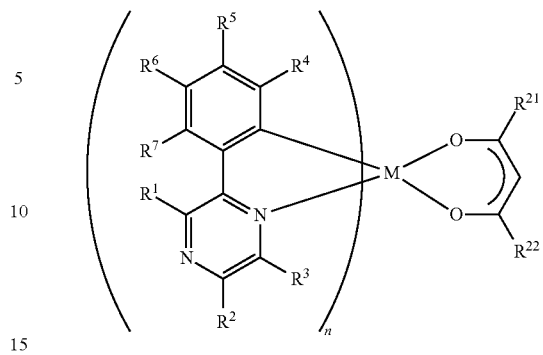

(G2)

In the formula, $R^1$ represents any one of an alkyl group, a phenyl group, or a phenyl group having a substituent; $R^2$ represents any one of hydrogen, an alkyl group, a phenyl group, or a phenyl group having a substituent; and $R^3$ represents hydrogen or an alkyl group. Note that $R^2$ and $R^3$ may be bound to each other to form an alicyclic ring. In addition, each of $R^4$ to $R^7$ represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

In the general formula (G2), if $R^2$ is a substituted or unsubstituted phenyl group, red-color light emission with high color purity and high luminous efficiency (cd/A) can be obtained. In other words, among organometallic complexes in which a 2-phenylpyrazine derivative is orthometallated, an organometallic complex in which a 2,5-diphenylpyrazine derivative is orthometallated is preferable. An organometallic complex represented by the general formula (G3) is given as an organometallic complex including an orthometallated 2,5-diphenylpyrazine derivative.

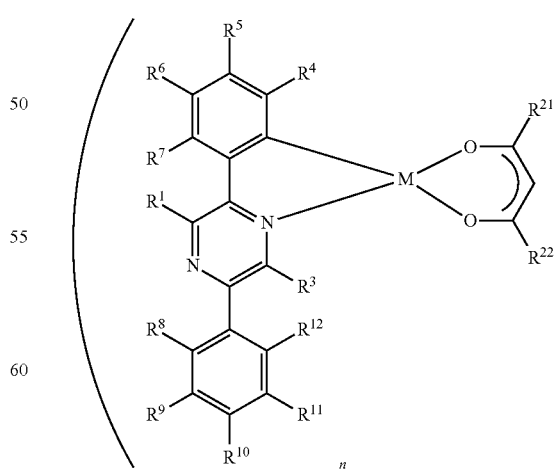

(G3)

In the formula, $R^1$ represents any one of an alkyl group, a phenyl group, or a phenyl group having a substituent; $R^3$ represents hydrogen or an alkyl group; and each of $R^4$ to $R^{12}$ represents any one of hydrogen, an alkyl group, a halogen group, a haloalkyl group, an alkoxy group, or an alkoxycarbonyl group. In addition, M is a central metal and represents either an element belonging to Group 9 or an element belonging to Group 10. In addition, n is 2 when M is an element belonging to Group 9, and n is 1 when M is an element belonging to Group 10. One of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

In the above-described structure, an arylene group having 6 to 25 carbon atoms is preferably used as an arylene group Ar. In specific, a substituted or unsubstituted 1,2-phenylene group, 8,9-julolidylene group, 1,2-naphthylene group, 2,3-naphthylene group, spiro fluorene-2,3-diyl group, or 9,9-dialkylfluorene-2,3-diyl group such as a 9,9-dimethylfluorene-2,3-diyl group can be employed. If the arylene group Ar is a substituted or unsubstituted 1,2-phenylene group, rise in vaporizing temperature caused by increase in molecular weight can be suppressed, which is especially advantageous when the organometallic complex is vaporized for sublimation purification or the like. In the case where the 1,2-phenylene group has a substituent, specific examples of the substituent are an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; a haloalkyl group such as a trifluoromethyl group; and an alkoxycarbonyl group such as a methoxycarbonyl group, an ethoxycarbonyl group, an isopropoxy carbonyl group, or a tert-butoxycarbonyl group. Note that an unsubstituted 1,2-phenylene group is particularly preferable among the specific examples of the arylene group Ar.

In the above-described structure, the aryl group can be a substituted or unsubstituted phenyl group, 1-naphthyl group, 2-naphthyl group, spirofluorene-2-yl group, 9,9-dialkylfluorene-2-yl group such as a 9,9-dimethylfluorene-2-yl group, or the like. Note that an aryl group having 6 to 25 carbon atoms is preferable in consideration of solubility in a solvent. In the case of the above-described aryl group has a substituent, the substituent can be an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; a haloalkyl group such as a trifluoromethyl group; or an alkoxycarbonyl group such as a methoxycarbonyl group, an ethoxycarbonyl group, an isopropoxy carbonyl group, or a tert-butoxycarbonyl group.

Further in the above-described structure, the substituent of the phenyl group having a substituent can be an alkyl group such as a methyl group, an ethyl group, an isopropyl group, or a tert-butyl group; an alkoxy group such as a methoxy group, an ethoxy group, an isopropoxy group, or a tert-butoxy group; an aryl group such as a phenyl group or a 4-biphenylyl group; a halogen group such as a fluoro group; a haloalkyl group such as a trifluoromethyl group; and an alkoxycarbonyl group such as a methoxycarbonyl group, an ethoxycarbonyl group, an isopropoxy carbonyl group, or a tert-butoxycarbonyl group can be given.

In the above-described structure, the alkyl group can be a methyl group, an ethyl group, an isopropyl group, a tert-butyl group, a cyclohexyl group, a pentyl group, or the like. Note that an alkyl group having 5 or more carbon atoms is preferable in consideration of solubility of the above-described organometallic complex in a solvent. However, the above-described organometallic complex has high solubility even in the case of having an alkyl group having 4 or less carbon atoms. In other words, it is one aspect of an organometallic complex of the present invention that the alkyl group is an alkyl group having 4 or less carbon atoms, such as a methyl group, an ethyl group, an isopropyl group, or a tert-butyl group, in the above-described organometallic complex.

In the above-described structure, a fluoro group, a chloro group, or the like can be given as a halogen group, and a fluoro group is preferable in terms of chemical stability. As a haloalkyl group, a trifluoromethyl group is preferable.

In the above-described structure, the alkoxy group can be a methoxy group, an ethoxy group, an isopropoxy group, a tert-butoxy group, or the like. The above-described organometallic complex has high solubility even in the case of having an alkoxy group having 4 or less carbon atoms. In other words, it is one aspect of an organometallic complex of the present invention that the alkoxy group is an alkoxy group having 4 or less carbon atoms, such as a methoxy group, an ethoxy group, an isopropoxy group, or a tert-butoxy group, in the above-described organometallic complex.

In the above-described structure, an alkoxycarbonyl group can be a methoxycarbonyl group, an ethoxycarbonyl group, an isopropoxy carbonyl group, a tert-butoxycarbonyl group, or the like. The above-described organometallic complex has high solubility even in the case of having an alkoxycarbonyl group having 5 or less carbon atoms. In other words, it is one aspect of an organometallic complex of the present invention that the alkoxycarbonyl group is an alkoxycarbonyl group having 5 or less carbon atoms, such as a methoxycarbonyl group, an ethoxycarbonyl group, an isopropoxy carbonyl group, or a tert-butoxycarbonyl group.

In the above-described general formula (L0) and the general formulae (G1) to (G3), one of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms. The inventors of the present invention have found that an organometallic complex of the present invention can have sufficient solubility when any one of ligands represented by general formulae (L1) to (L10) can be given as a ligand represented by the general formula (L0), in other words, either $R^{21}$ or $R^{22}$ has 2 or more carbon atoms.

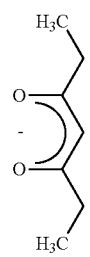

(L1)

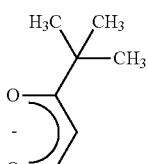
(L2)

(L3)

(L4)

(L5)

(L6)

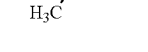
(L7)

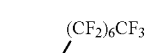
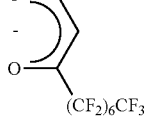
(L8)

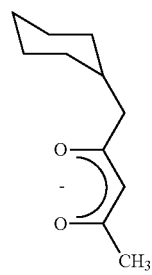
(L9)

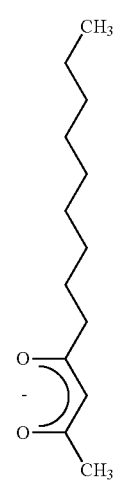
(L10)

As the number of carbon atoms in $R^{21}$ and $R^{22}$ is increased, the solubility is improved. However, the solubility of the above-described organometallic complex is high even when each of $R^{21}$ and $R^{22}$ are an alkyl group having 4 or less carbon atoms or a haloalkyl group having 4 or less carbon atoms. In other words, it is one aspect of an organometallic complex of the present invention that each of $R^{21}$ and $R^{22}$ are an alkyl group having 4 or less carbon atoms such as a methyl group, an ethyl group, an isopropyl group, or a tert-butyl group or a haloalkyl group having 4 or less carbon atoms such as a trifluoromethyl group.

Therefore, in the above-described general formula (L0) and the general formulae (G1) to (G3), it is preferable that one of $R^{21}$ and $R^{22}$ represent an alkyl group having 2 to 4 carbon atoms or a haloalkyl group having 2 to 10 carbon atoms and the other one represent an alkyl group having 1 to 4 carbon atoms or a haloalkyl group having 1 to 4 carbon atoms.

An organometallic complex of the present invention has high solubility even without a long chain alkyl group; therefore, movement of carriers is not interrupted when the organometallic complex of the present invention is used for a light emitting element. In addition, when an organometallic complex of the present invention is used as a light emitting substance of the light emitting element, there is an advantage that carrier injection to the organometallic complex of the present invention is not interrupted.

Further, it is particularly preferable that each of $R^{21}$ and $R^{22}$ be a branched alkyl group, because the solubility is further improved.

Therefore, in the above-described general formula (L0) and the general formulae (G1) to (G3), it is preferable that one of $R^{21}$ and $R^{22}$ represent a branched alkyl group having 3 to 4 carbon atoms and the other one represent an alkyl group having 1 to 4 carbon atoms or a haloalkyl group having 1 to 4 carbon atoms.

Further, it is preferable that each of $R^{21}$ and $R^{22}$ be a branched alkyl group, because the solubility is further improved.

Therefore, in the foregoing general formula (L0) and the general formulae (G1) to (G3), each of $R^{21}$ and $R^{22}$ preferably represents a branched alkyl group having 3 to 4 carbon atoms.

In addition, in the general formulae (G1) to (G3), $R^3$ is preferably hydrogen for convenience of synthesis. It is preferable that $R^3$ be hydrogen in terms of synthetic yield because steric hindrance of a ligand is reduced and the ligand is easily bonded to a metal ion.

Further in addition, iridium and platinum are preferable as the central metal M of the above-described organometallic complex in terms of heavy atom effect. In particular, iridium is preferable because iridium is chemically stable and shows pronounced heavy atom effect which leads to high efficiency.

Organometallic complexes represented by structural formulae (101) to (178) are given as specific examples of the above-described organometallic complex, but the present invention is not limited to those organometallic complexes.

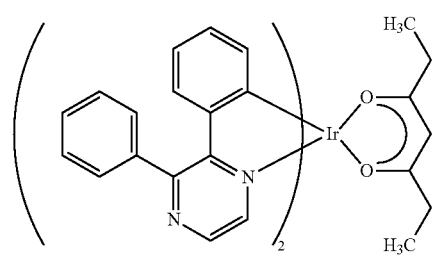
(101)

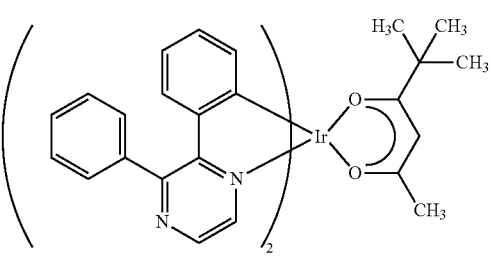
(102)

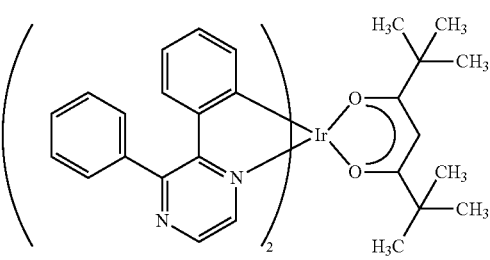
(103)

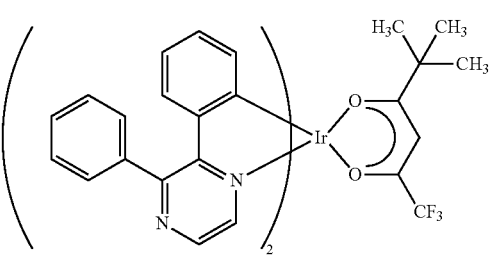
(104)

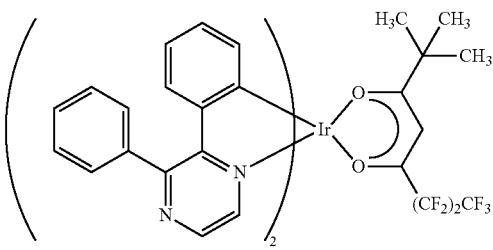
(105)

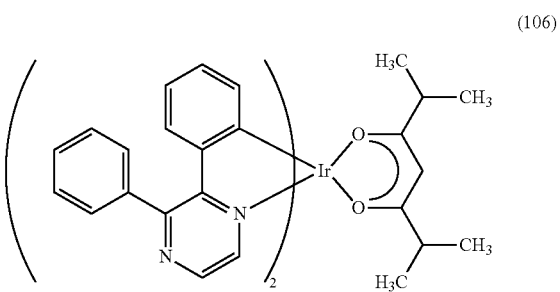
(106)

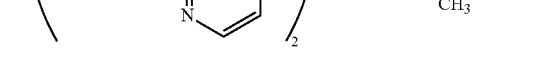
(107)

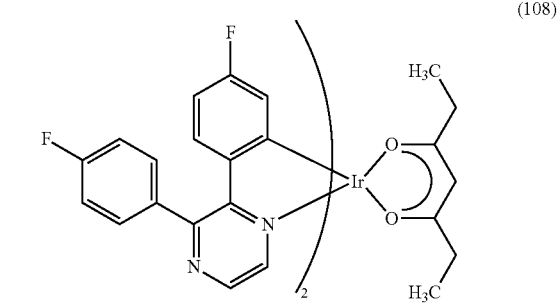
(107)

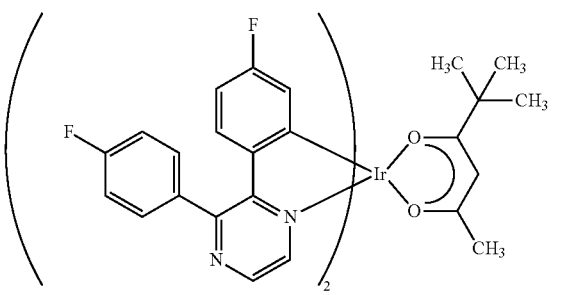
(108)

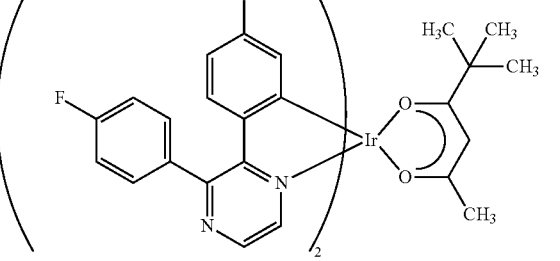
(109)

(110)
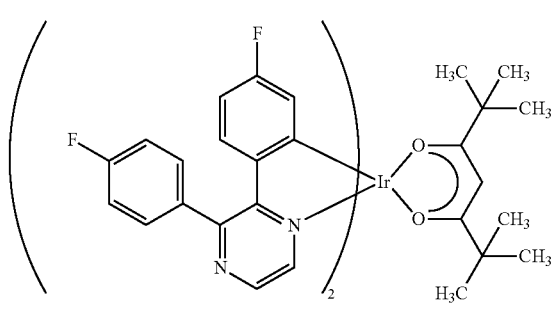
(115)
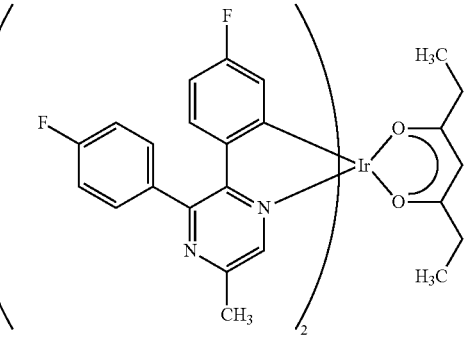
(111)
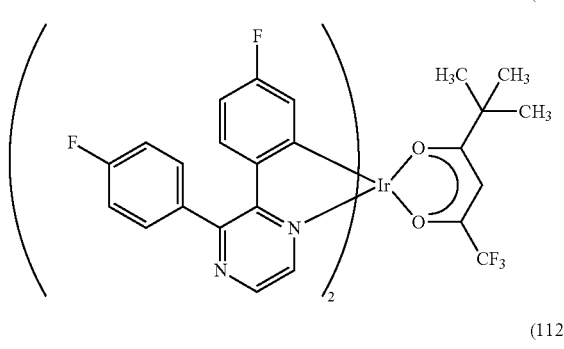
(116)
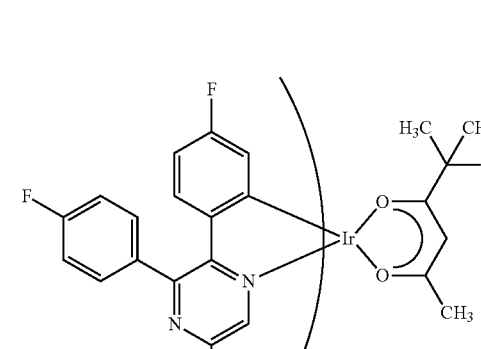
(112)
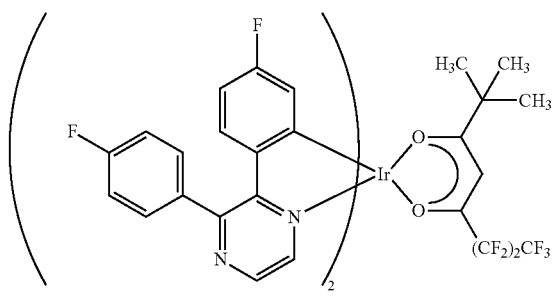
(117)
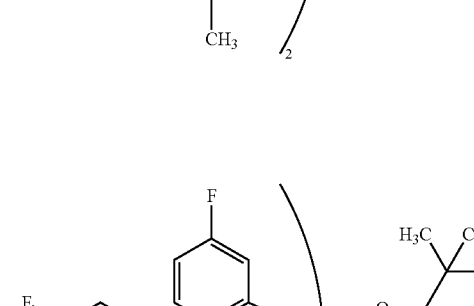
(113)
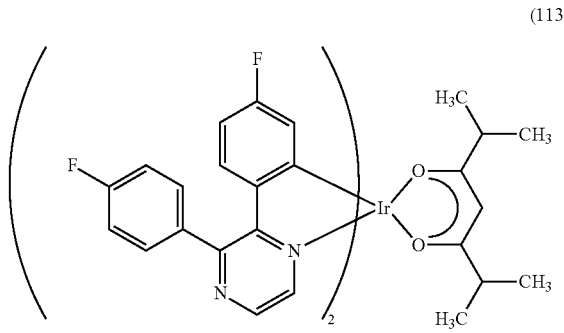
(114)
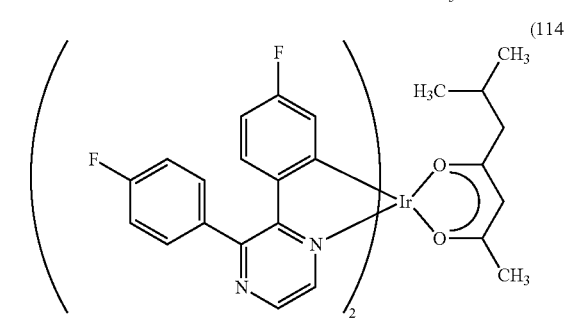
(118)
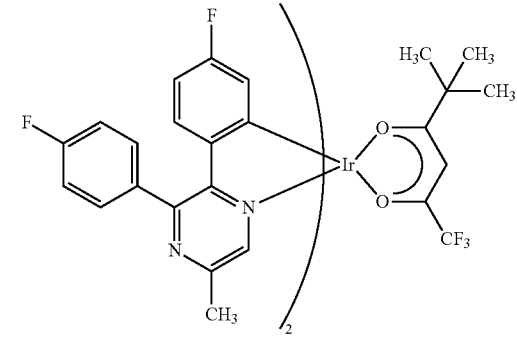

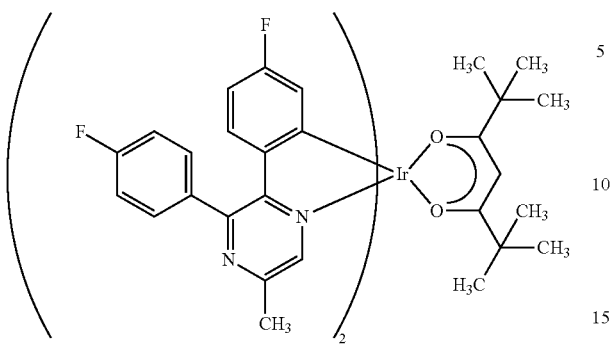
(119)
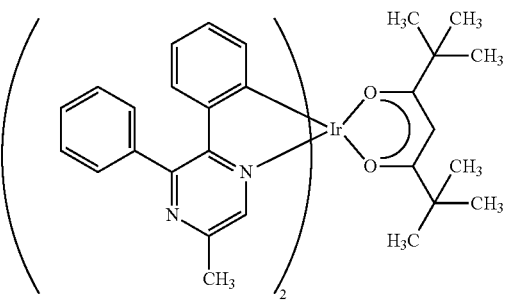
(123)
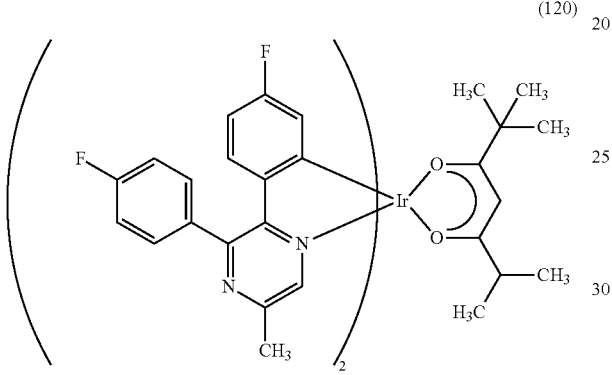
(120)
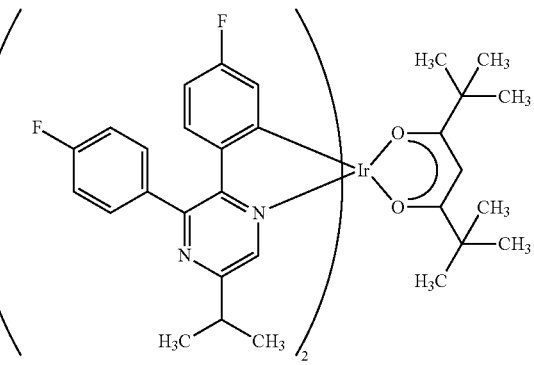
(124)
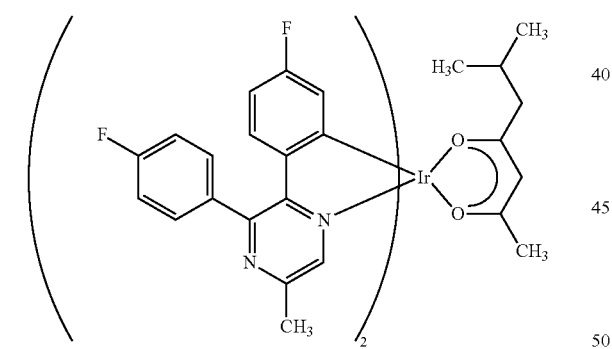
(121)
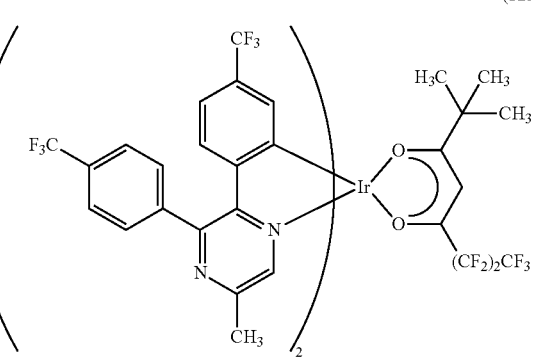
(125)
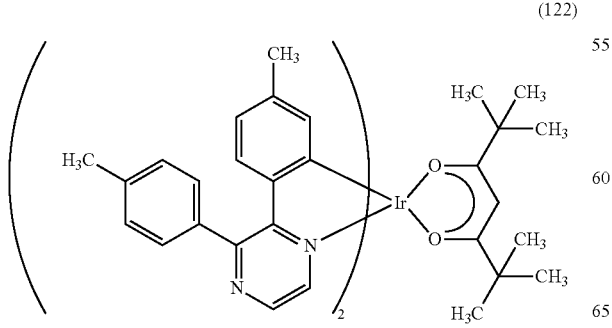
(122)
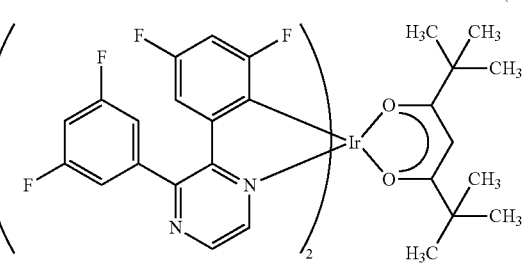
(126)

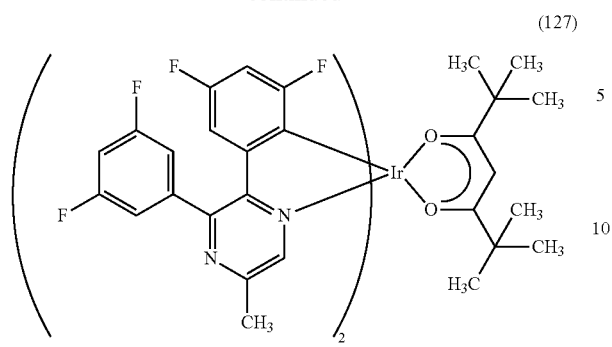
(127)
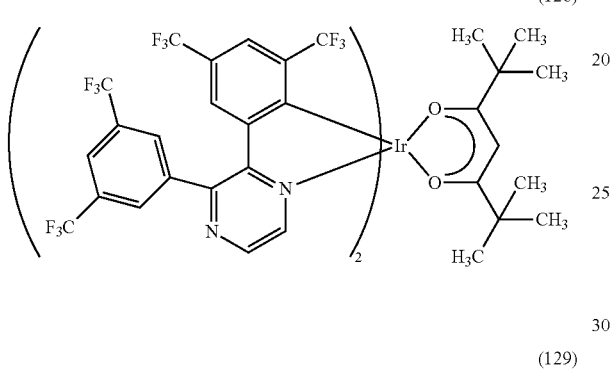
(128)
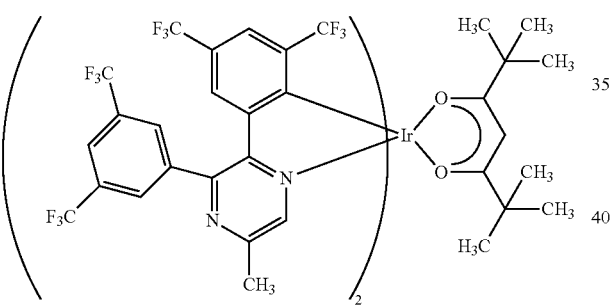
(129)
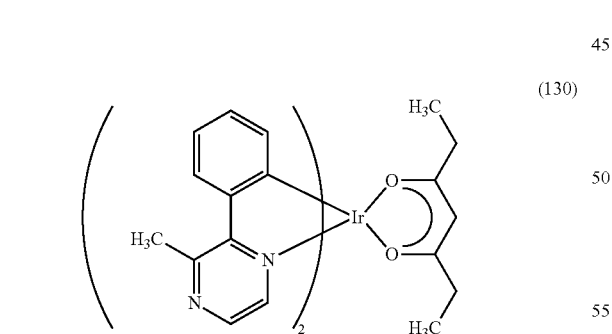
(130)
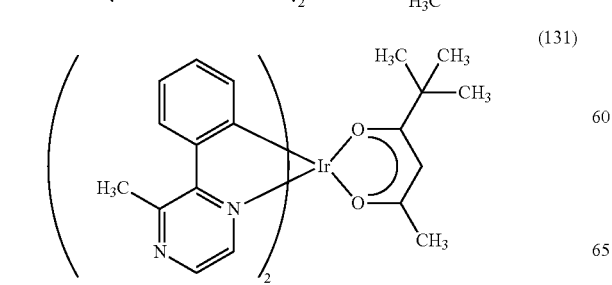
(131)
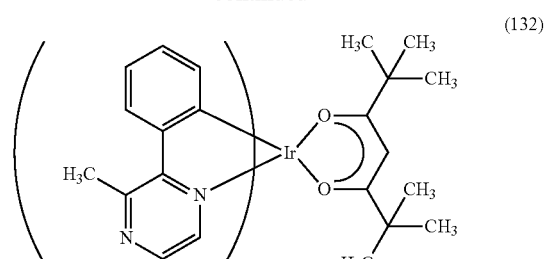
(132)
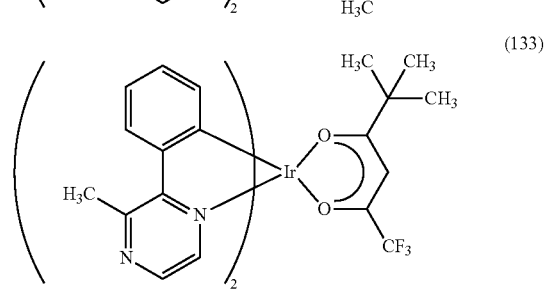
(133)
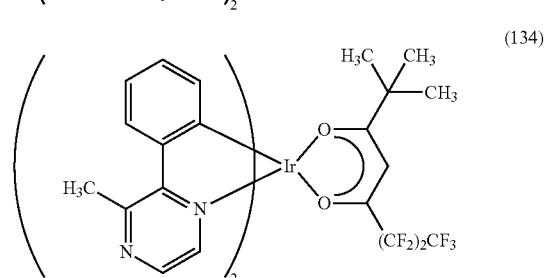
(134)
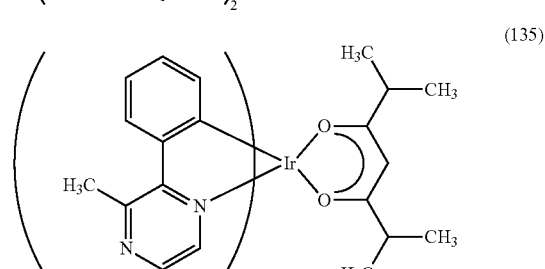
(135)
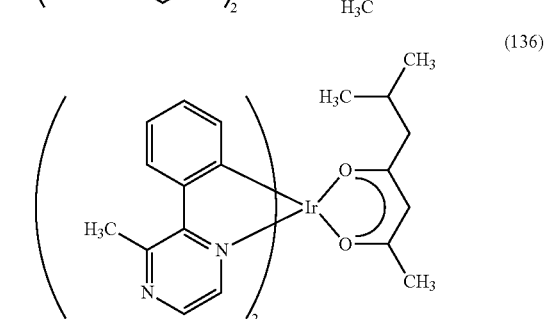
(136)
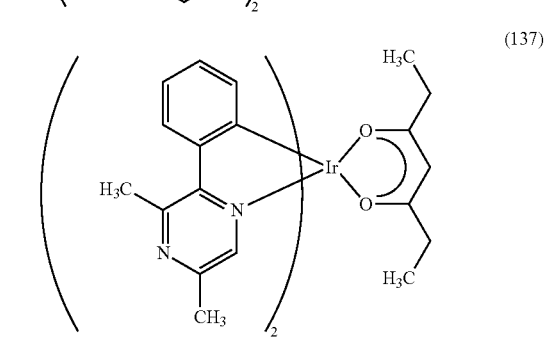
(137)

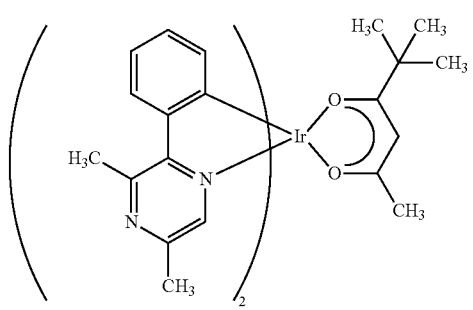
(138)
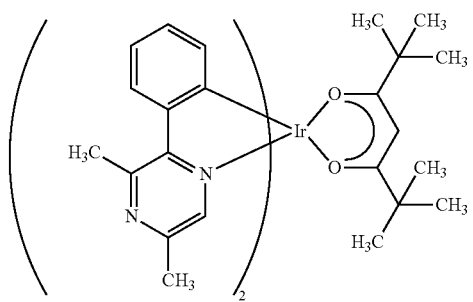
(139)
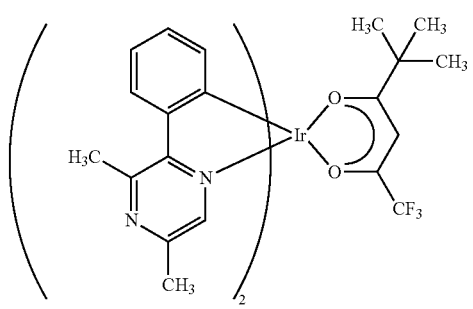
(140)
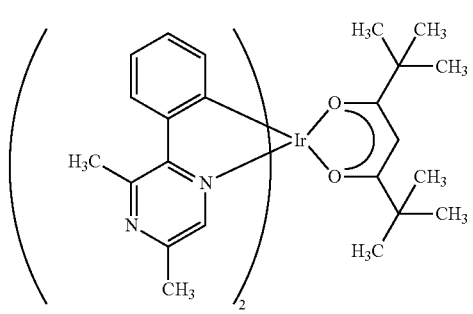
(141)
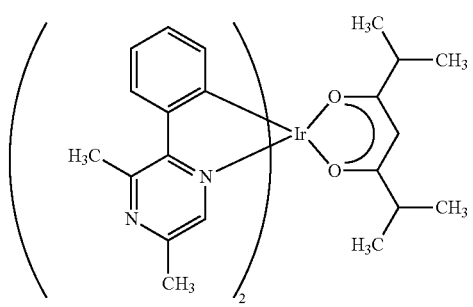
(142)
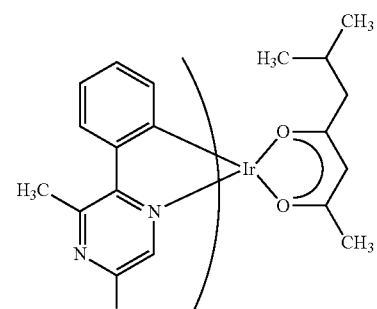
(143)
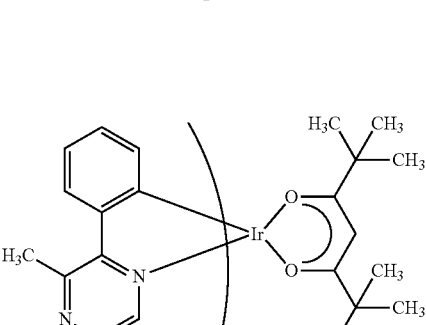
(144)
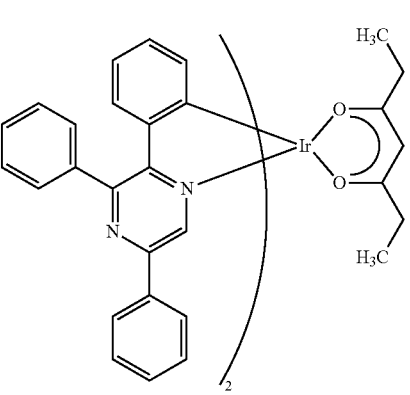
(145)
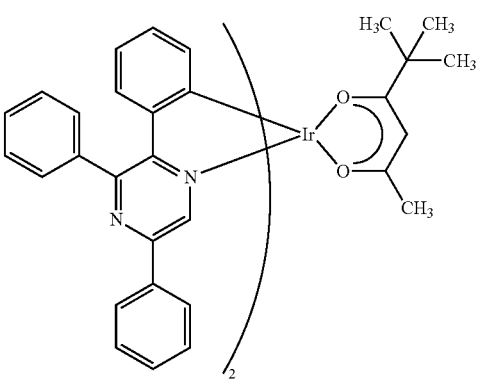
(146)

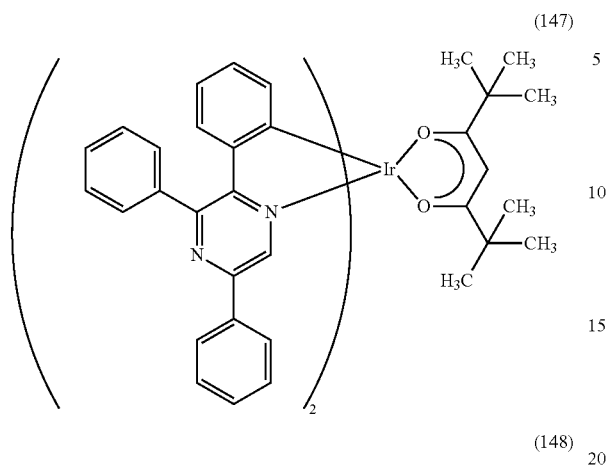
(147)
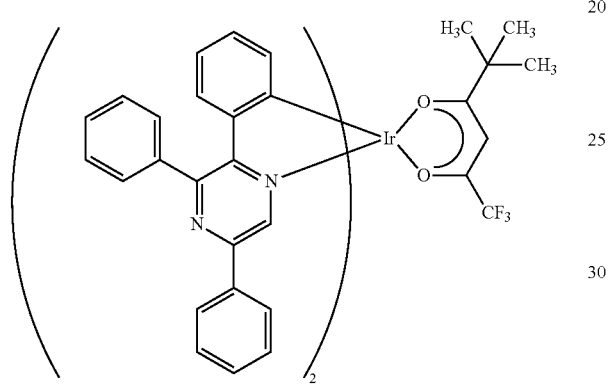
(148)
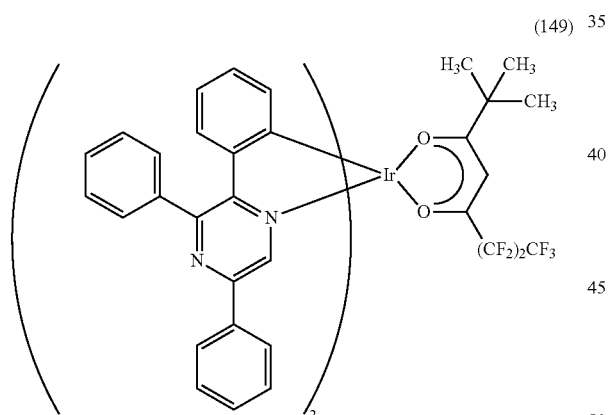
(149)
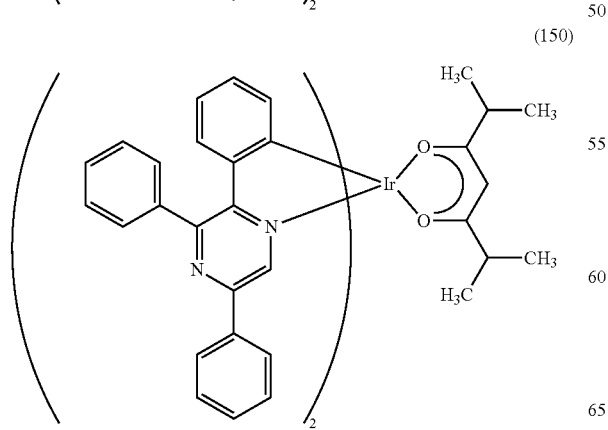
(150)
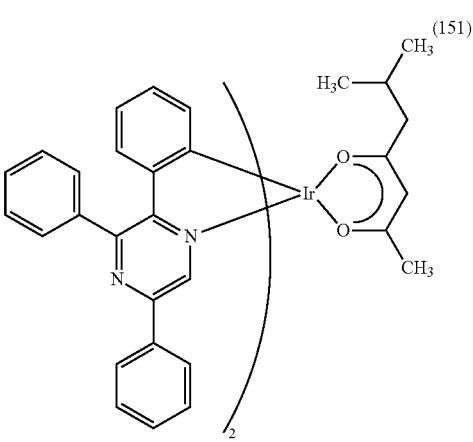
(151)
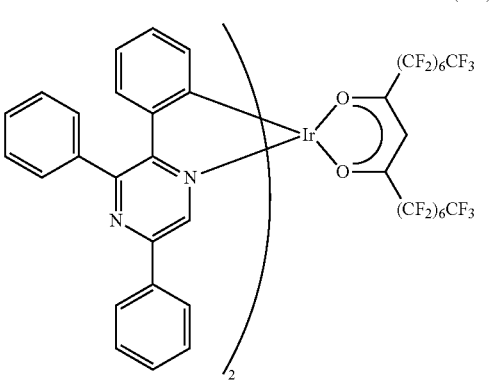
(152)
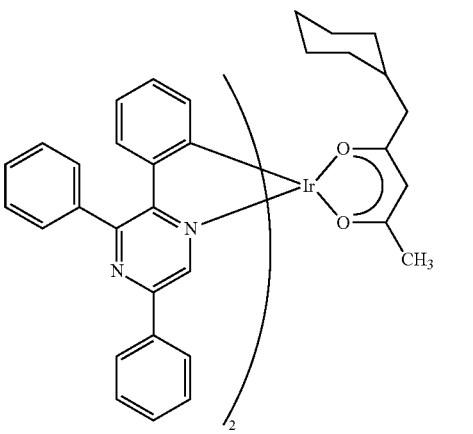
(153)

(154)
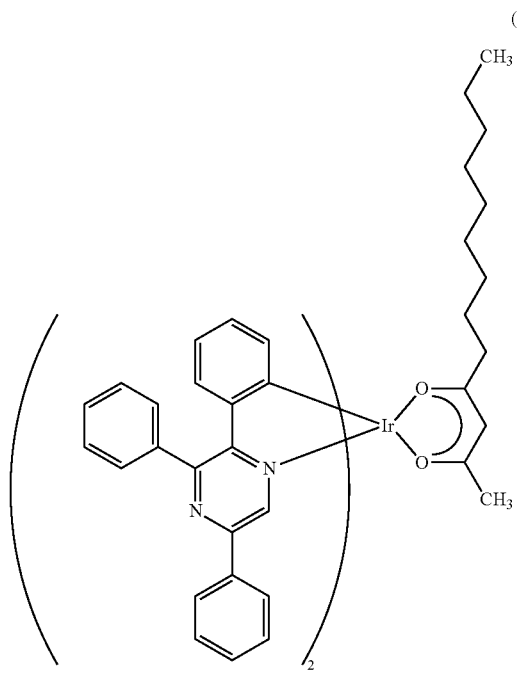
(157)
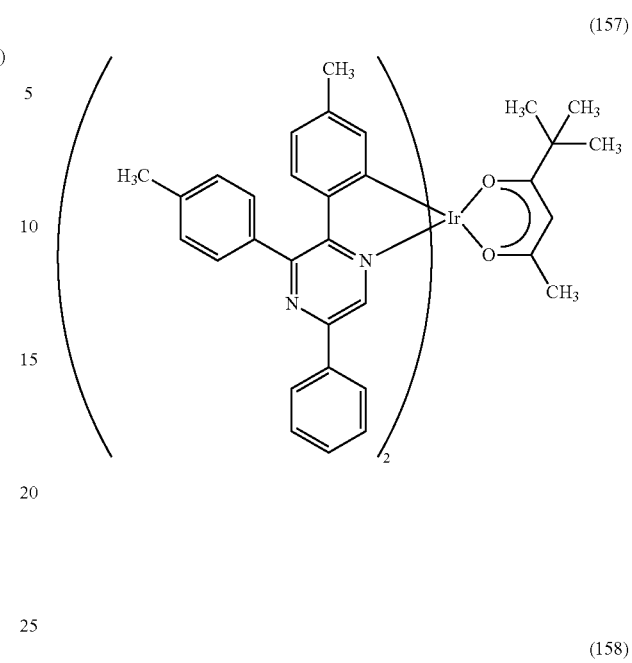
(155)
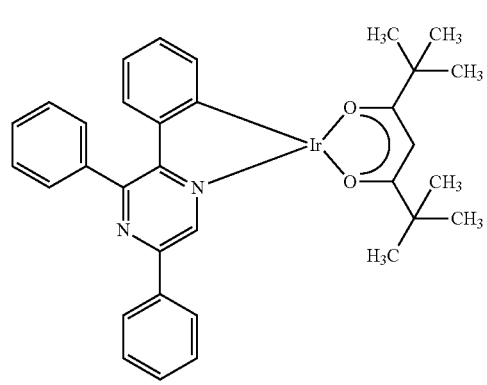
(158)
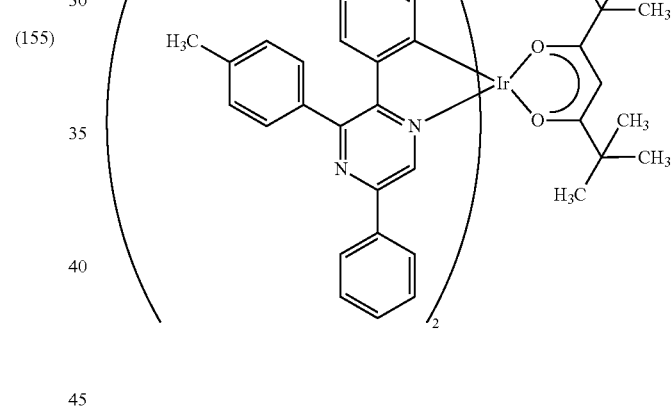
(156)
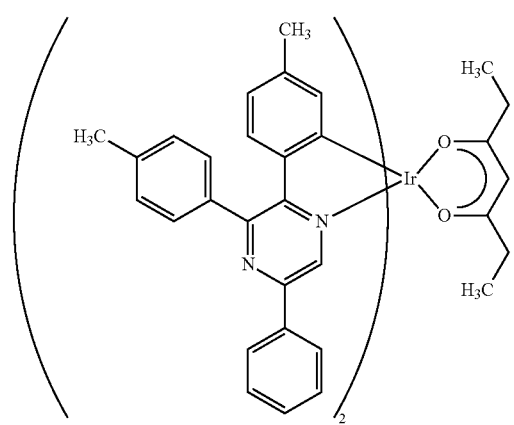
(159)
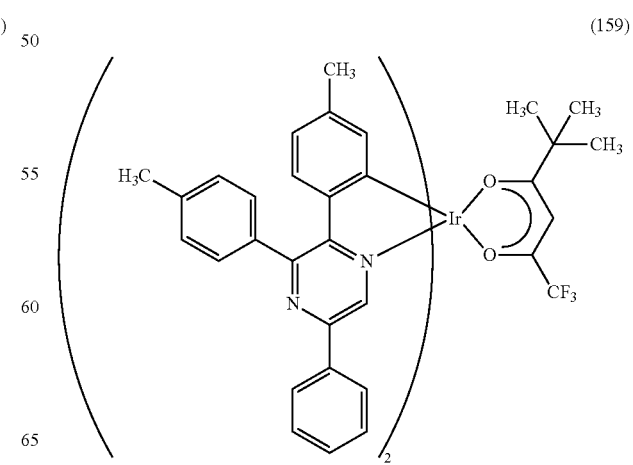

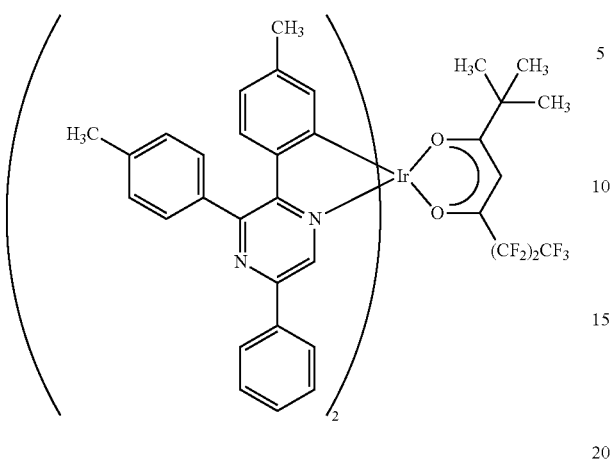
(160)
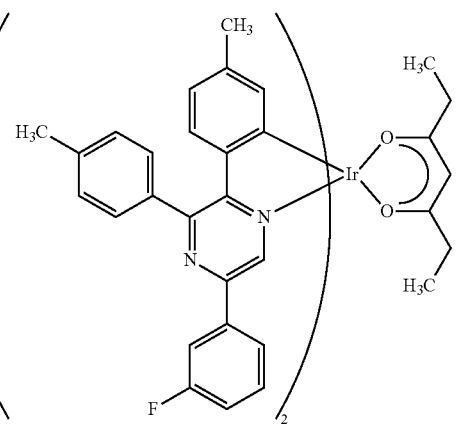
(163)
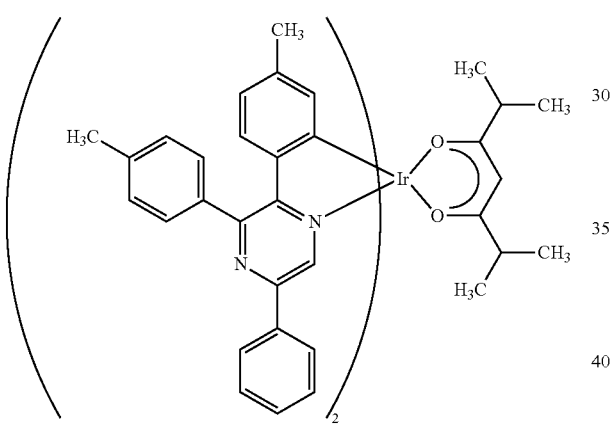
(161)
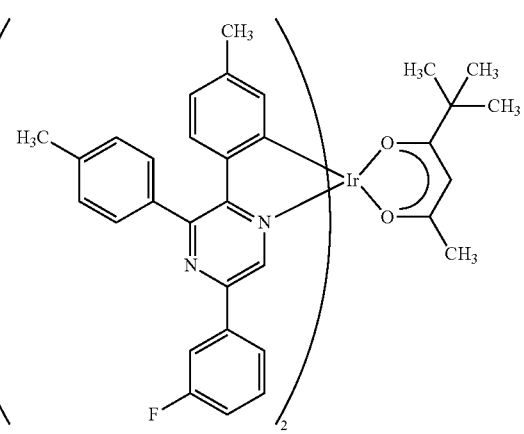
(164)
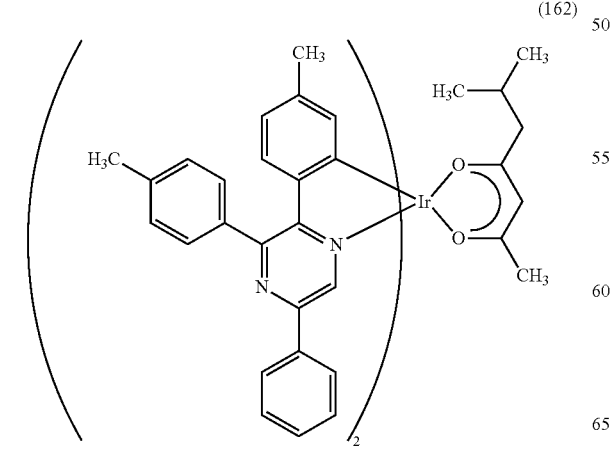
(162)
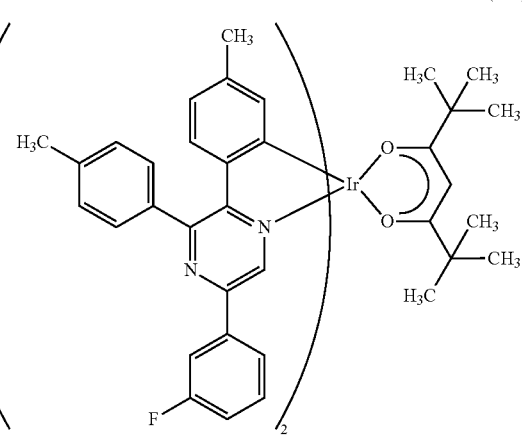
(165)

(166)
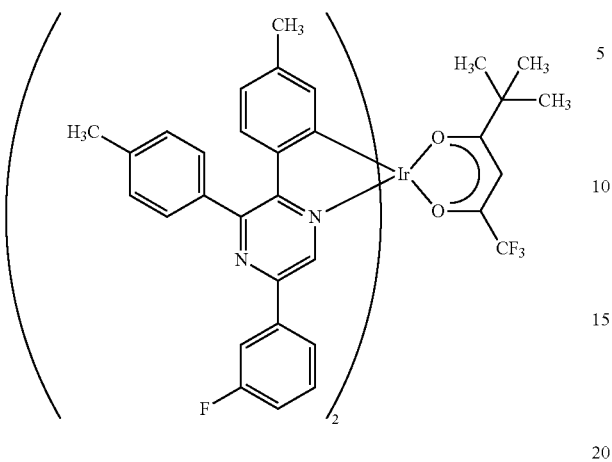
(167)
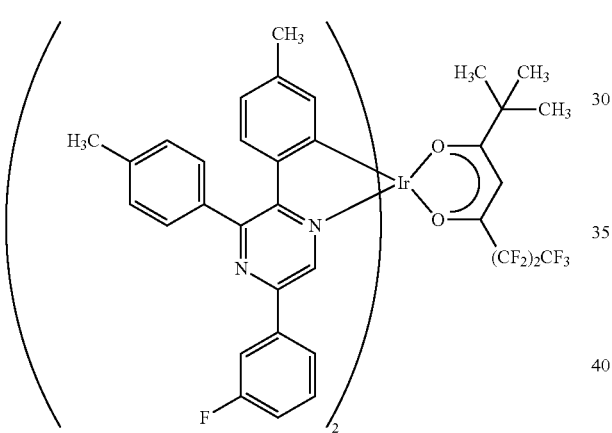
(168)
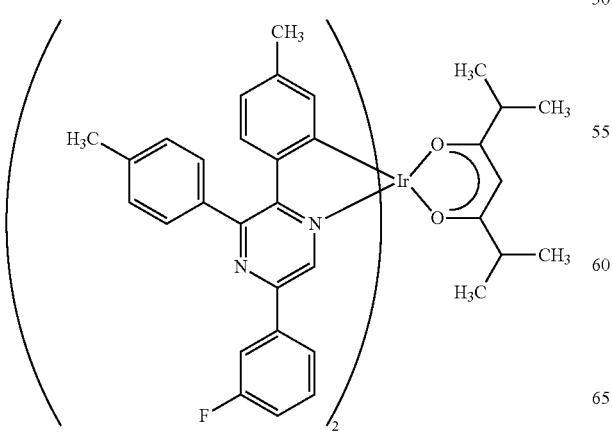
(169)
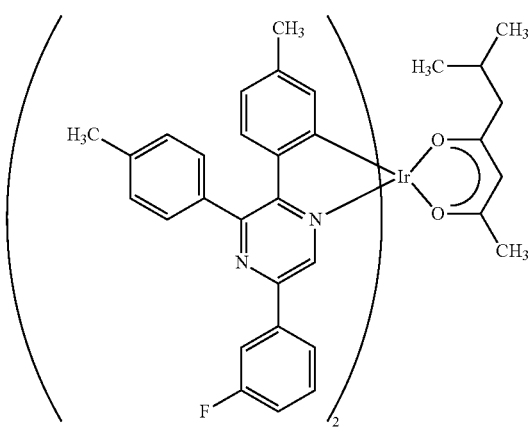
(170)
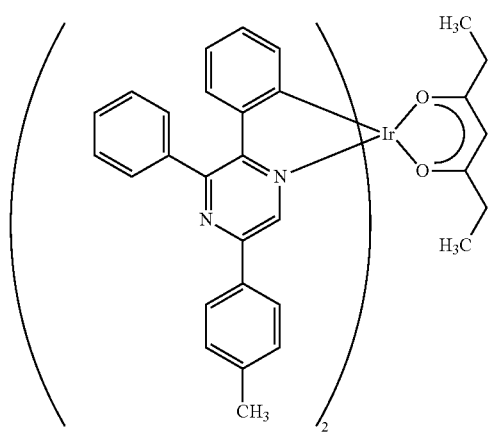
(171)
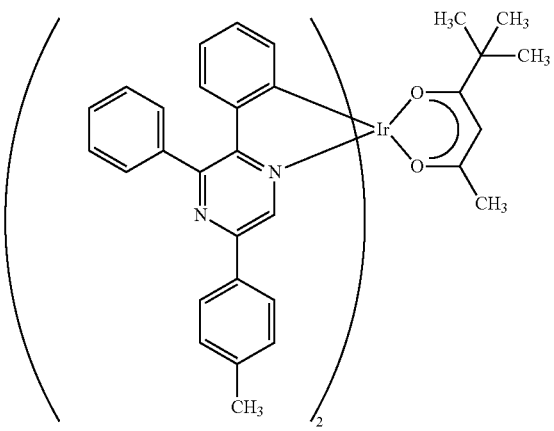

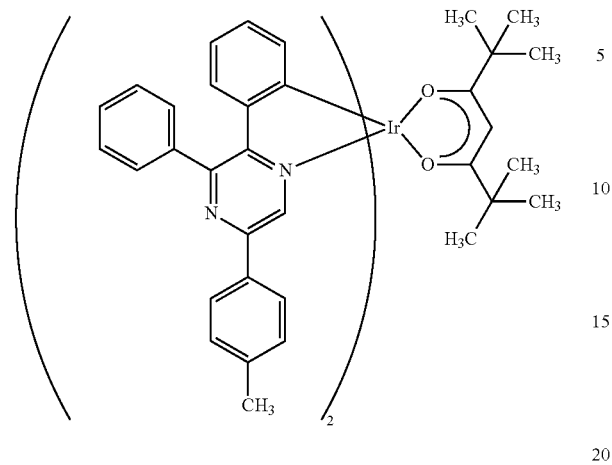
(172)
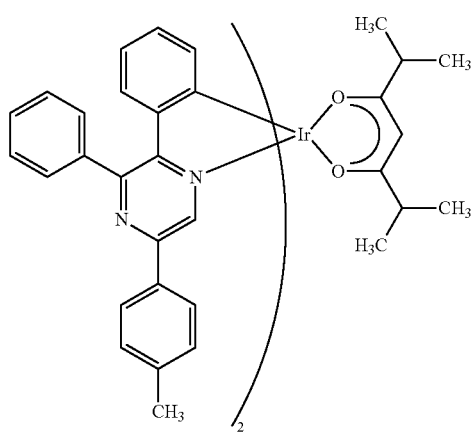
(175)
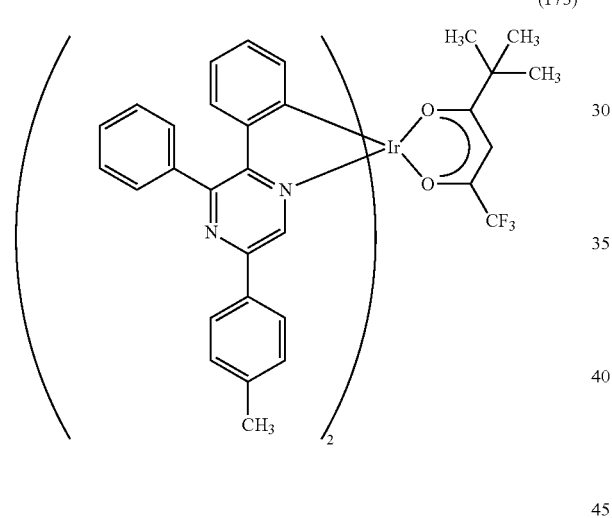
(173)
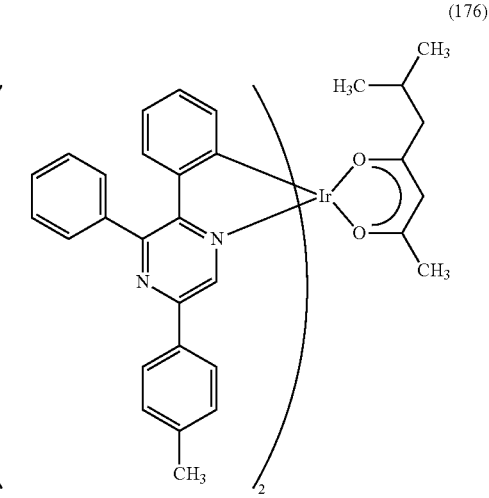
(176)
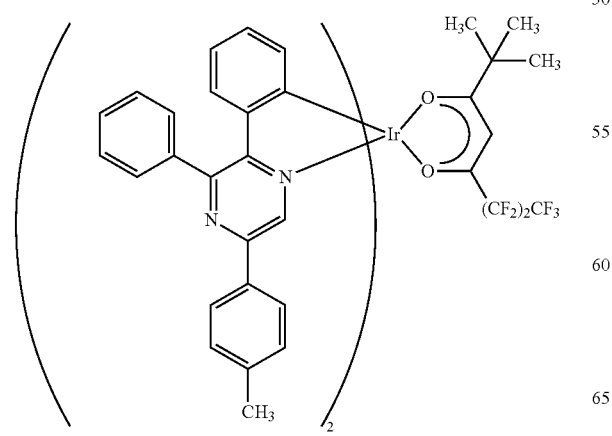
(174)
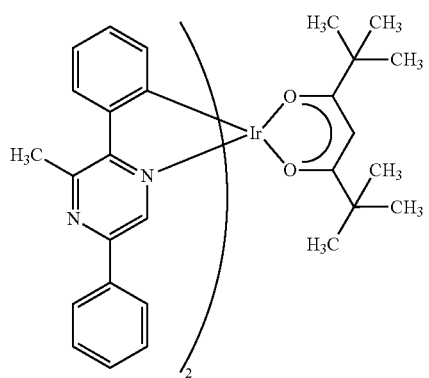
(177)

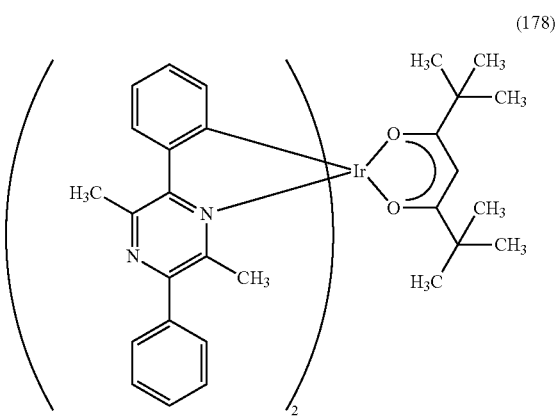

(178)

Various reactions can be applied to a synthetic method for an organometallic complex of the present invention. For example, a derivative of an organometallic complex of the present invention can be synthesized by a synthesis reaction described below. Note that a synthetic method for forming an organometallic complex of the present invention is not limited to the synthetic methods below.

<<A Synthetic Method for a Pyrazine Derivative Represented by the General Formula (G0)>>

An organometallic complex of the present invention is formed through orthometallation of a pyrazine derivative represented by the general formula (G0) with an ion of a metal element belonging to Group 9 or Group 10.

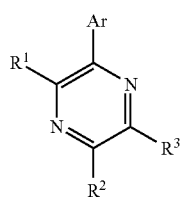

(G0)

A pyrazine derivative represented by the general formula (G0) can be synthesized by a simple synthetic scheme such as the one given below. For example, as shown in a following scheme (a), a halide of arene (A1) is lithiated with alkyl lithium or the like, and is reacted with pyrazine (A2), whereby a pyrazine derivative represented by the general formula (G0) is obtained. Alternatively, as shown in a following scheme (a1), a pyrazine derivative represented by the general formula (G0) can be obtained by coupling a boronic acid of arene (A1-1) and a halide of pyrazine (A2-1). Further alternatively, as shown in a following scheme (a2), a pyrazine derivative represented by the general formula (G0) can be obtained by reaction of diketone of arene (A1-2) and diamine (A2-2). Further alternatively, as shown in a following scheme (a3), a pyrazine derivative represented by the general formula (G0) can be obtained by reaction of pyrazine of arene (A1-3) and a lithio derivative or a Grignard reagent (A2-3). Note that X in those synthetic schemes represents a halogen element.

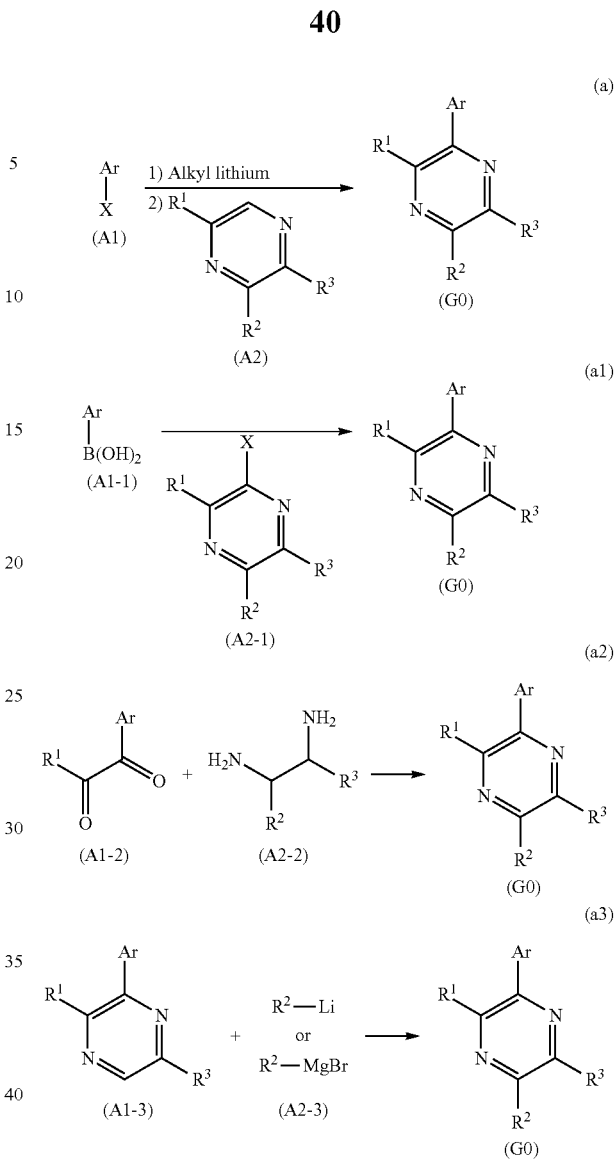

Since various kinds of the above-described compounds (A1), (A2), (A1-1), (A2-1), (A2-2), (A1-3), and (A2-3) are available commercially or can be synthesized, many kinds of a pyrazine derivative represented by the general formula (G0) can be synthesized. Accordingly, an organometallic complex of the present invention has wide variations of ligands.

<<A Synthetic Method for an Organometallic Complex of the Present Invention which is Represented by the General Formula (G1)>>

Next, an organometallic complex of the present invention which is formed through orthometallation of a pyrazine derivative represented by the general formula (G0), i.e., an organometallic complex represented by the following general formula (G1) is described.

First, as shown in a following synthesis scheme (b), a pyrazine derivative represented by the general formula (G0) and a compound of a metal belonging to Group 9 or Group 10 which includes a halogen (such as a metal halide or a metal complex) are heated in an appropriate solvent to obtain a binuclear complex (B). As the solvent, water, alcohols (glycerol, ethylene glycol, 2-ethoxyethanol, 2-methoxyethanol, or the like), ethers (dioxane, anisole, or the like), or the like can be used alone or two or more kinds of them can be mixed and used. A compound of a metal belonging to Group 9 or Group 10 which includes a halogen can be, but not exclusively, rhodium chloride hydrate, palladium chloride, iridium chloride hydrate, iridium chloride hydrate hydrochloride, potassium tetrachloroplatinate(II), or the like. Note that in the synthesis scheme (b), M represents an element belonging to Group 9 or Group 10 and X represents a halogen element. In addition, n is 2 when M is an element belonging to Group 9, and n is 1 when M is an element belonging to Group 10.

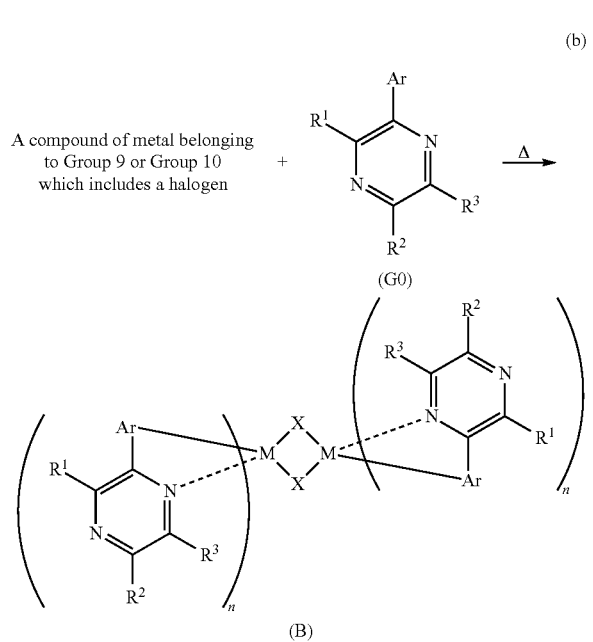

Then, as shown in a following synthesis scheme (c), the binuclear complex (B) and a ligand represented by the general formula (L0) having a β diketone structure are heated in an appropriate solvent in the presence of a base to obtain an organometallic complex of the present invention which is represented by the general formula (G1). As the solvent, water, alcohols (glycerol, ethylene glycol, 2-ethoxyethanol, 2-methoxyethanol, or the like), ethers (dioxane, anisole, or the like), or the like can be used alone or two or more kinds of them can be mixed and used. Note that in the synthesis scheme (c), M represents an element belonging to Group 9 or Group 10 and X represents a halogen element. In addition, n is 2 when M is an element belonging to Group 9, and n is 1 when M is an element belonging to Group 10.

A composition including an organometallic complex of the present invention is also included in the scope of the present invention. Therefore, a composition of the present invention refers to a composition including the above-described organometallic complex and a solvent.

Various kinds of solvents can be used in the above-described composition. For example, the above-described organometallic complex is soluble in a solvent having an aromatic ring (e.g., a benzene ring), such as toluene, xylene, or methoxybenzene (anisole). Further, the above-described organometallic complex is soluble in an organic solvent not including an aromatic ring, such as dimethylsulfoxide (DMSO), dimethylformamide (DMF), or chloroform.

In addition, the above-described organometallic complex is soluble in ether such as diethyl ether or dioxane; or alcohol such as methanol, ethanol, isopropanol, butanol, 2-methoxyethanol, or 2-ethoxyethanol. A composition including alcohol as a solvent has a great advantage when being used for manufacturing a light emitting element, in that EL layers of a light emitting element can be stacked. In other words, a layer can be formed using a composition which includes alcohol as a solvent over a layer including an organic compound which is formed by an evaporation method or the like.

Note that in consideration of using the above-described composition for manufacturing a light emitting element, it is preferable that the organometallic complex be dissolved in a solvent at a concentration of equal to or higher than 0.6 g/L, more preferably, the concentration be equal to or higher than 0.9 g/L.

In addition, it is preferable that the solvent be an organic solvent having a boiling point of equal to or greater than 50° C. and equal to or less than 200° C. because the solvent needs to be removed for film formation, in consideration of using the above-described composition for manufacturing a light emitting element.

In addition, in consideration of using the composition for manufacturing a light emitting element, it is preferable that the composition described in this embodiment mode further include an organic semiconductor material. As the organic semiconductor material, an aromatic compound or a heteroaromatic compound which is solid at room temperature can be used. Although a low molecular compound or a high molecular compound can be used as the organic semiconductor material, a high molecular compound is particularly preferable in terms of the quality of a film which is formed.

When a low molecular compound is used, a low molecular compound (which may be referred to as a medium molecular compound) including a substituent which can increase the solubility in a solvent is preferably used.

Specific examples of the organic semiconductor material are listed below. Examples of an organic semiconductor material having a hole-transporting property, which can be used, are a low molecular compound such as 4,4'-bis[N-(1-naphthyl)-N-phenylamino]biphenyl (abbr.: NPB), 4,4'-bis[N-(9-phenanthryl)-N-phenylamino]biphenyl (abbr.: PPB), 4,4'-bis[N-(3-methylphenyl)-N-phenylamino]biphenyl (abbr.: TPD), 4,4'-bis[N-(9,9-dimethylfluoren-2-yl)-N-phenylamino]biphenyl (abbr.: DFLDPBi), 4,4',4"-tris(N,N-diphenylamino)triphenylamine (abbr.: TDATA), 4,4',4"-tris[N-(3-methylphenyl)-N-phenylamino]triphenylamine (abbr.: m-MTDATA), 4,4',4"-tri(N-carbazolyl)triphenylamine (abbr.: TCTA), 1,1-bis[4-(diphenylamino)phenyl]cyclohexane (abbr.: TPAC), 9,9-bis[4-(diphenylamino)phenyl]fluorene (abbr.: TPAF), N-[4-(9-carbazolyl)phenyl]-N-phenyl-9,9-dimethylfluoren-2-amine (abbr.: YGAF), 4,4'-di(N-carbazolyl)biphenyl (abbr.: CBP), 1,3-bis(N-carbazolyl)benzene (abbr.: mCP), or 1,3,5-tris(N-carbazolyl)benzene (abbr.: TCzB); and a high molecular compound such as poly(4-vinyltriphenylamine) (abbr.: PVTPA) or poly(N-vinylcarbazole) (abbr.: PVK). As an organic semiconductor material having an electron-transporting property, a low molecular compound such as 9-[4-(5-phenyl-1,3,4-oxadiazol-2-yl)phenyl]carbazole (abbr.: CO11), 1,3-bis[5-(p-tert-butylphenyl)-1,3,4-oxadiazol-2-yl]benzene (abbr.: OXD-7), 2-(4-biphenylyl)-5-(4-tert-butylphenyl)-1,3,4-oxadiazole (abbr.: PBD), 2,2',2"-(1,3,5-benzenetriyl)tris(1-phenyl-1H-benzimidazole) (abbr.: TPBI), 3-(4-tert-butylphenyl)-4-phenyl-5-(4-biphenylyl)-1,2,4-triazole (abbr.: TAZ01), 3-(4-tert-butylphenyl)-4-(4-ethylphenyl)-5-(4-biphenylyl)-1,2,4-triazole (abbr.: p-EtTAZ), 9,9',9"-[1,3,5-triazine-2,4,6-triyl]tricarbazole (abbr.: TCzTRZ), 2,2',2"-(1,3,5-benzenetriyl)tris(6,7-dimethyl-3-phenylquinoxaline) (abbr.: TriMeQn), 9,9'-(quinoxaline-2,3-diyldi-4,1-phenylene)di(9H-carbazole) (abbr.: CzQn), 3,3',6,6'-tetraphenyl-9,9'-(quinoxaline-2,3-diyldi-4,1-phenylene)di(9H-carbazole) (abbr.: DCzPQ), bathophenanthroline (abbr.: BPhen), bathocuproine (abbr.: BCP), bis(2-methyl-8-quinolinolato)(4-phenylphenolato)aluminum(III) (abbr.: BAlq), tris[2-(2-hydroxyphenyl)-5-phenyl-1,3,4-oxadiazolato]aluminum(III) (abbr.: Al(OXD)$_3$), tris(2-hydroxyphenyl-1-phenyl-1H-benzimidazolato)aluminum(II) (abbr.: Al(BIZ)$_3$), bis[2-(2-hydroxyphenyl)benzothiazolato]zinc(II) (abbr.: Zn(BTZ)$_2$), or bis[2-(2-hydroxyphenyl)benzoxazolato]zinc(II) (abbr.: Zn(PBO)$_2$); poly(2,5-pyridine-diyl) (abbr.: PPy); or a metal complex high molecular compound disclosed in the following reference can be used (reference: X. T. TAO et al.; Applied Physics Letters, vol. 70, No. 12, 24 Mar. 1997, pages 1503-1505).

The composition may further include a binder in order to improve the quality of a film which is formed. A high molecular compound that is electrically inactive is preferably used as the binder. Specifically, polymethylmethacrylate (abbr.: PMMA), polyimide, or the like can be used.

The composition described in this embodiment mode includes an organometallic complex which is dissolved and is preferably used for manufacturing a light emitting element. The composition has an organometallic complex dissolved at a sufficiently high concentration for forming a film including the organometallic complex, and thus the composition is preferably used especially for manufacturing a light emitting element.

In addition, the composition described in this embodiment mode includes an organometallic complex including a pyrazine skeleton, which is capable of highly efficient light emission. Thus, the composition is suitable for manufacturing a light emitting element having excellent characteristics.

When a composition including alcohol as a solvent is used in manufacturing a light emitting element, EL layers of the light emitting element can be stacked. In other words, a layer can be further formed using a composition which includes alcohol as a solvent over a layer including an organic compound which is formed by an evaporation method or the like. Thus, light emitting elements having excellent characteristics can be manufactured.

Embodiment Mode 2

One mode of a light emitting element using an organometallic complex of the present invention or a composition of the present invention, and a method for manufacturing the light emitting element is described below with reference to FIG. 1.

Note that in this specification, composite refers not only to a simple mixture of two kinds of materials, but also to a mixture of plural materials in which charges are given and received between materials.

A light emitting element of the present invention includes a plurality of layers between a pair of electrodes. The plurality of layers are stacked layers of a substance having a high carrier-injecting property and of a substance having a high carrier-transporting property. Those layers are stacked so that a light emitting region is formed away from the electrodes. That is, they are stacked so that carriers are recombined in an area away from the electrodes.

In FIG. 1, a substrate 100 is used as a support base of a light emitting element. For example, glass, plastic, or the like may be used as the substrate 100. Any material other than those may be used as long as the material serves as a support base of the light emitting element.

In this embodiment mode, the light emitting element includes a first electrode 101, a second electrode 102, and an EL layer 103 between the first electrode 101 and the second electrode 102. In this embodiment mode, the following description is made assuming that the first electrode 101 serves as an anode and the second electrode 102 serves as a cathode. In other words, in the description below, it is assumed that light is emitted when voltage is applied to the first electrode 101 and the second electrode 102 in a manner such that the potential of the first electrode 101 is higher than that of the second electrode 102.

It is preferable that the first electrode 101 be formed using a metal, an alloy, or a conductive compound with a high work function (specifically, equal to or greater than 4.0 eV), a mixture thereof, or the like. Specifically, indium tin oxide (ITO), indium tin oxide containing silicon or silicon oxide, indium zinc oxide (IZO), indium oxide containing tungsten oxide and zinc oxide (IWZO), or the like can be used. A film of such conductive metal oxide is typically formed by sputtering, but may be formed by application of a sol-gel process or the like. For example, a film of indium zinc oxide (IZO) can be formed by a sputtering method using a target in which zinc oxide is added to indium oxide at 1 to 20 wt %. A film of indium oxide containing tungsten oxide and zinc oxide (IWZO) can be formed by a sputtering method using a target in which tungsten oxide and zinc oxide are added to indium oxide at 0.5 to 5 wt % and 0.1 to 1 wt %, respectively. Further, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used.

When a layer including a composite material which is described later is used as a layer in contact with the first electrode 101, the first electrode 101 can be formed using any of a variety of metals, alloys, conductive compounds, a mixture thereof, or the like regardless of their work function. For example, aluminum (Al), silver (Ag), an aluminum alloy (AlSi), or the like can be used. Alternatively, an element belonging to Group 1 or Group 2 of the periodic table, which is a low-work function material, that is, an alkali metal such as lithium (Li) or cesium (Cs), an alkaline earth metal such as magnesium (Mg), calcium (Ca), or strontium (Sr), or an alloy thereof (MgAg or AlLi); a rare earth metal such as europium (Eu) or ytterbium (Yb), or an alloy thereof; or the like can be used. A film including an alkali metal, an alkaline earth metal, or an alloy thereof can be formed by a vacuum evaporation method. Alternatively, a film including an alloy of an alkali metal or an alkaline earth metal can be formed by a sputtering method. Further alternatively, the film can be formed using a silver paste or the like by a droplet discharge method or the like.

There is no particular limitation on a stacked structure of the EL layer 103. It is acceptable as long as the EL layer 103 is formed of appropriate combination including the light emitting layer described in this embodiment mode and a layer including a substance having a high electron-transporting property, a substance having a high hole-transporting property, a substance having a high electron-injecting property, a substance having a high hole-injecting property, a bipolar substance (a substance having a high electron-transporting and hole-transporting property), or the like. For example, appropriate combination of a hole-injecting layer, a hole-transporting layer, a light emitting layer, an electron-transporting layer, an electron-injecting layer, and the like can be employed. Examples of materials for those layers are described below.

A hole-injecting layer 111 is a layer including a substance having a high hole-injecting property. As a substance having a high hole-injecting property, molybdenum oxide, vanadium oxide, ruthenium oxide, tungsten oxide, manganese oxide, or the like can be used. Alternatively, the hole-injecting layer 111 can be formed of a phthalocyanine-based compound such as phthalocyanine (abbr.: H$_2$Pc) or copper phthalocyanine (abbr.: CuPc), a high molecular compound such as poly(3,4-ethylenedioxythiophene)/poly(styrenesulfonic acid) (PEDOT/PSS), or the like.

Alternatively, the hole-injecting layer 111 can be formed using a composite material in which an acceptor substance is mixed into a substance having a high hole-transporting property. Note that a material for forming the electrode can be selected regardless of its work function if the composite material in which an acceptor substance is mixed into a substance having a high hole-transporting property is used. In other words, not only a high-work function material, but also a low-work function material can be used for the first electrode 101. Examples of the acceptor substance are 7,7,8,8-tetracyano-2,3,5,6-tetrafluoroquinodimethane (abbr.: F$_4$-TCNQ), chloranil, transition metal oxide, and oxide of a metal belonging to Group 4 to Group 8 of the periodic table. Specifically, vanadium oxide, niobium oxide, tantalum oxide, chromium oxide, molybdenum oxide, tungsten oxide, manganese oxide, and rhenium oxide are preferably used because of their high electron-accepting property. In particular, molybdenum oxide is preferable because of its stability in the atmosphere, low hygroscopic property, and easiness of handling.

As the substance having a high hole-transporting property which is used for the composite material, any of a variety of compounds such as an aromatic amine compound, a carbazole derivative, aromatic hydrocarbon, or a high molecular compound (e.g., an oligomer, a dendrimer, or a polymer) can be used. A substance having a hole mobility of equal to or greater than $10^{-6}$ cm$^2$/Vs is preferably used as the substance having a high hole-transporting property which is used for the composite material. Note that any substance other than the above substances may be used as long as it is a substance in which the hole-transporting property is higher than the electron-transporting property. Organic compounds that can be used for the composite material are specifically listed below.

Examples of the aromatic amine compound which can be used for the composite material are N,N'-bis(4-methylphenyl)(p-tolyl)-N,N'-diphenyl-p-phenylenediamine (abbr.: DTDPPA), 4,4'-bis[N-(4-diphenylaminophenyl)-N-phenylamino]biphenyl (abbr.: DPAB), 4,4'-bis(N-{4-[N'-(3-methylphenyl)-N'-phenylamino]phenyl}-N-phenylamino)biphenyl (abbr.: DNTPD), 1,3,5-tris[N-(4-diphenylaminophenyl)-N-phenylamino]benzene (abbr.: DPA3B), and the like.

Examples of the carbazole derivative which can be used for the composite material are 3-[N-(9-phenylcarbazol-3-yl)-N-phenylamino]-9-phenylcarbazole (abbr.: PCzPCA1), 3,6-bis[N-(9-phenylcarbazol-3-yl)-N-phenylamino]-9-phenylcarbazole (abbr.: PCzPCA2), 3-[N-(1-naphtyl)-N-(9-phenylcarbazol-3-yl)amino]-9-phenylcarbazole (abbr.: PCzPCN1), and the like.

Examples of the carbazole derivative which can be used for the composite material are 4,4'-di(N-carbazolyl)biphenyl (abbr.: CBP), 1,3,5-tris[4-(N-carbazolyl)phenyl]benzene (abbr.: TCPB), 9-[4-(10-phenyl-9-anthryl)phenyl]-9H-carbazole (abbr.: CzPA), 1,4-bis[4-(N-carbazolyl)phenyl]-2,3,5,6-tetraphenylbenzene, and the like.

Examples of the aromatic hydrocarbon which can be used for the composite material are 2-tert-butyl-9,10-di(2-naphthyl)anthracene (abbr.: t-BuDNA), 2-tert-butyl-9,10-di(1-naphthyl)anthracene, 9,10-bis(3,5-diphenylphenyl)anthracene (abbr.: DPPA), 2-tert-butyl-9,10-bis(4-phenylphenyl)anthracene (abbr.: t-BuDBA), 9,10-di(2-naphthyl)anthracene (abbr.: DNA), 9,10-diphenylanthracene (abbr.: DPAnth), 2-tert-butylanthracene (abbr.: t-BuAnth), 9,10-bis(4-methyl-1-naphthyl)anthracene (abbr.: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Further, pentacene, coronene, or the like can be used. Thus, an aromatic hydrocarbon having a hole mobility of equal to or greater than $1\times10^{-6}$ cm$^2$/Vs and having 14 to 42 carbon atoms is preferable.

Note that the aromatic hydrocarbon which can be used for the composite material may have a vinyl skeleton. Examples of the aromatic hydrocarbon having a vinyl skeleton are 4,4'-bis(2,2-diphenylvinyl)biphenyl (abbr.: DPVBi) 9,10-bis[4-(2,2-diphenylvinyl)phenyl]anthracene (abbr.: DPVPA), and the like.

For the hole-injecting layer 111, a high molecular compound (an oligomer, a dendrimer, or a polymer) can be used. For example, a high molecular compound such as poly(N-vinylcarbazole) (abbr.: PVK), poly(4-vinyltriphenylamine) (abbr.: PVTPA), poly[N-(4-{N'-[4-(4-diphenylamino)phenyl]phenyl-N'-phenylamino}phenyl)methacrylamide] (abbr.: PTPDMA), or poly[N,N'-bis(4-butylphenyl)-N,N'-bis(phenyl)benzidine] (abbr.: Poly-TPD) can be used. Alternatively, a high molecular compound mixed with acid, such as poly(3,4-ethylenedioxythiophene)/poly(styrenesulfonic acid) (PEDOT/PSS) or polyaniline/poly(styrenesulfonic acid) (PAni/PSS) can be used.

Note that the hole-injecting layer 111 can be formed using a composite material of the above-described high molecular compound, such as PVK, PVTPA, PTPDMA, or Poly-TPD, and the above-described acceptor substance.

A hole-transporting layer 112 includes a substance having a high hole-transporting property. An example of the substance having a high hole-transporting property is an aromatic amine compound such as 4,4'-bis[N-(1-naphthyl)-N-phenylamino]biphenyl (abbr.: NPB or α-NPB), N,N'-bis(3-methylphenyl)-N,N'-diphenyl-[1,1'-biphenyl]-4,4'-diamine (abbr.: TPD), 4,4',4''-tris(N,N-diphenylamino)triphenylamine (abbr.: TDATA), 4,4',4''-tris[N-(3-methylphenyl)-N-phenylamino]triphenylamine (abbr.: MTDATA), or 4,4'-bis[N-(spiro-9,9'-bifluoren-2-yl)-N-phenylamino]biphenyl (abbr.: BSPB). Most of these substances mentioned here have a hole mobility of equal to or greater than $10^{-6}$ cm$^2$/Vs. Note that any substance other than the above-mentioned substances may also be used as long as it is a substance in which the hole-transporting property is higher than the electron-transporting property. The layer including a substance having a high hole-transporting property is not limited to a single layer, and may be a stack of two or more layers each including the above-mentioned substance.

For the hole-transporting layer 112, a high molecular compound such as PVK, PVTPA, PTPDMA, or Poly-TPD can be used alternatively.

A light emitting layer 113 includes a substance having a high light emitting property. An organometallic complex of the present invention which is described in Embodiment Mode 1 can be used as the substance having a high light emitting property. An organometallic complex of the present invention can be preferably used as a light emitting substance of a light emitting element because of its high light emission efficiency.

In the light emitting layer 113, a structure in which an organometallic complex of the present invention is dispersed in a host material is particularly preferable. As the host material, an organic semiconductor material having a hole-transporting property mentioned in Embodiment Mode 1 (e.g., NPB, PPB, TPD, DFLDPBi, TDATA, m-MTDATA, TCTA, TPAC, TPAF, YGAF, CBP, mCP, TCzB, PVTPA, or PVK); an organic semiconductor material having an electron-transporting property (e.g., CO11, OXD-7, PBD, TPBI, TAZ01, p-EtTAZ, TCzTRZ, TriMeQn, CzQn, DCzPQ, BPhen, BCP, BAlq, Al(OXD)$_3$, Al(BIZ)$_3$, Zn(BTZ)$_2$, Zn(PBO)$_2$, or PPy); or a metal complex high molecular compound disclosed in the following reference (reference: X. T. TAO et al., Applied Physics Letters, vol. 70, No. 12, 24 Mar. 1997, pages 1503-1505); or the like can be used. Further, it is preferable that both an organic semiconductor material having a hole-transporting property and an organic semiconductor material having an electron-transporting property, which are mentioned above, be used as a host material, in order to improve the lifetime of an element.

The light emitting layer 113 can be formed by various methods, whether it is a dry process or a wet process. For example, the light emitting layer 113 can be formed by an evaporation method, which is a dry process. Alternatively, the light emitting layer 113 can be formed by a wet process using a composition including an organometallic complex of the present invention which is described in Embodiment Mode 1. Specifically, the composition described in Embodiment Mode 1 may be applied by a droplet discharge method, a spin coating method, or the like, and then, the solvent may be removed. A heat treatment, a low pressure treatment, a heat treatment under low pressure, or the like is employed for removing the solvent.

Here, it is preferable that the solvent included in the composition be alcohol for the following reason. Low molecular compounds which are used for light emitting elements are generally difficult to be dissolved in alcohol. Therefore, when the solvent included in the composition is alcohol, even if a layer including a low molecular compound which is formed by an evaporation method or the like is formed before formation of a light emitting layer, the light emitting layer can be stacked thereon by application of the composition by a wet process.

An electron-transporting layer 114 includes a substance having a high electron-transporting property. For example, the electron-transporting layer 114 can be formed using a metal complex or the like having a quinoline or benzoquinoline skeleton, such as tris(8-quinolinolato)aluminum (abbr.: Alq), tris(4-methyl-8-quinolinolato)aluminum (abbr.: Almq$_3$), bis(10-hydroxybenzo[h]quinolinato)beryllium (abbr.: BeBq$_2$), or bis(2-methyl-8-quinolinolato)(4-phenylphenolato)aluminum (abbr.: BAlq). Alternatively, a metal complex or the like having an oxazole-based or thiazole-based ligand, such as bis[2-(2-hydroxyphenyl)benzoxazolato]zinc (abbr.: Zn(BOX)$_2$) or bis[2-(2-hydroxyphenyl)benzothiazolato]zinc (abbr.: Zn(BTZ)$_2$) can be used. As an alternative to the metal complex, 2-(4-biphenylyl)-5-(4-tert-butylphenyl)-1,3,4-oxadiazole (abbr.: PBD), 1,3-bis[5-(p-tert-butylphenyl)-1,3,4-oxadiazol-2-yl]benzene (abbr.: OXD-7), 3-(4-biphenylyl)-4-phenyl-5-(4-tert-butylphenyl)-1,2,4-triazole (abbr.: TAZ), bathophenanthroline (abbr.: BPhen), bathocuproine (abbr.: BCP), or the like can be used. Most of these substances mentioned here have an electron mobility of equal to or greater than $10^{-6}$ cm$^2$/Vs. Note that any substance other than the above substances may be used as long as it is a substance in which the electron-transporting property is higher than the hole-transporting property. The electron-transporting layer is not limited to a single layer, and may be a stack of two or more layers each including the above-mentioned substance.

Further, a high molecular compound such as poly[(9,9-dihexylfluorene-2,7-diyl)-co-(pyridine-3,5-diyl)] (abbr.: PF-Py) or poly[(9,9-dioctylfluorene-2,7-diyl)-co-(2,2'-bipyridine-6,6'-diyl)] (abbr.: PF-BPy) can be used for the electron-transporting layer 114.

An electron-injecting layer 115 may be provided. The electron-injecting layer 115 can be formed using an alkali metal compound or an alkaline earth metal compound such as lithium fluoride (LiF), cesium fluoride (CsF), or calcium fluoride (CaF$_2$). Further, a layer, in which a substance having an electron-transporting property and an alkali metal or an alkaline earth metal are combined can be employed as the electron-injecting layer 115. For example, a layer of Alq in which magnesium (Mg) is included can be used. Note that it is more preferable to use a layer in which a substance having an electron-transporting property and an alkali metal or an alkaline earth metal are combined as the electron-injecting layer, because electrons are injected from the second electrode 102 efficiently.

A substance forming the second electrode 102 can be a metal, an alloy, or a conductive compound, which has a low work function (specifically, equal to or less than 3.8 eV), a mixture thereof, or the like. Specific examples of such cathode materials are an element belonging to Group 1 or Group 2 of the periodic table, that is an alkali metal such as lithium (Li) or cesium (Cs) or an alkaline earth metal such as magnesium (Mg), calcium (Ca), and strontium (Sr); an alloy thereof (e.g., MgAg or AlLi); a rare earth metal such as europium (Eu) or ytterbium (Yb), an alloy thereof; or the like. A film including an alkali metal, an alkaline earth metal, or an alloy thereof can be formed by a vacuum evaporation method. Alternatively, a film of an alkali metal, an alkaline earth metal, or an alloy thereof can be formed by a sputtering method. Further alternatively, a film can be formed using a silver paste or the like by a droplet discharge method or the like.

When the electron-injecting layer 115 is provided between the second electrode 102 and the electron-transporting layer 114, any of a variety of conductive materials such as Al, Ag, ITO, or indium tin oxide containing silicon or silicon oxide can be used for the second electrode 102 regardless of its work function. A film of such a conductive material can be formed by a sputtering method, a droplet discharge method, a spin coating method, or the like.

In the light emitting element having the above-described structure in this embodiment mode, application of voltage between the first electrode 101 and the second electrode 102 makes current flow, whereby holes and electrons are recombined in the light emitting layer 113 including a substance having a high light emitting property and light is emitted. That is, a light emitting region is formed in the light emitting layer 113.

Light which is emitted is extracted outside through either one or both the first electrode 101 and the second electrode 102. Accordingly, either one or both the first electrode 101 and the second electrode 102 are formed of a light-transmissive material. When only the first electrode 101 is a light-transmissive electrode, light is extracted from the substrate side through the first electrode 101. When only the second electrode 102 is a light-transmissive electrode, light is extracted from a side opposite to the substrate side through the second electrode 102. When both of the first electrode 101 and the second electrode 102 are light-transmissive electrodes, light is extracted from both the substrate side and the side opposite to the substrate side through the first electrode 101 and the second electrode 102.

Figure 2:
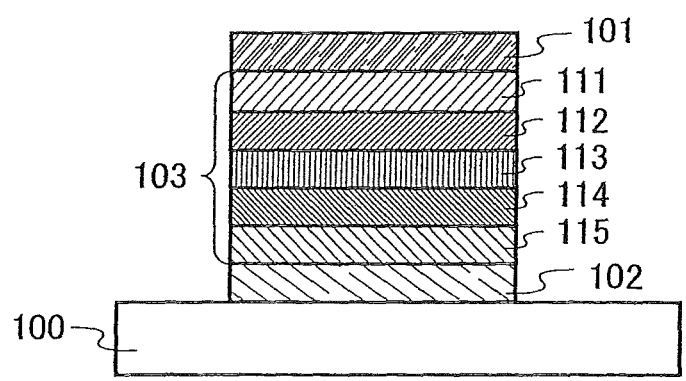
FIG. 2 illustrates a diagram illustrating a light emitting element of the present invention.

Note that while FIG. 1 shows a structure in which the first electrode 101 which serves as an anode is disposed on the substrate 100 side, the second electrode 102 which serves as a cathode may be disposed on the substrate 100 side. FIG. 2 shows a structure in which the second electrode 102 which serves as a cathode, the EL layer 103, and the first electrode 101 which serves as an anode are stacked in that order over the substrate 100. In the EL layer 103, the layers are stacked in the reverse order of the order shown in FIG. 1.

The EL layer can be formed by various methods, whether it is a dry process or a wet process. A film forming method for forming electrodes and layers may be different between the electrodes and layers. A vacuum evaporation method, a sputtering method, or the like can be given as a dry process. A droplet discharge method, a spin coating method, or the like can be given as a wet process.

For example, the EL layer may be formed of a high molecular compound among the above-described materials by a wet process. The EL layer can alternatively be formed of a low molecular compound by a wet process. Further alternatively, the EL layer may be formed of a low molecular organic compound by a dry process such as a vacuum evaporation method.

Although the light emitting layer 113 can be formed by various methods, whether it is a dry process or a wet process, the light emitting layer 113 can be preferably formed of the composition described in Embodiment Mode 1 by a wet process. Specifically, the composition described in Embodiment Mode 1 may be applied by a droplet discharge method, a spin coating method, or the like, and then, the solvent may be removed. A heat treatment, a low pressure treatment, a heat treatment under low pressure, or the like is employed for removing the solvent. The material use efficiency can be improved by employing a wet process, thus the manufacturing cost of light emitting element can be reduced.

The electrodes may also be formed by a wet process such as a sol-gel process or by a wet process using a metal paste. Alternatively, the electrodes may be formed by a dry process such as a sputtering method or a vacuum evaporation method.

When the light emitting element described in this embodiment mode is applied to a display device and the light emitting layer in the light emitting element is selectively formed according to each color, the light emitting layer is preferably formed by a wet process. When the light emitting layer is formed by a droplet discharge method, selective formation of the light emitting layer for each color can be easily performed even in the case of a large substrate, and thus productivity is improved.

A specific method for forming the light emitting element is described below.

For example, the structure shown in FIG. 1 may be obtained by the following steps: forming the first electrode 101 by a sputtering method, which is a dry process; forming the hole-injecting layer 111 by a droplet discharge method or a spin coating method, which is a wet process; forming the hole-transporting layer 112 by a vacuum evaporation method, which is a dry process; forming the light emitting layer 113 by a droplet discharge method, which is a wet process; forming the electron-transporting layer 114 by a vacuum evaporation method, which is a dry process; forming the electron-injecting layer 115 by a vacuum evaporation method, which is a dry process; and forming the second electrode 102 by a droplet discharge method or a spin coating method which is a wet process. Alternatively, the structure shown in FIG. 1 may be obtained by the following steps: forming the first electrode 101 by a droplet discharge method, which is a wet process; forming the hole-injecting layer 111 by a vacuum evaporation method, which is a dry process; forming the hole-transporting layer 112 by a droplet discharge method or a spin coating method, which is a wet process; forming the light emitting layer 113 by a droplet discharge method, which is a wet process; forming the electron-transporting layer 114 by a droplet discharge method or a spin coating method, which is a wet process; forming the electron-injecting layer 115 by a droplet discharge method or a spin coating method, which is a wet process; and forming the second electrode 102 by a droplet discharge method or a spin coating method, which is a wet process. Note that the method is not limited to the above-described methods, and a method in which a wet process and a dry process are combined as appropriate may be employed.

For example, the structure shown in FIG. 1 can be obtained by the following steps: forming the first electrode 101 by a sputtering method, which is a dry process; forming the hole-injecting layer 111 and the hole-transporting layer 112 by a droplet discharge method or a spin coating method, which is a wet process; forming the light emitting layer 113 by a droplet discharge method, which is a wet process;

forming the electron-transporting layer 114 and the electron-injecting layer 115 by a vacuum evaporation method, which is a dry process; and forming the second electrode 102 by a vacuum evaporation method, which is a dry process. In other words, it is possible to form the hole-injecting layer 111 to the light emitting layer 113 by a wet process and to form the electron-transporting layer 114 to the second electrode 102 thereover by a dry process over the substrate provided with the first electrode 101 which has already been formed in a desired shape. By this method, the hole-injecting layer 111 to the light emitting layer 113 can be formed at atmospheric pressure and the light emitting layer 113 can be selectively formed according to each color with ease. In addition, the electron-transporting layer 114 to the second electrode 102 can be successively formed in vacuum. Therefore, the process can be simplified, and productivity can be improved.

The process is exemplarily described below. A film of PEDOT/PSS is formed as the hole-injecting layer 111 over the first electrode 101. Since PEDOT/PSS is soluble in water, a film thereof can be formed using an aqueous solution of PEDOT/PSS by a spin coating method, a droplet discharge method, or the like. The hole-transporting layer 112 is not provided and the light emitting layer 113 is provided over the hole-injecting layer 111. The light emitting layer 113 can be formed by a droplet discharge method, using the composition which is described in Embodiment Mode 1, including a solvent (e.g., toluene, eylene, dodecylbenzene, a mixed solvent of dodecylbenzene and tetralin, ethers, or alcohols) which does not dissolve the hole-injecting layer 111 (PEDOT/PSS) which has already been formed. Next, the electron-transporting layer 114 is formed over the light emitting layer 113. When the electron-transporting layer 114 is formed by a wet process, the electron-transporting layer 114 should be formed using a solvent which does not dissolve the hole-injecting layer 111 and the light emitting layer 113 which have already been formed. In that case, the selection range of solvents is limited; therefore, a dry process is easier. Thus, by successively forming the electron-transporting layer 114 to the second electrode 102 in vacuum by a vacuum evaporation method, which is a dry process, the manufacturing process can be simplified.

Meanwhile, a structure shown in FIG. 2 can be formed in the reverse order of the above-described steps: forming the second electrode 102 by a sputtering method or a vacuum evaporation method, which is a dry process; forming the electron-injecting layer 115 and the electron-transporting layer 114 by a vacuum evaporation method, which is a dry process; forming the light emitting layer 113 by a droplet discharge method, which is a wet process; forming the hole-transporting layer 112 and the hole-injecting layer 111 by a droplet discharge method or a spin coating method, which is a wet process; and forming the first electrode 101 by a droplet discharge method or a spin coating method, which is a wet process. By this method, the second electrode 102 to the electron-transporting layer 114 can be successively formed in vacuum by a dry process, and the light emitting layer 113 to the first electrode 101 can be formed at atmospheric pressure. Therefore, the manufacturing process can be simplified, and productivity can be improved. The composition described in Embodiment Mode 1 can be applied to a layer formed by an evaporation method or the like, which allows the above described manufacturing method.

Note that the light emitting element is formed over a substrate of glass, plastic, or the like in this embodiment mode. When a plurality of such light emitting elements are formed over a substrate, a passive matrix light emitting device can be manufactured. It is possible to form, for example, thin film transistors (TFTs) over a substrate formed of glass, plastic, or the like and form light emitting elements over electrodes that are electrically connected to the TFTs. In that case, an active matrix light emitting device in which drive of the light emitting elements is controlled by TFTs can be manufactured. Note that there is no particular limitation on the structure of TFTs, and either staggered TFTs or inversely staggered TFTs may be employed. In addition, a driver circuit formed over a TFT substrate may include both n-channel and p-channel TFTs or either n-channel or p-channel TFTs. Further, there is no particular limitation on the crystallinity of a semiconductor film which is used for TFTs, and either an amorphous semiconductor film or a crystalline semiconductor film may be used.

Since a light emitting element of the present invention includes an organometallic complex which is capable of efficient light emission, the light emission efficiency is high.

When a light emitting element is formed using the composition described in Embodiment Mode 1, selective formation of the light emitting layer for each color can be easy even in the case of a large substrate, and thus productivity is improved. Accordingly, the method for manufacturing a light emitting element, which is described in this embodiment mode is excellent in mass productivity. Also, the manufacturing cost can be reduced.

Embodiment Mode 3

In this embodiment mode, a mode of a light emitting element in which a plurality of light emitting units according to the present invention are stacked (hereinafter, referred to as a stacked-type element) is described with reference to FIG. 3. This light emitting element is a stacked-type light emitting element including a plurality of light emitting units between a first electrode and a second electrode. This structure of the light emitting unit can be similar to that of the EL layer described in Embodiment Mode 2. In other words, a light emitting element including one light emitting unit is described in Embodiment Mode 2, and a light emitting element including a plurality of light emitting units is described in this embodiment mode.

Figure 3:
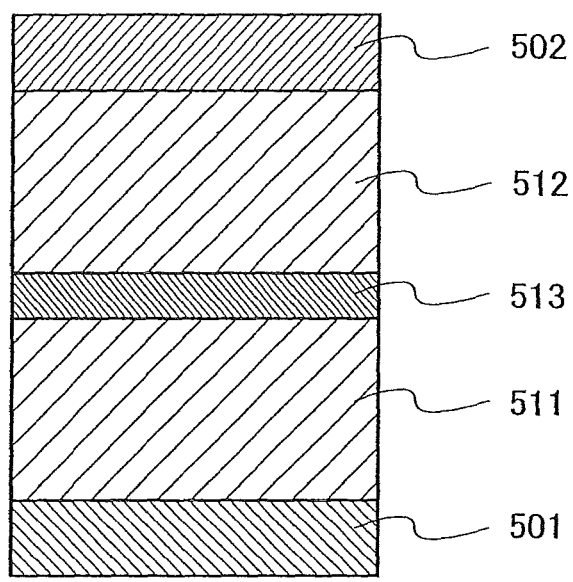
FIG. 3 illustrates a diagram illustrating a light emitting element of the present invention.

In FIG. 3, a first light emitting unit 511, a charge generation layer 513, and a second light emitting unit 512 are stacked between a first electrode 501 and a second electrode 502. The first electrode 501 and the second electrode 502 can be similar to the electrodes in Embodiment Mode 2. The structures of the first light emitting unit 511 and the second light emitting unit 512 may be the same or different. The structure can be similar to that described in Embodiment Mod 2.

The charge generation layer 513 includes a composite material of an organic compound and metal oxide. This composite material of an organic compound and metal oxide has been described in Embodiment Mode 2 and includes an organic compound and metal oxide such as vanadium oxide, molybdenum oxide, or tungsten oxide. As the organic compound, any of a variety of compounds such as an aromatic amine compound, a carbazole derivative, aromatic hydrocarbon, or a high molecular compound (e.g., an oligomer, a dendrimer, or a polymer) can be used. A substance having a hole mobility of equal to or greater than $10^{-6}$ cm$^2$/Vs is preferably used as the organic compound. Note that any substance other than the above substances may be used as long as it is a substance in which the hole-transporting property is higher than the electron-transporting property. The composite material of an organic compound and metal oxide is excellent in carrier-injecting property and carrier-transporting property; therefore, low-voltage driving and low-current driving can be achieved.

Note that the charge generation layer 513 may be formed by combining the composite material of an organic compound and metal oxide and a layer including any other material. For example, the charge generation layer 513 may be formed by a combination of the layer including the composite material of an organic compound and metal oxide with a layer including one compound selected from electron donating substances and a compound having a high electron-transporting property. Alternatively, the charge generation layer 513 may be formed by a combination of a transparent conductive film and a layer including the composite material of an organic compound and metal oxide.

The charge generation layer 513 sandwiched between the first light emitting unit 511 and the second light emitting unit 512 may have any structure as long as electrons can be injected to a light emitting unit on one side and holes can be injected to a light emitting unit on the other side when voltage is applied between the first electrode 501 and the second electrode 502. For example, in FIG. 3, the charge generation layer 513 injects electrons to the first light emitting unit 511 and injects holes to the second light emitting unit 512 when voltage is applied so that the potential of the first electrode is higher than that of the second electrode.

While the light emitting element having two light emitting units is described in this embodiment mode, the present invention can be similarly applied to a light emitting element in which three or more light emitting units are stacked. When a plurality of light emitting units are arranged between a pair of electrodes so that two of the light emitting units are partitioned with a charge generation layer, like the light emitting element according to this embodiment mode, high luminance emission can be realized at a low current density, thus, a long-life light emitting element can be realized. When the light emitting element is applied to a lighting device, voltage drop due to resistance of the electrode materials can be suppressed, and thus uniform light emission over a large area can be realized. Furthermore, a light emitting device which can drive at a low voltage and consumes low power can be achieved.

When emission colors are different between the light emitting units, light emission of a desired color can be obtained from the light emitting element as a whole. For example, when a light emitting element has two light emitting units in which an emission color of the first light emitting unit and an emission color of the second light emitting unit are complementary colors, it is possible to obtain a light emitting element emitting white light as a whole. Note that the complementary colors refer to colors that can produce an achromatic color when they are mixed. That is, white light emission can be obtained by mixture of light from substances, of which the light emission colors are complementary colors. This is similarly applied to a light emitting element having three light emitting units. For example, white light emission can be obtained from the light emitting element as a whole when emission colors of the first, second, and third light emitting units are red, green, and blue, respectively.

This embodiment mode can be combined with any other embodiment mode as appropriate.

Embodiment Mode 4

In this embodiment mode, a light emitting device including a light emitting element of the present invention is described.

Figure 4A:
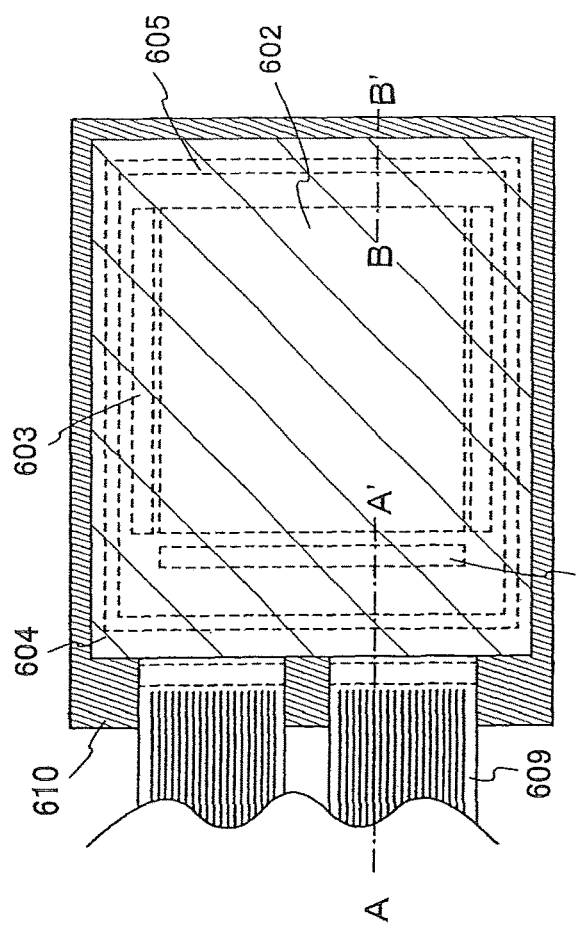
FIGS. 4A and 4B illustrate a light emitting element of the present invention.
Figure 4B:
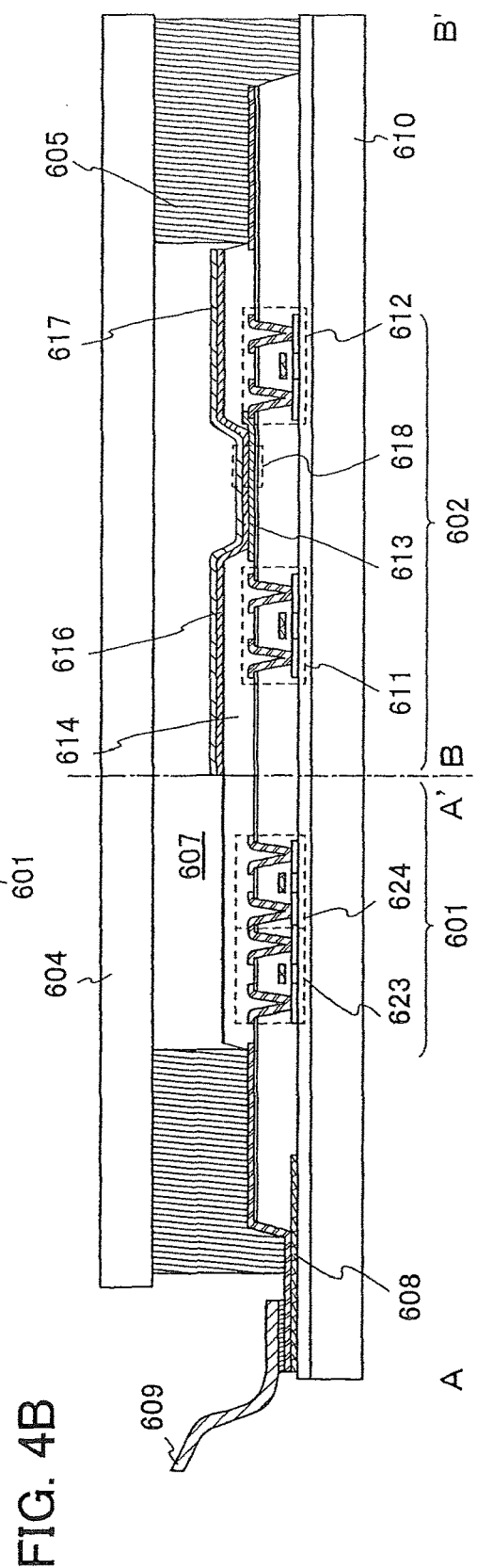

In this embodiment mode, a light emitting device including the light emitting element of the present invention in the pixel portion is described with reference to FIGS. 4A and 4B. Note that FIG. 4A is a top view of a light emitting device, and FIG. 4B is a cross-sectional view taken along lines A-A' and B-B' in FIG. 4A. This light emitting device includes a driver circuit portion (a source side driver circuit) 601, a pixel portion 602, and a driver circuit portion (a gate side driver circuit) 603, which are indicated by dotted lines, to control light emission from light emitting elements. Reference numeral 604 denotes a sealing substrate, reference numeral 605 denotes a sealant, and a portion surrounded by the sealant 605 is a space 607.

Note that a lead wiring 608 is a wiring for transmitting signals which are input to the source side driver circuit 601 and the gate side driver circuit 603. The lead wiring 608 receives video signals, clock signals, start signals, reset signals, and the like from a flexible printed circuit (FPC) 609, which is an external input terminal. Although only the FPC is shown in FIGS. 4A and 4B, the FPC may be provided with a printed wiring board (PWB). The category of the light emitting device in this specification includes not only a light emitting device itself but also a light emitting device attached with a FPC or a PWB.

Next, a cross-sectional structure is described with reference to FIG. 4B. Although the driver circuit portion and the pixel portion are formed over an element substrate 610, FIG. 4B shows the source side driver circuit 601, which is one of the driver circuit portions and one pixel in the pixel portion 602.

A CMOS circuit, which is a combination of an n-channel TFT 623 and a p-channel TFT 624, is formed as the source side driver circuit 601. Each driver circuit portion may be any of a variety of circuits such as a CMOS circuit, a PMOS circuit, or an NMOS circuit. While a driver integration type in which a driver circuit is formed over a substrate provided with a pixel portion is described in this embodiment mode, a driver circuit is not necessarily formed over a substrate provided with a pixel portion, a driver circuit can be formed outside the substrate.

The pixel portion 602 has a plurality of pixels each including a switching TFT 611, a current control TFT 612, and a first electrode 613 which is electrically connected to a drain of the current control TFT 612. An insulator 614 is formed so as to cover an end portion of the first electrode 613. In this case, the insulator 614 is formed using a positive photosensitive acrylic resin film.

The insulator 614 is formed to have a curved surface having a curvature at an upper end portion or a lower end portion in order to make the coverage favorable. For example, in the case of using positive photosensitive acrylic as a material for the insulator 614, it is preferable that the insulator 614 be formed so as to have a curved surface with a curvature radius (0.2 μm to 3 μm) only at the upper end portion. The insulator 614 can be formed using either a negative type which becomes insoluble in an etchant by light irradiation or a positive type which becomes soluble in an etchant by light irradiation.

An EL layer 616 and a second electrode 617 are formed over the first electrode 613. The first electrode 613 can be formed using any of a variety of metals, alloys, and conductive compounds, a mixture thereof, or the like. When the first electrode serves as an anode, it is preferable that the first electrode be formed using a metal, an alloy, or a conductive compound with a high work function (a work function of equal to or higher than 4.0 eV), or a mixture thereof. For example, the first electrode 613 can be formed using a single-layer film like an indium tin oxide film containing silicon, an indium zinc oxide film, a titanium nitride film, a chromium film, a tungsten film, a Zn film, or a Pt film; or a stacked film, such as a stack of a titanium nitride film and a film containing aluminum as its main component, or a three-layer structure of a titanium nitride film, a film containing aluminum as its main component, and a titanium nitride film. Note that when the first electrode 613 has a stacked structure, it can have low resistance as a wiring, form a favorable ohmic contact, and serve as an anode.

The EL layer 616 includes the organometallic complex described in Embodiment mode 1. The EL layer 616 is formed by any of a variety of methods such as an evaporation method using an evaporation mask using an evaporation mask, a droplet discharge method, or a spin coating method. Either low molecular compounds or high molecular compounds (e.g., an oligomer or a dendrimer) may be used as a material for forming the EL layer 616. Note that, not only an organic compound but also an inorganic compound may be used as the material used for the EL layer.

The second electrode 617 can be formed using any of a variety of metals, alloys, and conductive compounds, a mixture thereof, and the like. When the second electrode serves as a cathode, it is preferable that the second electrode be formed using any of a metal, an alloy, and a conductive compound with a low work function (a work function of equal to or less than 3.8 eV or lower), or a mixture thereof. Examples thereof are elements belonging to Group 1 or Group 2 of the periodic table, that is, alkali metals such as lithium (Li) and cesium (Cs) and alkaline-earth metals such as magnesium (Mg), calcium (Ca), and strontium (Sr), alloys thereof (MgAg or AlLi), and the like. Note that when light emitted from the EL layer 616 is transmitted through the second electrode 617, the second electrode 617 can be formed using a stack of a metal thin film with a reduced thickness and a transparent conductive film (e.g., a film of indium tin oxide (ITO), indium tin oxide containing silicon or silicon oxide, indium zinc oxide (IZO), or indium oxide containing tungsten oxide and zinc oxide (IWZO)).

The sealing substrate 604 is attached to the element substrate 610 with the sealant 605; thus, a light emitting element 618 is in the space 607 surrounded by the element substrate 610, the sealing substrate 604, and the sealant 605. The space 607 is filled with a filler such as an inert gas (e.g., nitrogen or argon) or the sealant 605.

It is preferable that the sealant 605 be an epoxy-based resin and a material of the sealant 605 permeate little moisture and oxygen as much as possible. As the sealing substrate 604, a plastic substrate made of fiberglass-reinforced plastics (FRP), polyvinyl fluoride (PVF), polyester, acrylic, or the like can be used as an alternative to a glass substrate or a quartz substrate.

Accordingly, the light emitting device having the light emitting element of the present invention can be obtained.

Since a light emitting device of the present invention has a light emitting element with high light emission efficiency, power consumption is reduced.

Since a light emitting device of the present invention can be formed using the composition described in Embodiment Mode 1, the light emitting device is excellent in mass productivity. Also, the manufacturing cost is reduced because of high use efficiency of the material, whereby a low cost light emitting device can be obtained.

Figure 5A:
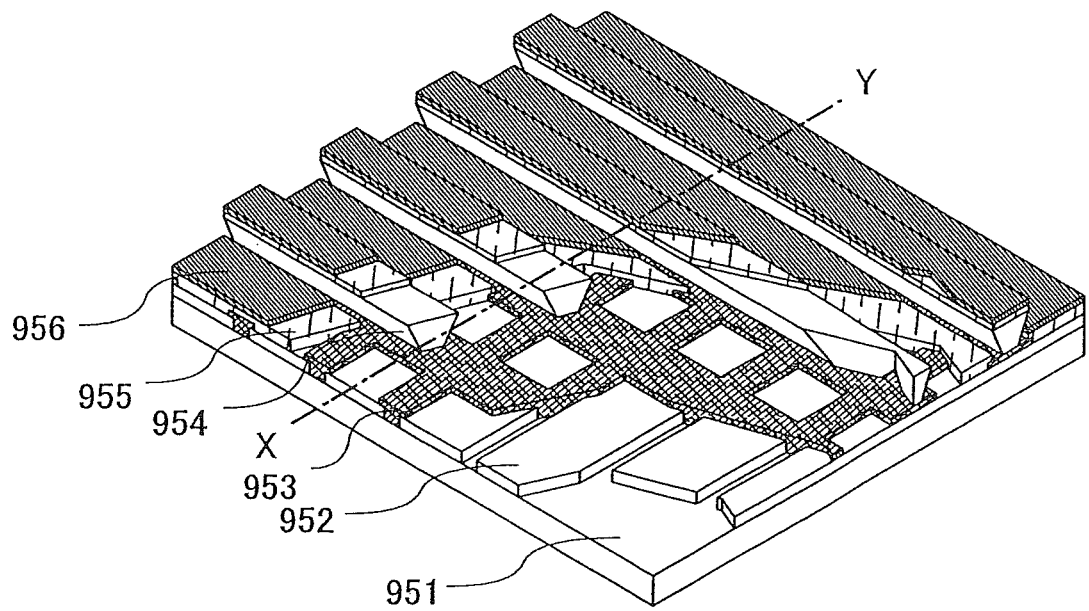
FIGS. 5A and 5B illustrate a light emitting element of the present invention.
Figure 5B:
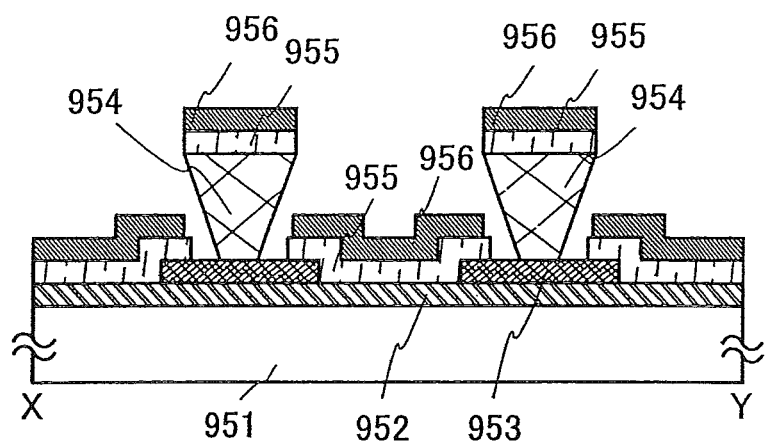

Although an active matrix light emitting device in which driving of a light emitting element is controlled by a transistor is described in this embodiment mode, the light emitting device may be a passive matrix light emitting device. Note that FIGS. 5A and 5B show a passive matrix light emitting device to which the present invention is applied. FIG. 5A is a perspective view of the light emitting device, and FIG. 5B is a cross-sectional view taken along line X-Y in FIG. 5A. In FIGS. 5A and 5B, an EL layer 955 is provided between an electrode 952 and an electrode 956 over a substrate 951. End portions of the electrode 952 are covered with an insulating layer 953. Then, a partition layer 954 is provided over the insulating layer 953. A side wall of the partition layer 954 slopes so that the distance between one side wall and the other side wall becomes narrow toward the substrate surface. In other words, a cross section taken in the direction of the short side of the partition layer 954 is trapezoidal, and the base of the cross-section (a side facing in the same direction as a plane direction of the insulating layer 953 and in contact with the insulating layer 953) is shorter than the upper side of the cross-section (a side facing in the same direction as the plane direction of the insulating layer 953 and not in contact with the insulating layer 953). A cathode can be patterned by providing the partition layer 954 in this manner. The passive matrix light emitting device can also be driven with low power consumption when it includes a light emitting element having high emission efficiency.

Embodiment Mode 5

In this embodiment mode, one mode is described in which a layer 716 including an organometallic complex of the present invention is formed by a droplet discharge method, which is a wet process, with reference to FIGS. 10A to 10D and 11. FIGS. 10A to 10D show a manufacturing steps of a light-emitting element portion of the light emitting device which is shown in FIGS. 4A and 4B.

Figure 10A:
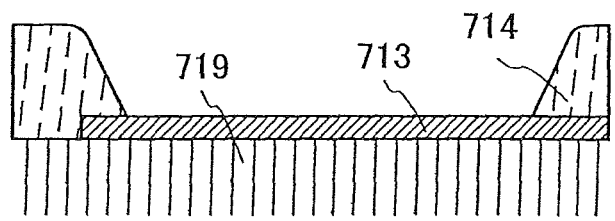
FIGS. 10A to 10D illustrate a method for manufacturing a light emitting element of the present invention.
Figure 10B:
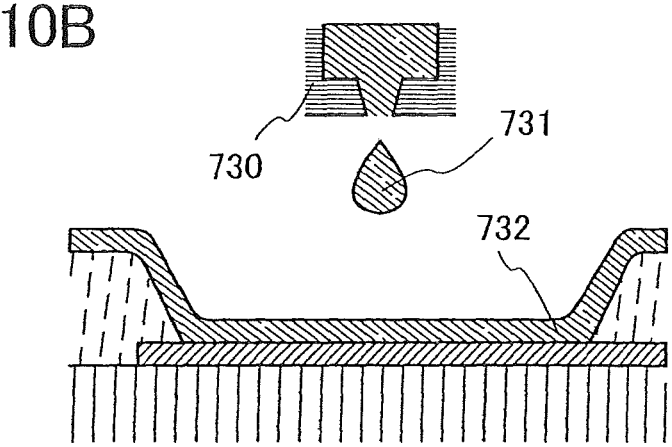
Figure 10C:
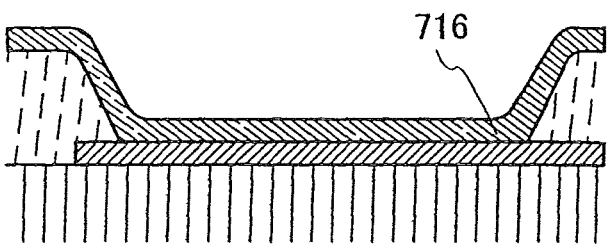

In FIG. 10A, a first electrode 713 is formed over an insulating layer 719, and an insulating layer 714 is formed so as to cover a part of the first electrode 713. Into an exposed portion of the first electrode 713, which is an opening of the insulating layer 714, a droplet 731 is discharged from a droplet discharge device 730 to form a layer 732 containing a composition. The droplet 731 is a composition including an organometallic complex of the present invention and a solvent and is deposited onto the first electrode 713 (see FIG. 10B). The solvent is removed from the layer 732 containing a composition and the layer 732 containing a composition is solidified, whereby the layer 716 including an organometallic complex is formed (see FIG. 10C). The solvent may be removed by drying or a heating step. In addition, the step of discharging the composition may be performed under reduced pressure.

Figure 10D:
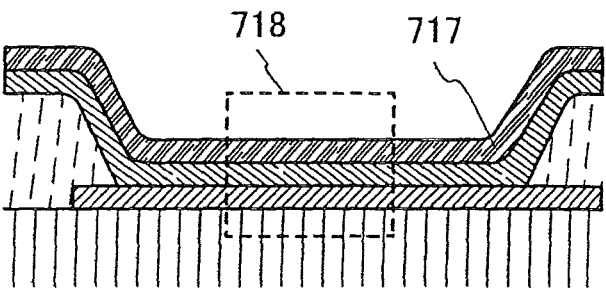

A second electrode 717 is formed over the layer 716 including an organometallic complex, whereby a light emitting element 718 is manufactured (see FIG. 10D). While FIGS. 10A to 10D show a structure in which only the layer 716 including an organometallic complex is provided between the first electrode 713 and the second electrode 717, a layer including another material may be provided between the first electrode 713 and the layer 716 including an organometallic complex. As is described in Embodiment Mode 1, an organometallic complex of the present invention is soluble in alcohol; therefore, when a composition including alcohol as a solvent is used, EL layers of a light emitting element can be stacked. Further, a layer including another material may be provided between the layer 716 including an organometallic complex and the second electrode 717.

When the layer 716 including an organometallic complex is formed by a droplet discharge method as described in this embodiment mode, the composition can be selectively discharged in a region in which the layer is to be formed, and accordingly, less material is wasted. In addition, a photolithography process or the like for processing a shape is not needed, and thus, the process is simplified and the cost can be reduced.

A droplet discharging means which is used in this embodiment mode is a general unit to discharge liquid droplets, such as a nozzle equipped with a composition discharge outlet, a head having one or a plurality of nozzles.

Figure 11:
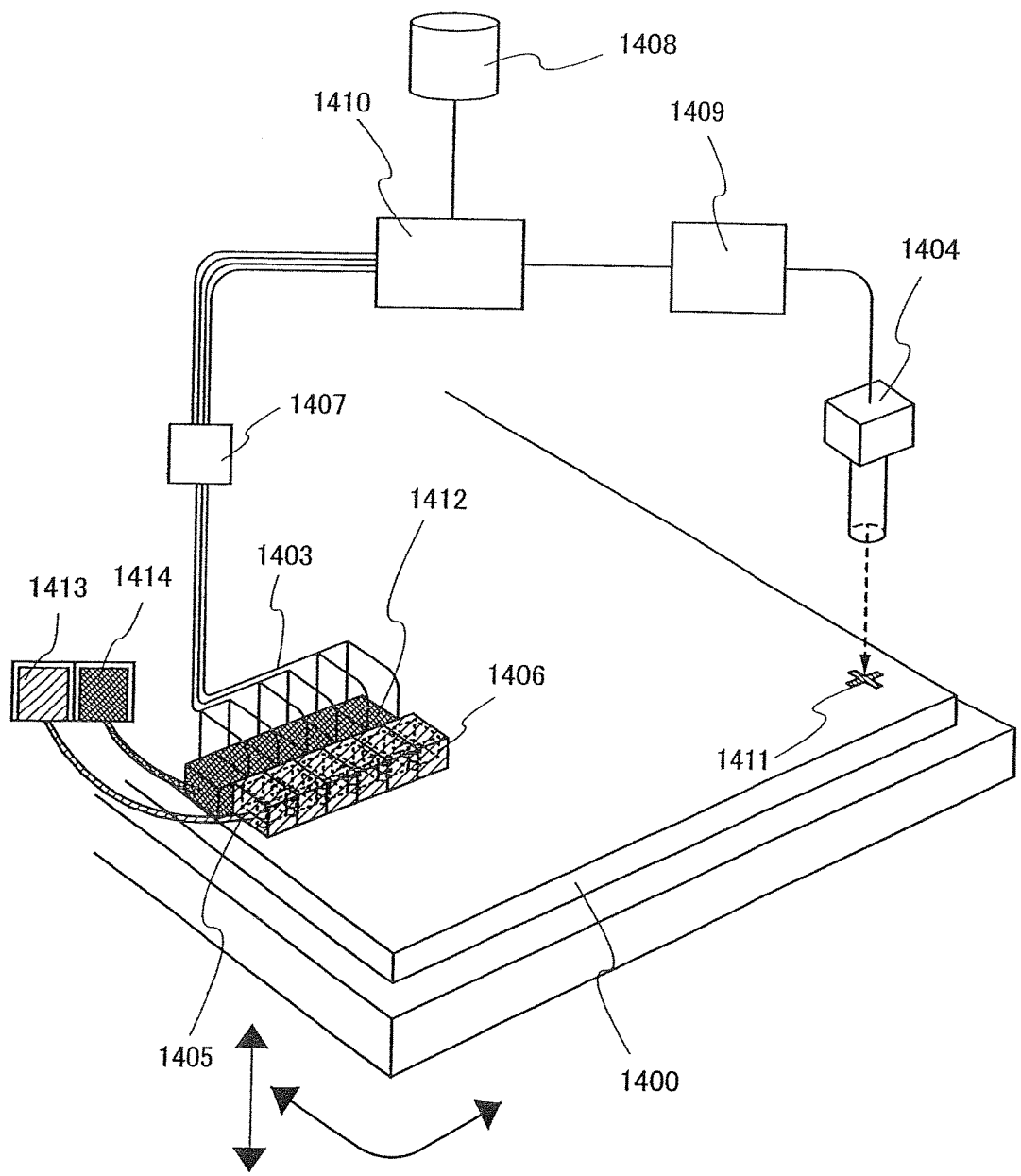
FIG. 11 illustrates a method for manufacturing a light emitting element of the present invention.

One mode of a droplet discharging apparatus used for a droplet discharge method is shown in FIG. 11. Each of heads 1405 and 1412 of a droplet discharging means 1403 is connected to a control means 1407, and this control means 1407 is controlled by a computer 1410; thus, a preprogrammed pattern can be drawn. The timing for dawning may be determined, for example, based on a marker 1411 formed over a substrate 1400. Alternatively, a reference point may be fixed based on an edge of the substrate 1400. The reference point is detected by an imaging means 1404 and converted into a digital signal by an image processing means 1409. Then, the digital signal is recognized by the computer 1410, and then, a control signal is generated and transmitted to the control means 1407. An image sensor or the like using a charge coupled device (CCD) or a complementary metal oxide semiconductor (CMOS) can be used as the imaging means 1404. Needless to say, information about a pattern to be formed over the substrate 1400 is stored in a storage medium 1408, and the control signal is transmitted to the control means 1407 based on the information, and the head 1405 and the head 1412 of the droplet discharging means 1403 can be individually controlled based on the information. A material to be discharged is supplied to the heads 1405 and 1412 from a material supply sources 1413 and 1414 through pipes, respectively.

Inside the head 1405, there are a space filled with a liquid material as indicated by a dotted line 1406 and a nozzle which is a discharge outlet. Although not shown, the internal structure of the head 1412 is similar to that of the head 1405. When the nozzle sizes of the head 1405 and the head 1412 are different from each other, different materials can be discharged with different widths simultaneously. Each head can discharge and draw a plurality of light emitting materials. In the case of drawing over a large area, the same material can be simultaneously discharged to be drawn from a plurality of nozzles in order to improve throughput. When a large substrate is used, the heads 1405 and 1412 can freely move over the substrate in directions indicated by the solid arrows in FIG. 11, and a drawing region can be freely set. Thus, a plurality of the same patterns can be drawn over one substrate.

The step of discharging the composition may be performed under reduced pressure. Further, the substrate may be heated when the composition is discharged. After the composition is discharged, either or both steps of drying and baking are performed. Both the drying and baking steps are heat treatments, but they have different purposes, temperatures, and time periods. For example, drying is performed at 80 to 100° C. for three minutes and a baking is performed at 200 to 550° C. for 15 to 60 minutes. The steps of drying and baking are performed under normal atmospheric pressure or under reduced pressure by laser light irradiation, rapid thermal annealing, heating using a heating furnace, or the like. Note that there is no particular limitation on when and how many times the heat treatment is performed. The temperature for performing the steps of drying and baking in a favorable manner depends on the material of the substrate and properties of the composition.

This embodiment mode can be combined with any other embodiment mode as appropriate.

Embodiment Mode 6

In this embodiment mode, electronic devices of the present invention, which includes the light emitting device described in Embodiment Mode 4, are described. The electronic devices of the present invention have a display portion manufactured using the organometallic complex described in Embodiment Mode 1. In addition, the electronic devices of the present invention have the display portion which consumes lower power.

Examples of the electronic device having the light emitting element manufactured using an organometallic complex of the present invention are cameras such as video cameras or digital cameras, goggle type displays, navigation systems, audio reproducing devices (e.g., car audio components and audio components), computers, game machines, portable information terminals (e.g., mobile computers, cellular phones, portable game machines, and e-book readers), and image reproducing devices provided with recording media (specifically, devices that are capable of reproducing recording media such as digital versatile discs (DVDs) and provided with a display device that can display the image). Specific examples of these electronic devices are shown in FIGS. 6A to 6D.

Figure 6A:
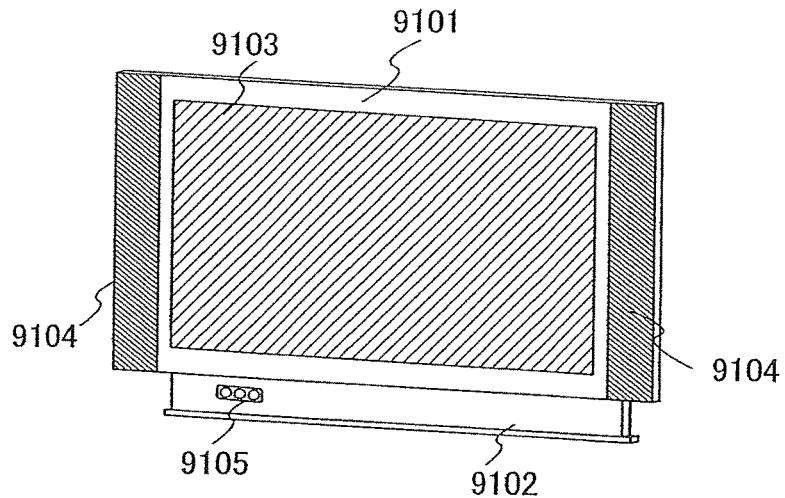
FIGS. 6A to 6D illustrate electronic devices of the present invention.

FIG. 6A shows a television device according to the present invention, which includes a chassis 9101, a supporting base 9102, a display portion 9103, a speaker portion 9104, a video input terminal 9105, and the like. In this television device, the display portion 9103 includes light emitting elements arranged in matrix which are similar to light emitting elements described in Embodiment Modes 2 and 3. The light emitting elements have high emission efficiency. The display portion 9103 which includes the light emitting elements has similar characteristics. Accordingly, the television device consumes low power. Such characteristics can dramatically reduce or downsize power supply circuits in the television device, whereby the chassis 9101 and the supporting base 9102 can be reduced in size and weight. In the television device according to the present invention, low power consumption, high image quality, and reduced size and weight are achieved; therefore, a product suitable for living environment can be provided.

Figure 6B:
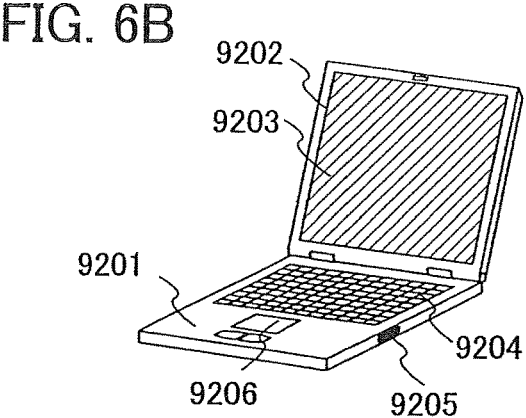

FIG. 6B shows a computer according to the present invention, which includes a main body 9201, a chassis 9202, a display portion 9203, a keyboard 9204, an external connection port 9205, a pointing device 9206, and the like. In this computer, the display portion 9203 includes light emitting elements arranged in matrix which are similar to light emitting elements described in Embodiment Modes 2 and 3. The light emitting elements have high emission efficiency. The display portion 9203 which includes the light emitting elements has similar characteristics. Accordingly, the computer consumes low power. Such characteristics can dramatically reduce or downsize power supply circuits in the computer, whereby the main body 9201 and the chassis 9202 can be reduced in size and weight. In the computer according to the present invention, low power consumption, high image quality, and reduced size and weight are achieved; therefore, a product suitable for the environment can be provided.

Figure 6C:
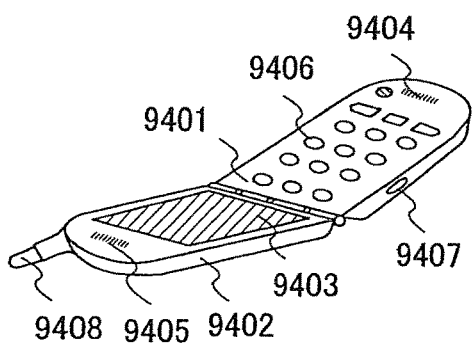

FIG. 6C shows a cellular phone according to the present invention, which includes a main body 9401, a chassis 9402, a display portion 9403, an audio input portion 9404, an audio output portion 9405, an operation key 9406, an external connection port 9407, an antenna 9408, and the like. In this cellular phone, the display portion 9403 includes light emitting elements arranged in matrix which are similar to light emitting elements described in Embodiment Modes 2 and 3. The light emitting elements have high emission efficiency. The display portion 9403 which includes the light emitting elements has similar characteristics. Accordingly, the cellular phone consumes low power. Such characteristics can dramatically reduce or downsize power supply circuits in the cellular phone, whereby the main body 9401 and the chassis 9402 can be reduced in size and weight. In the cellular phone according to the present invention, low power consumption, high image quality, and a small size and light weight are achieved; therefore, a product suitable for carrying can be provided.

Figure 6D:
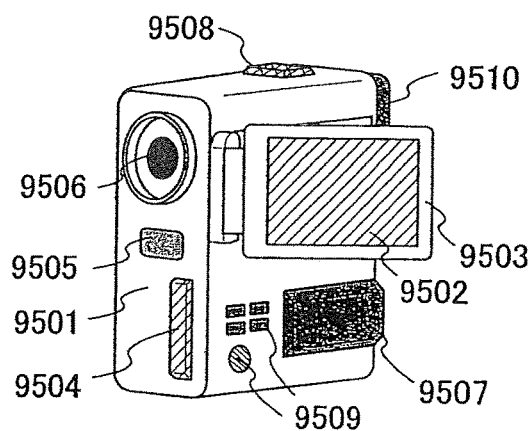

FIG. 6D shows a camera according to the present invention, which includes a main body 9501, a display portion 9502, a chassis 9503, an external connection port 9504, a remote control receiving portion 9505, an image receiving portion 9506, a battery 9507, an audio input portion 9508, an operation key 9509, an eye piece portion 9510, and the like. In this camera, the display portion 9502 includes light emitting elements arranged in matrix which are similar to light emitting elements described in Embodiment Modes 2 and 3. The light emitting elements are characterized by high emission efficiency. The display portion 9502 which includes the light emitting elements has similar characteristics. Accordingly, the camera consumes low power. Such characteristics can dramatically reduce or downsize power supply circuits in the camera, whereby the main body 9501 can be reduced in size and weight. In the camera according to the present invention, low power consumption, high image quality, and reduced size and weight are achieved; therefore, a product suitable for carrying can be provided.

As described above, the applicable range of the light emitting device of the present invention is so wide that the light emitting device can be applied to electronic devices in various fields. By using the light emitting element of the present invention, an electronic device including a display portion with low power consumption can be provided. Furthermore, the electronic device of the present invention including the light emitting element is manufactured using the composition described in Embodiment Mode 1, and therefore, is excellent in mass productivity. Also, the manufacturing cost is reduced because of high use efficiency of the material, whereby a low cost electronic device can be obtained.

The light emitting device of the present invention can also be used as a lighting device. One mode in which the light emitting device of the present invention is used as a lighting device is described with reference to FIG. 7.

Figure 7:
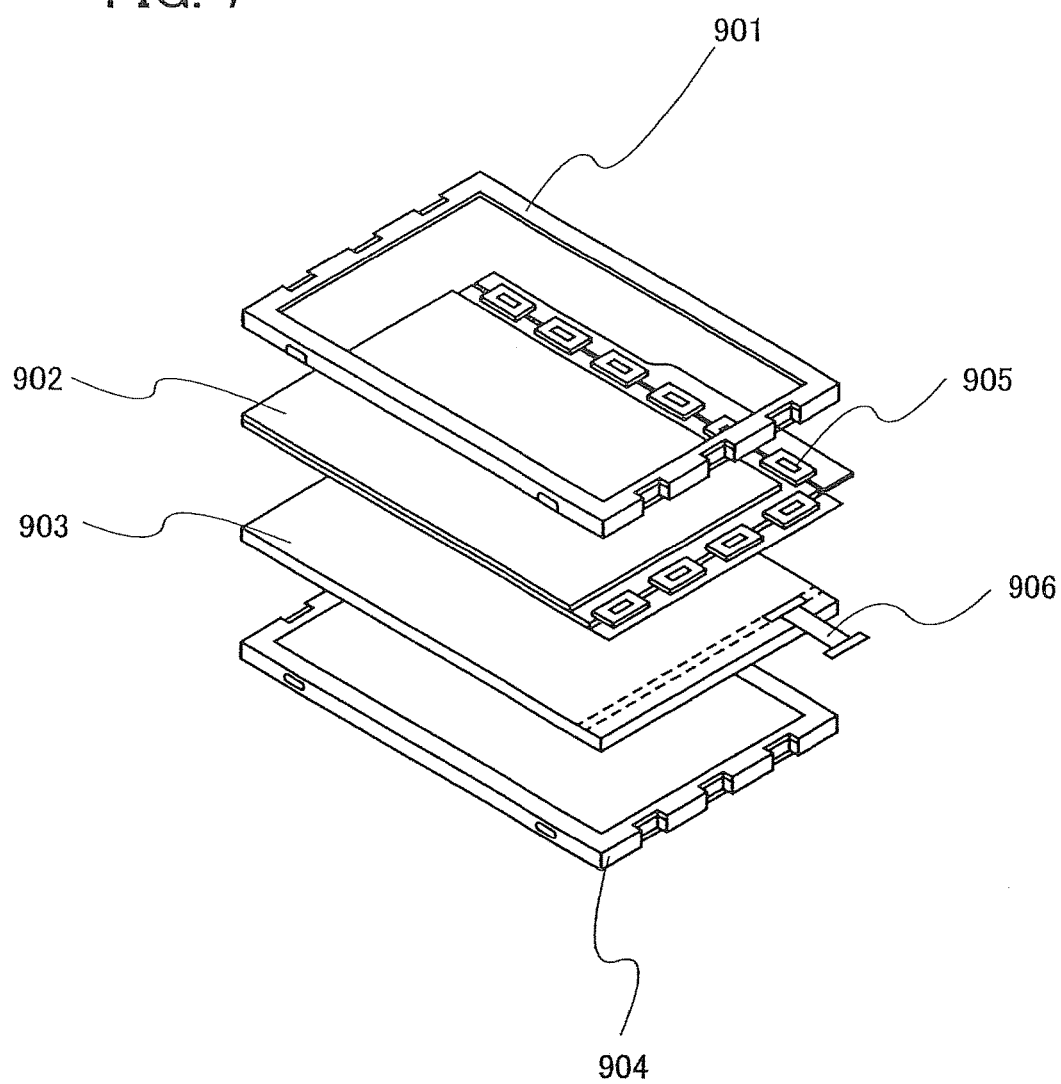
FIG. 7 illustrates an electronic device of the present invention.

FIG. 7 shows an example of a liquid crystal display device in which the light emitting device of the present invention is used as a backlight. The liquid crystal display device shown in FIG. 7 includes a chassis 901, a liquid crystal layer 902, a backlight 903, and a chassis 904. The liquid crystal layer 902 is connected to a driver IC 905. The light emitting device of the present invention is used as the backlight 903, and current is supplied through a terminal 906.

When the light emitting device of the present invention is used as the backlight of the liquid crystal display device, the backlight with reduced power consumption can be obtained. The light emitting device of the present invention is a lighting device with a plane emission area, and this emission area can be readily increased; accordingly, it is possible that the backlight have a larger emission area and the liquid crystal display device have a larger display area. Further, the light emitting device of the present invention has a thin shape and consumes low power; thus, the display device can also be reduced in thickness and power consumption. In addition, the light emitting device of the present invention is formed using the composition described in Embodiment Mode 1, and therefore, is excellent in mass productivity. Also, the manufacturing cost is reduced because of high use efficiency of the material, whereby a low cost light emitting device can be obtained. Accordingly, the liquid crystal display device to which the light emitting device of the present invention is applied has similar characteristics.

Figure 8:
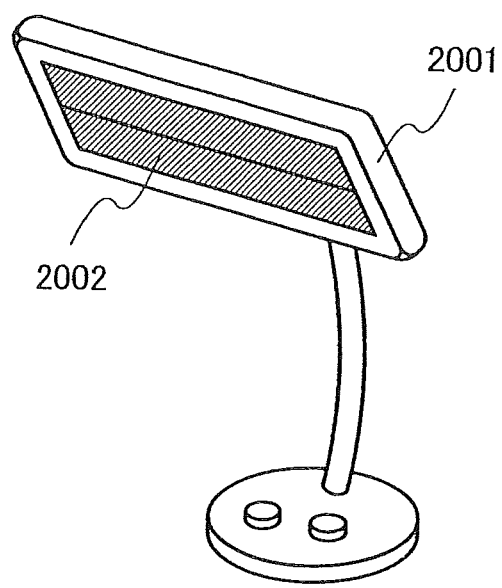
FIG. 8 illustrates a lighting device of the present invention.

FIG. 8 shows an example in which the light emitting device of the present invention is used as a table lamp which is a lighting device. The table lamp shown in FIG. 8 has a chassis 2001 and a light source 2002, and the light emitting device of the present invention is used as the light source 2002. The light emitting device of the present invention can emit light with high luminance, and thus it can illuminate hands doing delicate handwork or the like. The light emitting device of the present invention is manufactured using the composition described in Embodiment Mode 1, and therefore, is excellent in mass productivity. Also, the manufacturing cost is reduced because of high use efficiency of the material, whereby a low cost light emitting device can be obtained.

Figure 9:
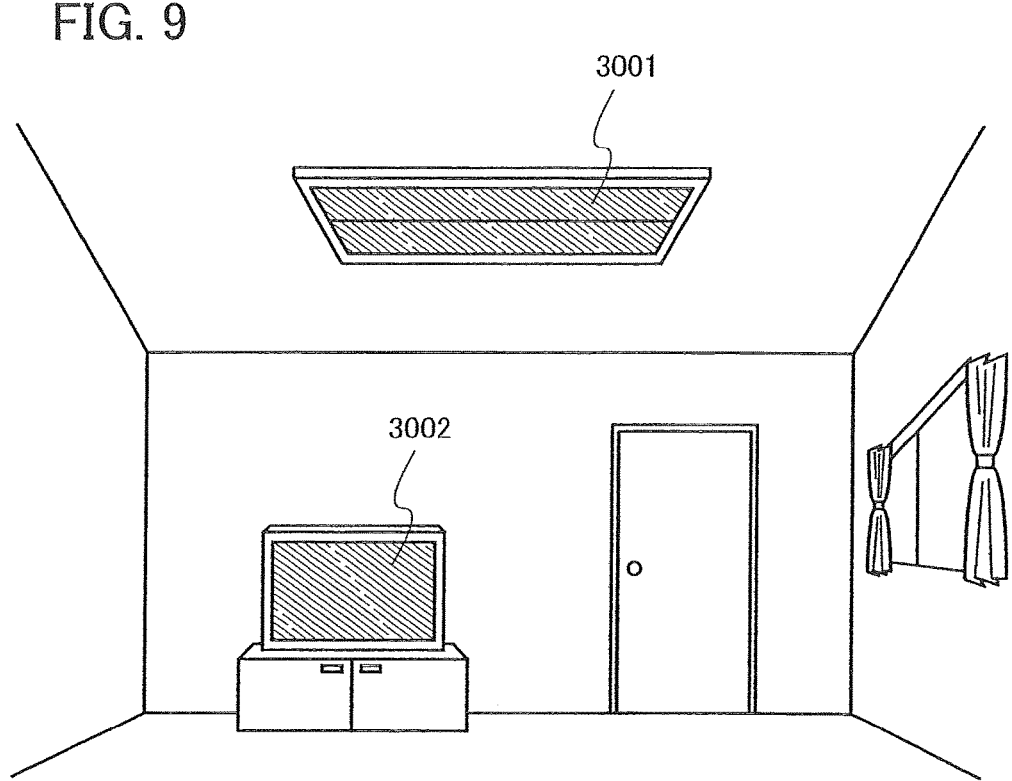
FIG. 9 illustrates a lighting device of the present invention.

FIG. 9 shows an example in which a light emitting device of the present invention is used as an indoor lighting device 3001. Since the light emitting device of the present invention can have a larger emission area, the light emitting device of the present invention can be used as a lighting device having a larger emission area. Further, the light emitting device of the present invention has a thin shape and consumes low power; accordingly, the light emitting device of the present invention can be used as a lighting device having a thin shape and consuming low power. When a television device according to the present invention as described with reference to FIG. 6A is placed in a room in which a light emitting device according to the present invention is used as the indoor lighting device 3001, public broadcasting and movies can be watched. In such a case, since both of the devices consume low power, powerful images can be watched in a bright room without concern about electricity charges.

Example 1

Synthesis Example 1

Synthesis Example 1 describes a specific example of synthesis of bis(2,3,5-triphenylpyrazinato)(dipivaloylmethanato)iridium(III) (abbr.: [Ir(tppr)$_2$(dpm)]), which is an organometallic complex of the present invention and is represented by a structural formula (147) described in Embodiment Mode 1.

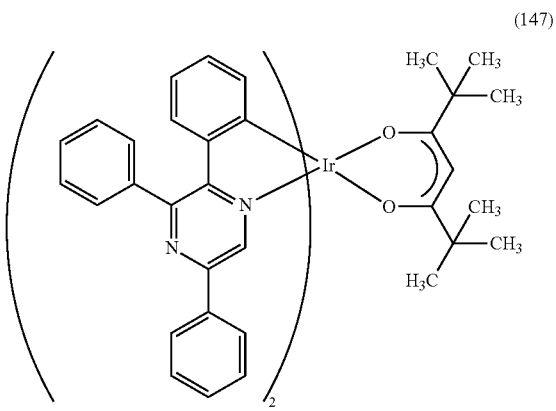

(147)

Step 1: Synthesis of 2,3,5-triphenylpyrazine (abbr.: Htppr)

First, 5.5 mL of a dibutyl ether solution of phenyl lithium (manufactured by Wako Pure Chemical Industries, Ltd., 2.1 mol/L) and 50 mL of diethyl ether were mixed under a nitrogen atmosphere. Then, 2.43 g of 2,3-diphenylpyrazine was dropped into this solution while the solution was being cooled with ice, and the mixture was stirred at room temperature for 24 hours. Water was added to the mixture, and the organic layer was extracted with diethyl ether. The extracted organic layer was washed with water and dried with magnesium sulfate. After the drying, an excess amount of activated manganese dioxide was added to the organic layer, and the mixture was filtered. After the solvent of the solution was distilled off, the obtained residue was recrystallized with ethanol to give a pyrazine derivative, Htppr (a yellow powder, 56% yield). The synthetic scheme of Step 1 is represented by (a-1) below.

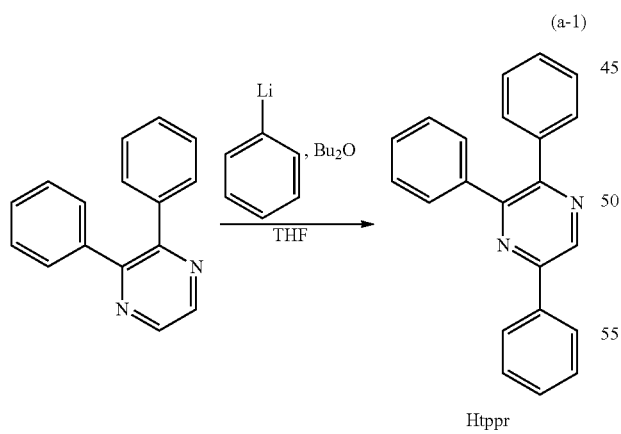

(a-1)

Step 2: Synthesis of di-μ-chloro-bis[bis(2,3,5-triphenylpyrazinato)iridium(III)] (abbr.: [Ir(tppr)$_2$Cl]$_2$)

Next, 1.08 g of Htppr, which is the pyrazine derivative obtained in above-described Step 1, and 0.73 g of iridium chloride hydrate (IrCl$_3$.H$_2$O) (manufactured by Sigma-Aldrich Corp.) were mixed in a mixed solvent of 30 mL of 2-ethoxyethanol and 10 mL of water. The mixture was refluxed for 16 hours under a nitrogen atmosphere. The precipitated powder was filtered and washed with ethanol, diethyl ether, and then, hexane to give a binuclear complex [Ir(tppr)$_2$Cl]$_2$ (an orange powder, 97% yield). The synthetic scheme of Step 2 is represented by (b-1) below.

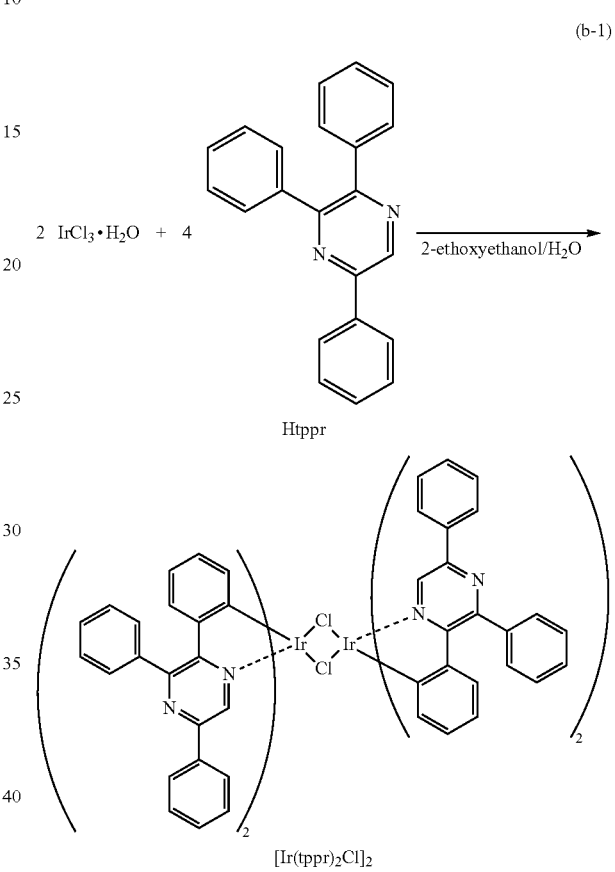

(b-1)

Step 3: Synthesis of bis(2,3,5-triphenylpyrazinato)(dipivaloylmethanato)iridium(III) (abbr.: [Ir(tppr)$_2$(dpm)])

First, 25 mL of 2-ethoxyethanol, 0.40 g of [Ir(tppr)$_2$Cl]$_2$, which is a binuclear complex obtained in above-described Step 2, 0.14 mL of dipivaloylmethane, and 0.25 g of sodium carbonate were put in an eggplant flask with a reflux pipe, and the air in the flack was replaced with argon. Then, irradiation with microwave (2.45 GHz, 150 W) for 15 minutes was performed to cause a reaction. The reacted solution was filtered and the obtained filtrate was recrystallized with ethanol. The obtained red powder was washed with ethanol, and then, diethyl ether to give [Ir(tppr)$_2$(dpm)], which is an organometallic complex of the present invention (75% yield). For the irradiation of microwave, a microwave synthesis system (Discover, manufactured by CEM Corporation) was used. The synthetic scheme of Step 3 is represented by (c-1) below.

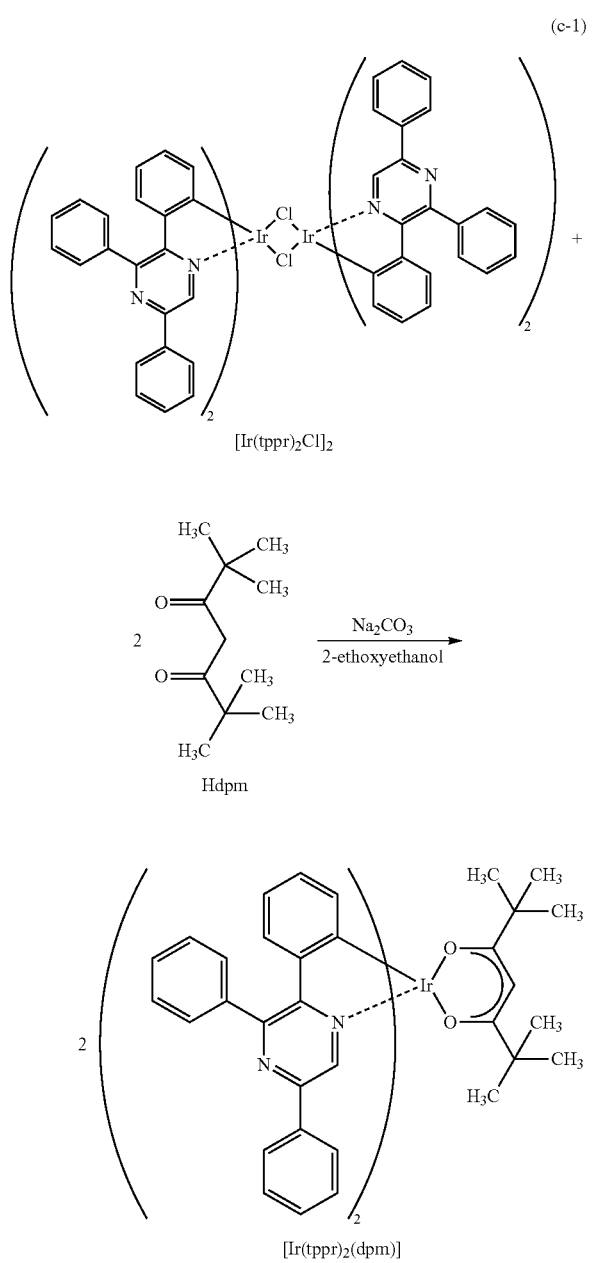

[Ir(tppr)$_2$Cl]$_2$

Hdpm

[Ir(tppr)$_2$(dpm)]

Figure 12:
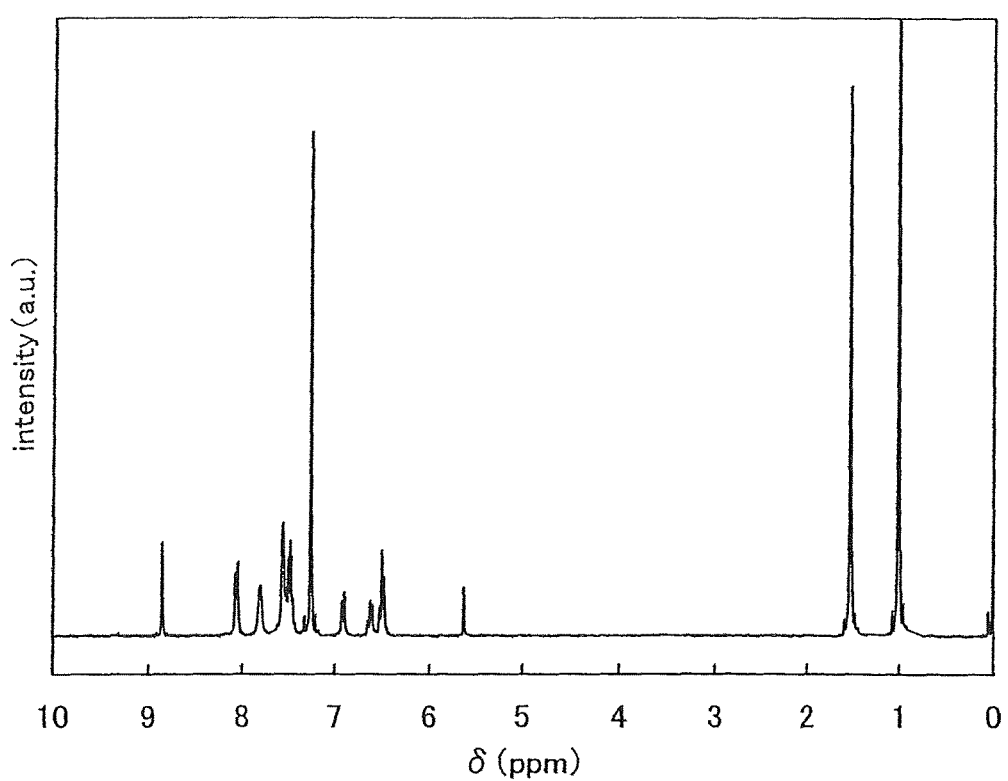
FIG. 12 illustrates the $^1$H NMR spectrum of bis(2,3,5-triphenylpyrazinato)(dipivaloylmethanato)iridium(III) (abbr.: [Ir(tppr)$_2$(dpm)])

An analysis result of the red powder obtained in Step 3 by nuclear magnetic resonance spectrometry ($^1$H-NMR) is shown below and the $^1$H NMR spectrum is shown in FIG. 12. The analysis result reveals that [Ir(tppr)$_2$(dpm)], which is an organometallic complex of the present invention which is represented by the structural formula (147), was obtained in this Synthesis Example 1.

The $^1$H NMR data is shown below. $^1$H NMR.δ (CDCl$_3$): 1.02 (s, 18H), 5.64 (s, 1H), 6.51 (m, 4H), 6.64 (m, 2H), 6.92 (d, 2H), 7.44-7.56 (m, 12H), 7.80 (brs, 4H), 8.06 (d, 4H), 8.86 (s, 2H).

The decomposition temperature of the obtained organometallic complex of the present invention, [Ir(tppr)$_2$(dpm)], was measured with a high vacuum differential type differential thermal balance (TG-DTA2410SA, manufactured by Bruker AXS K.K.). The temperature increase rate was 10° C./min, and the temperature was increased under normal atmospheric pressure. Reduction in weight by 5% was observed at 327° C., which is indicative of favorable heat resistance of [Ir(tppr)$_2$(dpm)].

The absorption spectrum of [Ir(tppr)$_2$(dpm)] was measured with an ultraviolet-visible spectrophotometer (V-550, manufactured by JASCO Corporation), using a dichloromethane solution (0.094 mmol/L) at room temperature. Further, the emission spectrum of [Ir(tppr)$_2$(dpm)] was measured with a fluorescence spectrophotometer (FS920, manufactured by Hamamatsu Photonics K.K.), using a degassed dichloromethane solution (0.33 mmol/L) at room temperature. The excitation wavelength was 465 nm. The measurement result is shown in FIG. 13 in which the horizontal axes indicate a wavelength and the vertical axis indicates a molar absorption coefficient and an emission intensity.

Figure 13:
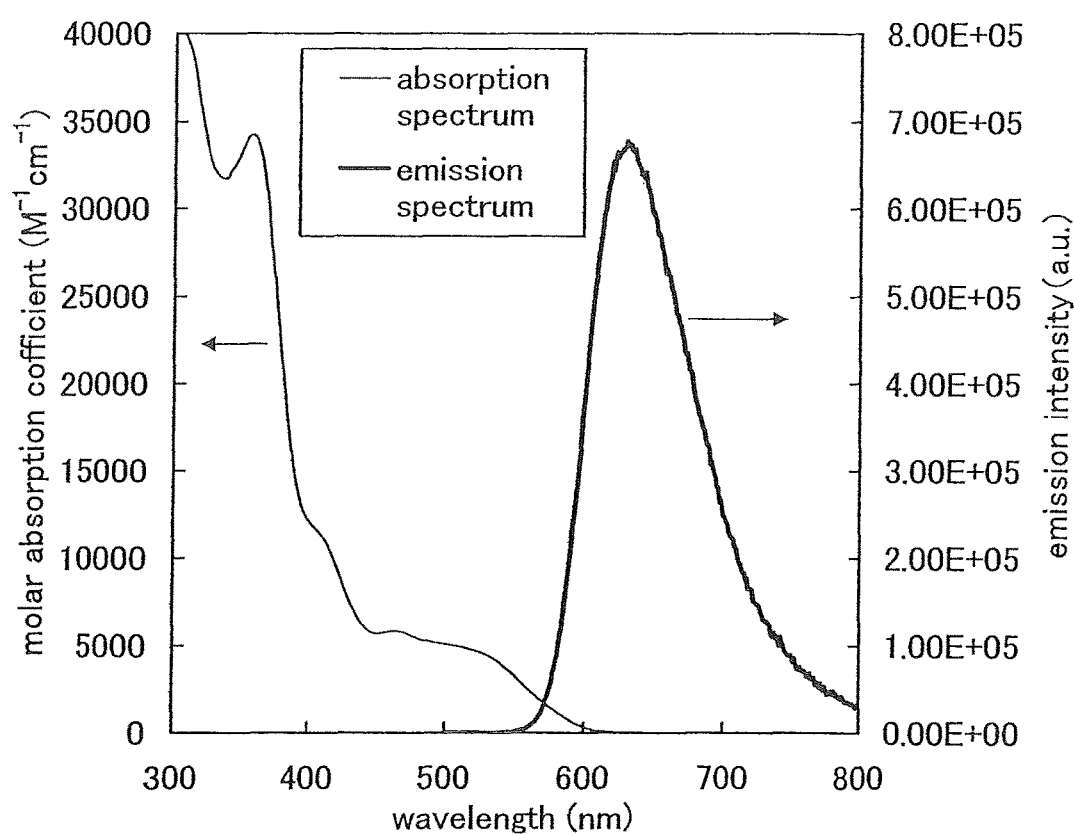
FIG. 13 illustrates the absorption spectrum and the emission spectrum of bis(2,3,5-triphenylpyrazinato)(dipivaloylmethanato)iridium(III) (abbr.: [Ir(tppr)$_2$(dpm)])

As is shown in FIG. 13, an organometallic complex of the present invention [Ir(tppr)$_2$(dpm)] has a light emission peak at 630 nm and red light was observed from the solution.

Example 2

In this Example, the solubility of an organometallic complex including a pyrazine skeleton described in Embodiment Mode 1 was measured. The measurement was performed by examining the solubility in various solvents: 2-ethoxyethanol, isopropanol, and ethanol, which are alcohols; dioxane, which is ether; chloroform and dimethylformamide (DMF), which are an organic solvent not including an aromatic ring; and toluene, which is an aromatic hydrocarbon-based solvent.

Among the complexes disclosed in Embodiment Mode 1, [Ir(tppr)$_2$(dpm)] represented by the structural formula (147), which was synthesized in Example 1, is selected as a measurement object. The solubility was investigated.

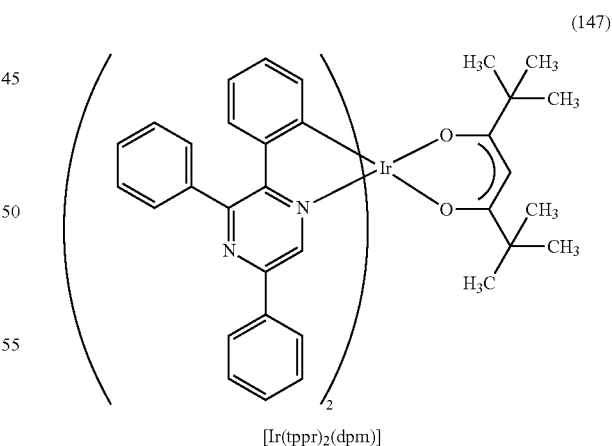

[Ir(tppr)$_2$(dpm)]

The solubility test results of the sample are shown in Table 1 below. In Table 1, a cross indicates that the solubility x (g/L) is x<0.6, a triangle indicates that 0.9>x≥0.6, a circle indicates that 1.2>x≥0.9, and a double circle indicates that x≥1.2.

TABLE 1

| Structural formula No. | Compound abbreviation | Alcohols | | | Ethers | Solvents not having aromatic ring | | sovents having aromatic ring |
|---|---|---|---|---|---|---|---|---|
| | | 2-ethoxyethanol | isopropanol | ethanol | dioxane | chloroform | DMF | toluene |
| (147) | Ir(tppr)$_2$(dpm) | ◎ | Δ | Δ | ◎ | ◎ | ◎ | Δ | solubility x
(g/L)
x ≥ 1.2 ... ◎
1.2 > x ≥ 0.9 ... ○
0.9 > x ≥ 0.6 ... Δ
x < 0.6 ... x

[Ir(tppr)$_2$(dpm)] represented by the structural formula (147), which is synthesized in Example 1 has high solubility. [Ir(tppr)$_2$(dpm)] shows sufficiently high solubility (equal to or greater than 0.6 g/L) in 2-ethoxyethanol, isopropanol, and ethanol, which are alcohols. It is found that [Ir(tppr)$_2$(dpm)] has extremely high solubility (equal to or greater than 1.2 g/L) in 2-ethoxyethanol in particular. Accordingly, [Ir(tppr)$_2$(dpm)] is preferably used for a composition for coating which is used for a light emitting element manufactured by a wet process.

In addition, it is found that [Ir(tppr)$_2$(dpm)] represented by the structural formula (147) also has extremely high solubility (equal to or greater than 1.2 g/L) in dioxane, which is ether. In addition, it is found that [Ir(tppr)$_2$(dpm)] also has extremely high solubility (equal to or greater than 1.2 g/L) in chloroform and dimethylformamide (DMF), which are an organic solvent not including an aromatic ring. In addition, [Ir(tppr)$_2$(dpm)] also has sufficiently high solubility (equal to or greater than 0.6 g/L) in toluene, which is an aromatic hydrocarbon-based solvent. Accordingly, since [Ir(tppr)$_2$(dpm)] represented by the structural formula (147) has solubility in many kinds of solvents, [Ir(tppr)$_2$(dpm)] is preferably used for a composition for coating.

As described above, the inventors of the present invention have found that solubility becomes higher when a ligand represented by the general formula (L1) is introduced. In particular, improvement in solubility in a solvent not including an aromatic ring (e.g., alcohols) is very distinctive.

Example 3

In this Example, a light emitting element using an organometallic complex of the present invention is described.

<<Preparation of Solution A>>

First, solution A including an organometallic complex of the present invention was prepared by dissolving 0.305 g of bis(2-methyl-8-quinolinolato)(4-phenylphenolato)aluminum(III) (manufactured by Chemipro Kasei Kaisha, Ltd., a product purified by sublimation) (abbr.: BAlq), 0.0151 g of N,N'-bis(3-methylphenyl)-N,N'-diphenyl-[1,1'-biphenyl]-4,4'-diamine (manufactured by Tokyo Chemical Industry Co., Ltd.) (abbr.: TPD), and 0.029 g of Ir(tppr)$_2$(dpm), which was synthesized in Example 1, in 20 mL of 2-methoxyethanol (manufactured by Kanto Chemical Co., Inc.). Note that the solution A was bubbled with argon for one hour in order to remove oxygen, immediately before spin coating. In addition, the solution A in a sample bottle was kept warm in an oven set at a temperature of 75° C. (atmospheric pressure) until it was used for film formation. Structural formulae of BAlq, TPD, and Ir(tppr)$_2$(dpm) are shown below.

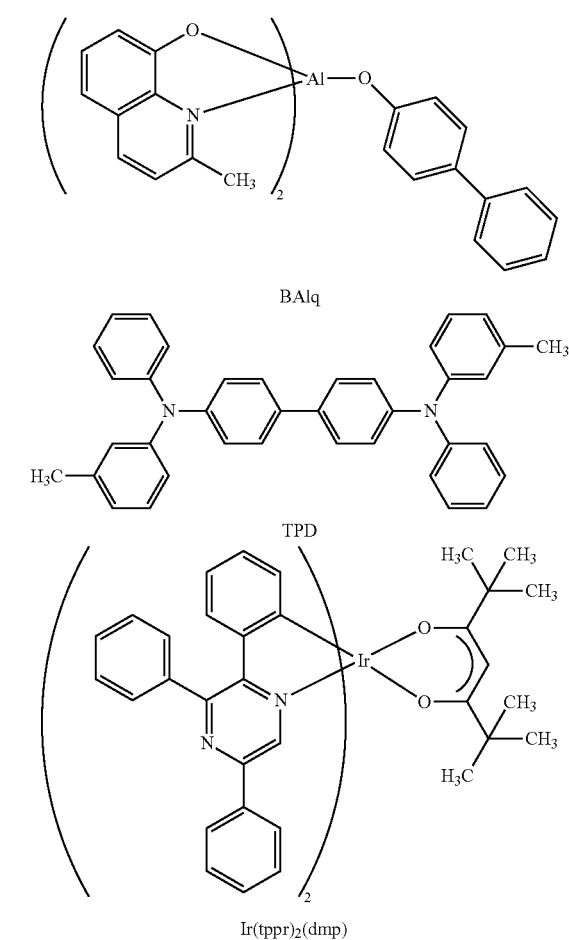

<<Preparation of Solution B>>

Solution B was prepared by dissolving 0.10 g of polyvinylcarbazole (Mw=1100000, manufactured by Sigma-Aldrich Corp.) (abbr.: PVK) and 0.0255 g of 4,4'-bis[N-(1-naphthyl)-N-phenylamino]biphenyl (manufactured by Chemipro Kasei Kaisha, Ltd., a product purified by sublimation) (abbr.: NPB) in 40 mL of 1,4-dioxane (dehydration) (manufactured by Kanto Chemical Co. Inc.). Structural formulae of PVK and NPB are shown below.

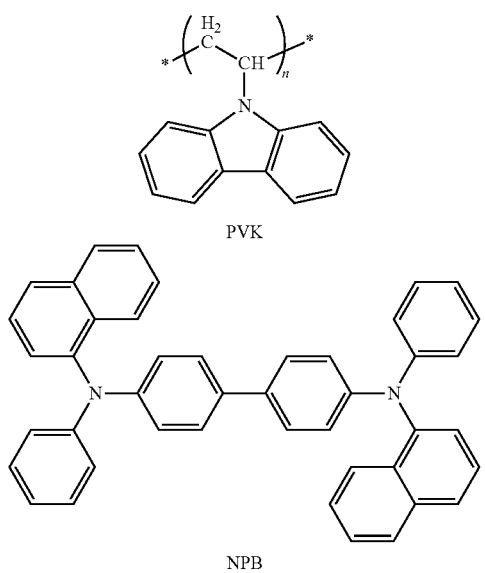

PVK

NPB

<Fabrication of Light Emitting Element 1>

First, a glass substrate over which a film of indium tin silicon oxide (ITSO) was formed with a thickness of 110 nm was prepared. The surface of the ITSO was covered with a polyimide film in a manner such that an area of 2 mm×2 mm of the surface was exposed. Note that the ITSO serves as an anode of the light emitting element. As a pretreatment for forming the light emitting element over this substrate, a mixed solution of water and 2-ethoxyethanol that were mixed in a volume ratio of 3:2 was dropped onto the ITSO, and the ITSO was spin-coated with the mixed solution.

Next, 15 mL of PEDOT/PSS (AI4083sp.gr, manufactured by H.C. Starck GmbH) and 10 mL of 2-ethoxyethanol were mixed to obtain a mixed solution, and this mixed solution was dropped onto the ITSO. Immediately thereafter, the ITSO was spin-coated with the mixed solution at a spinning rate of 2000 rpm for 60 seconds, and then, at a spinning rate of 3000 rpm for 10 seconds. Then, after an end portion of the substrate was wiped so as to expose a terminal connected to the ITSO, baking was performed at 110° C. for two hours in a vacuum dryer in which the pressure was reduced with a rotary pump, whereby a film of PEDOT/PSS was formed with a thickness of 50 nm as a hole-injecting layer over the ITSO.

Next, in a glove box (at an oxygen concentration of equal to or lower than 20 ppm and a moisture concentration of equal to or lower than 5 ppm), the PEDOT/PSS was spin-coated with the solution B which had already been prepared. The spin coating was carried out at a spinning rate of 300 rpm for 2 seconds, and then, at a spinning rate of 2000 rpm for 60 seconds, and further, at a spinning rate of 2500 rpm for 10 seconds. Then, after an end portion of the substrate was wiped so as to expose the terminal connected to the ITSO, vacuum heat drying was performed at 120° C. for one hour in a vacuum dryer in which the pressure is reduced with a rotary pump; thus, a hole-transporting layer was formed. Note that when a film of the solution B was formed over a glass substrate under the above-described film formation conditions, the film thickness was found to be 15 nm by a measurement using a surface profiler (Dektak V200Si, manufactured by Ulvac, Inc.).

Next, the substrate over which films of PEDOT/PSS and PVK/NPB were formed was positioned in a glove box (at an oxygen concentration of equal to or lower than 10 ppm and a moisture concentration of equal to or lower than 2 ppm) without the substrate being exposed to atmosphere; and then, the hole-transporting layer was spin-coated with solution A. The spin coating was carried out at a spinning rate of 300 rpm for 2 seconds, and then, at a spinning rate of 500 rpm for 60 seconds, and further, at a spinning rate of 2500 rpm for 10 seconds. Then, after an end portion of the substrate was wiped so as to expose the terminal connected to the ITSO, vacuum heat drying was performed at 100° C. for one hour in a vacuum dryer in which the pressure is reduced with a rotary pump, whereby a light emitting layer was formed. Note that when a film of solution A was formed over a glass substrate under the above-described film formation conditions, the film thickness was found to be 40 nm by a measurement using a surface profiler (Dektak V200Si, manufactured by Ulvac, Inc.).

Then, the above-described substrate was positioned in a vacuum vapor deposition apparatus without the substrate being exposed to atmosphere, and fixed to a holder in the vacuum vapor deposition apparatus so that a surface over which the light emitting layer was formed faced downward.

After the pressure in the vacuum vapor deposition apparatus was reduced to $10^{-4}$ Pa, bis(2-methyl-8-quinolinolato) (4-phenylphenolato)aluminum(III) (abbr.: BAlq) was vapor-deposited to have a thickness of 10 nm, whereby a first electron-transporting layer was formed. Bathophenanthroline (abbr.: BPhen) was vapor-deposited to have a thickness of 20 nm on the first electron-transporting layer, whereby a second electron-transporting layer was formed. In addition, lithium fluoride (LiF) was vapor-deposited to have a thickness of 1 nm on the second electron-transporting layer, whereby an electron-injecting layer was formed. Lastly, a film of aluminum was formed to have a thickness of 200 nm as a cathode. Thus, the light emitting element 1 of the present invention was obtained. Note that in the above-described vapor deposition process, vapor deposition was all performed by a resistance heating method. A structural formula of BPhen is shown below.

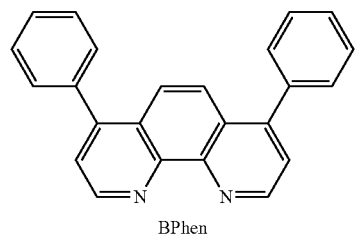 [SMILES: c1ccc(-c2ccnc3c2ccc2c(-c4ccccc4)ccnc23)cc1]

BPhen

<Operating Characteristics of Light Emitting Element 1>

Thus obtained light emitting element 1 was sealed in a glove box with a nitrogen atmosphere so that the light emitting element 1 was not exposed to atmosphere. Then, the operating characteristics of the light emitting element 1 were measured. Note that the measurements were carried out at room temperature (an atmosphere kept at 25° C.).

Figure 14:
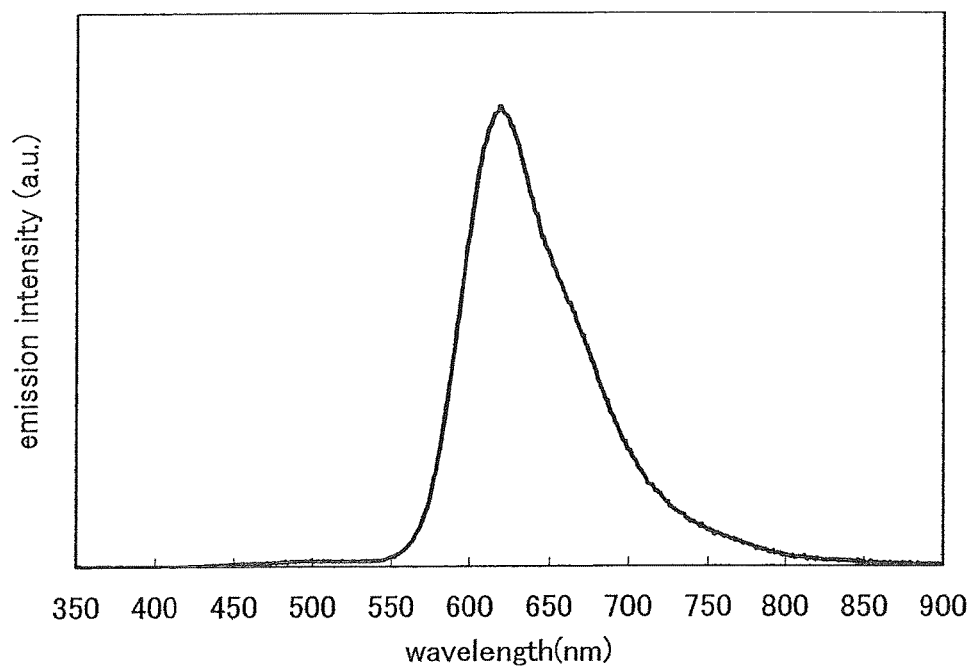
FIG. 14 illustrates the emission spectrum of a light emitting element fabricated in Example 3.

FIG. 14 shows the emission spectrum of the light emitting element 1 when a current of 1 mA flows through the light emitting element 1.

When the luminance of the light emitting element 1 was 1025 cd/m², the CIE color coordinates were x=0.66 and y=0.34, the emission color was red, and the current efficiency was 3.2 cd/A. In addition, when the luminance of the light emitting element 1 was 1025 cd/m², the voltage was 12.0 V, the current density was 31.9 mA/cm$^2$, and the power efficiency was 0.8 lm/W. The wavelength corresponding to the peak of the light emission was 618 nm as shown in FIG. 14.

Accordingly, a light emitting element with high emission efficiency can be obtained according to the present invention.

In addition, it is found that a layer can be further formed by a wet process over a layer including an organic compound by using a composition of the present invention. In particular, as described in this example, stacking layers by a wet process is possible by forming a layer which is insoluble in alcohol (the hole-transporting layer in this example) by a wet process, and then, applying a composition of the present invention using alcohol over the layer. Therefore, a method for manufacturing a light emitting element including a composition of the present invention is excellent in mass productivity and suitable for industrial application. Furthermore, the material use efficiency is high; therefore, the manufacturing cost can be reduced.

Example 4

Synthesis Example 2

Synthesis Example 2 describes a specific example of synthesis of bis(2,3,5-triphenylpyrazinato)(pivaloyltrifluoroacetonato)iridium(III) (abbr.: [Ir(tppr)$_2$(pFac)]), which is an organometallic complex of the present invention and is represented by a structural formula (148) described in Embodiment Mode 1.

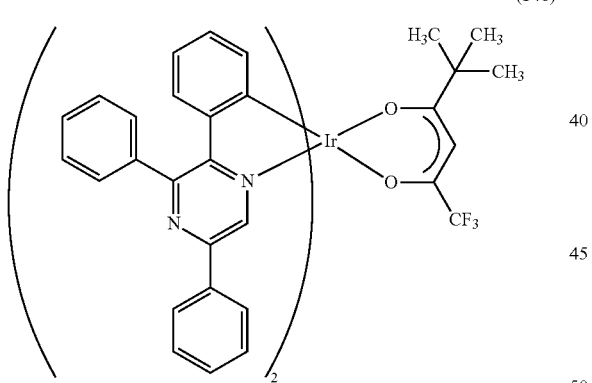

(148)

Synthesis of bis(2,3,5-triphenylpyrazinato)(pivaloyltrifluoroacetonato)iridium(III) (abbr.: [Ir(tppr)$_2$(pFac)])

First, 25 mL of 2-ethoxyethanol, 0.45 g of [Ir(tppr)$_2$Cl]$_2$, which is the binuclear complex obtained in above-described Step 2 in Synthesis Example 1, 0.14 mL of pivaloyltrifluoroacetone, and 0.29 g of sodium carbonate were put in an eggplant flask with a reflux pipe, and the air in the flack was replaced with argon. Then, irradiation with microwave (2.45 GHz, 100 W) for 20 minutes was performed to cause a reaction. Dichloromethane was added to the reacted solution and was filtered. The obtained filtrate was concentrated to precipitate orange powder. The powder was filtered and washed with ethanol, and then, ether to give [Ir(tppr)$_2$ (pFac)], which is an organometallic complex of the present invention (76% yield). The synthetic scheme of this step is represented by (c-2) below.

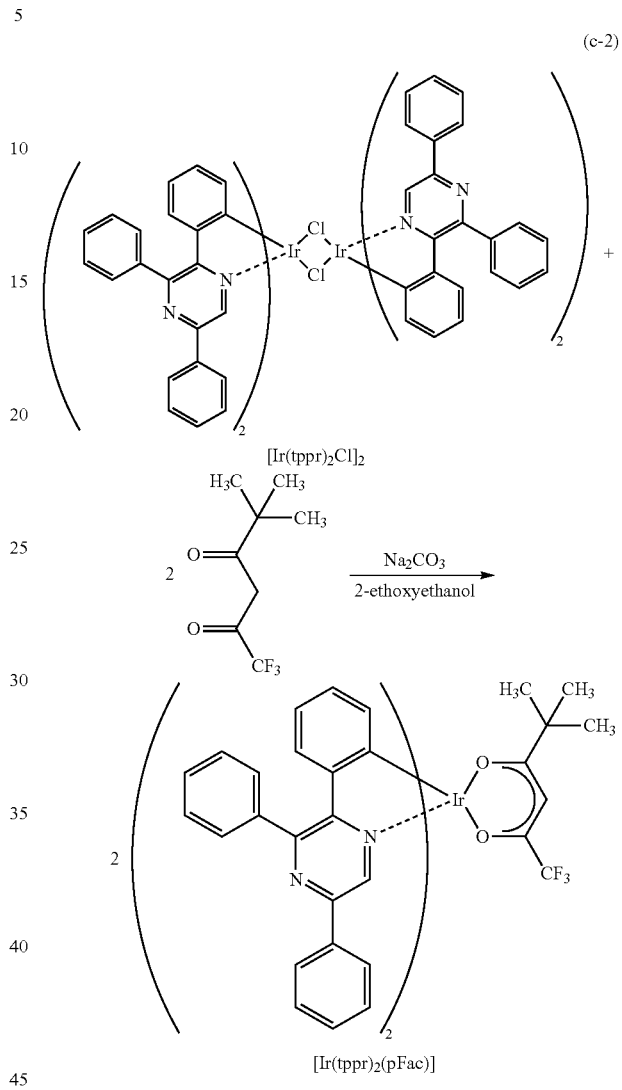

(c-2)

Figure 15:
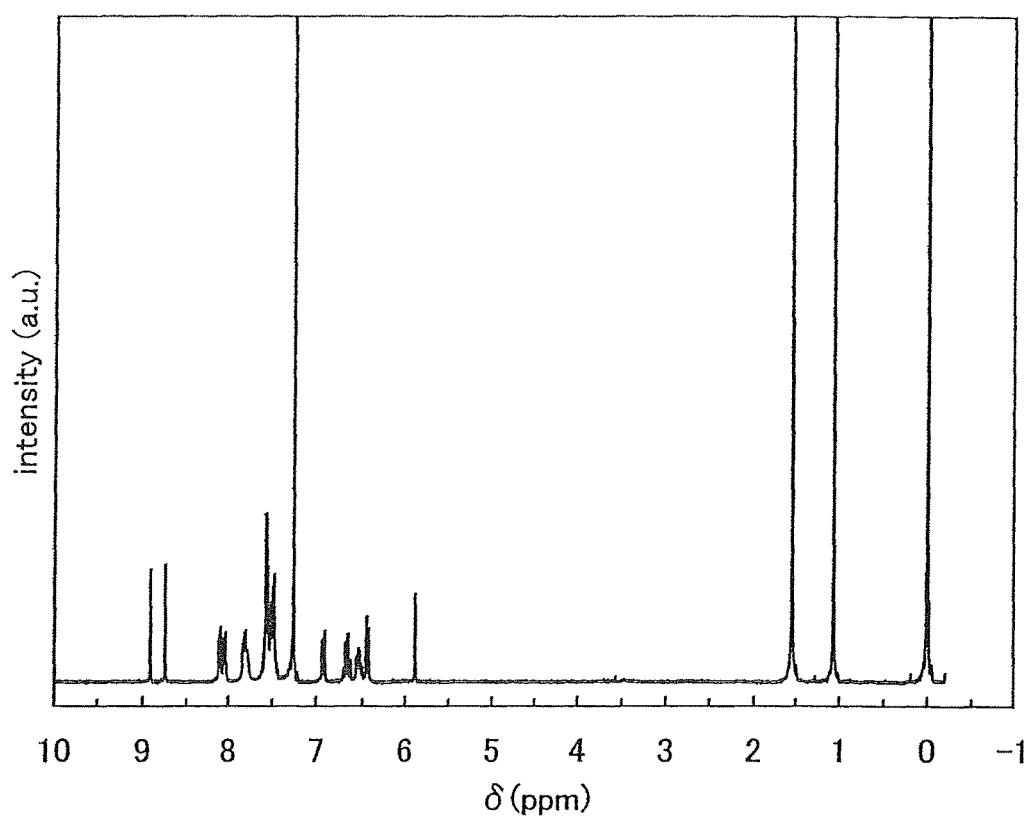
FIG. 15 illustrates the $^1$H NMR spectrum of bis(2,3,5-triphenylpyrazinato)(pivaloyltrifluoroacetonato)iridium(III) (abbr.: [Ir(tppr)$_2$(pFac)])

An analysis result of the orange powder obtained in the above-described step by nuclear magnetic resonance spectrometry ($^1$H-NMR) is shown below and the $^1$H NMR spectrum is shown in FIG. 15. The analysis result reveals that [Ir(tppr)$_2$(pFac)], which is an organometallic complex of the present invention which is represented by the foregoing structural formula (148), was obtained in this Synthesis Example 2.

$^1$H-NMR.δ (CDCl$_3$): 1.06 (s, 9H), 5.88 (s, 1H), 6.45 (d, 2H), 6.54 (dt, 2H), 6.67 (m, 2H), 6.92 (d, 2H), 7.48-7.57 (m, 12H), 7.82 (m, 4H), 8.08 (ddd, 4H), 8.75 (s, 1H), 8.92 (s, 1H).

The absorption spectrum of [Ir(tppr)$_2$(pFac)] was measured with an ultraviolet-visible spectrophotometer (V-550, manufactured by JASCO Corporation), using a dichloromethane solution (0.090 mmol/L) at room temperature. Further, the emission spectrum of [Ir(tppr)$_2$(pFac)] was measured with a fluorescence spectrophotometer (FS920, manufactured by Hamamatsu Photonics K.K.), using a degassed dichloromethane solution (0.31 mmol/L) at room temperature. The measurement result is shown in FIG. 16 in which the horizontal axis indicates a wavelength and the vertical axes indicate a molar absorption coefficient and an emission intensity.

Figure 16:
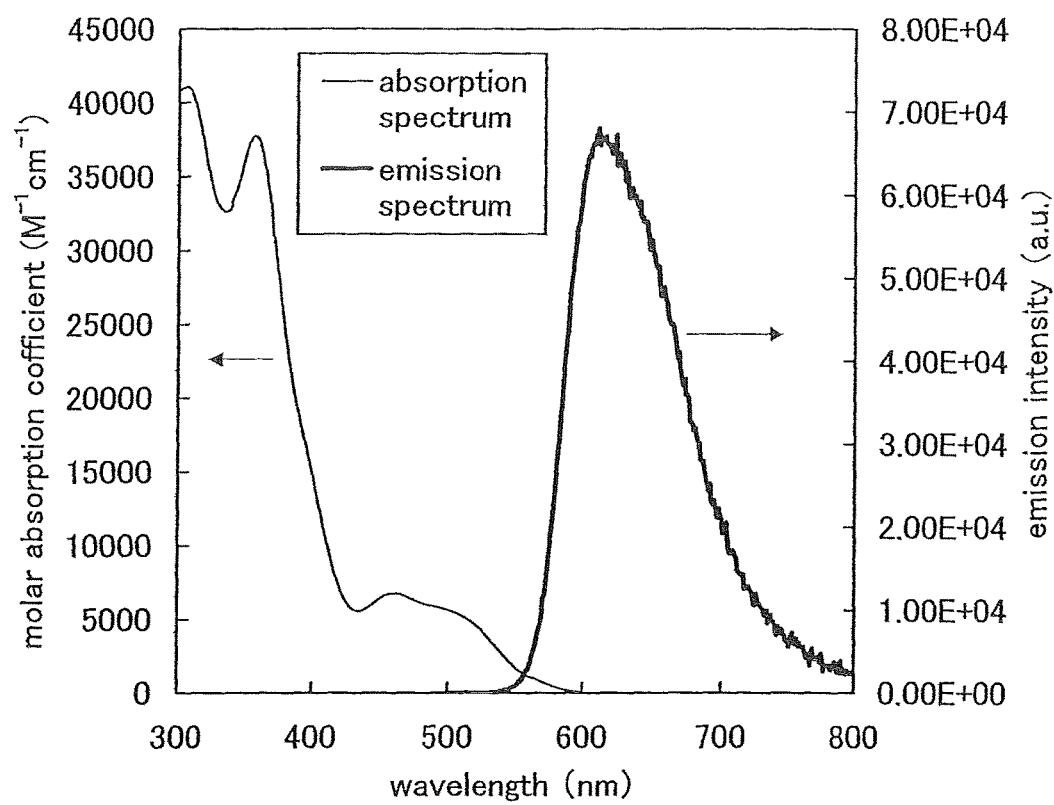
FIG. 16 illustrates the absorption spectrum and the emission spectrum of bis(2,3,5-triphenylpyrazinato)(pivaloyltrifluoroacetonato)iridium(III) (abbr.: [Ir(tppr)$_2$(pFac)]).

As is shown in FIG. 16, an organometallic complex of the present invention [Ir(tppr)$_2$(pFac)] has a light emission peak at 610 nm and orange light was observed from the solution.

Example 5

In this Example, the solubility of an organometallic complex including a pyrazine skeleton described in Embodiment Mode 1 was measured. The measurement was performed by examining the solubility in various solvents: dioxane, which is ether; chloroform and dimethylformamide (DMF), which are an organic solvent not including an aromatic ring; and toluene, which is an aromatic hydrocarbon-based solvent.

Among the complexes disclosed in Embodiment Mode 1, [Ir(tppr)$_2$(pFac)] represented by the structural formula (148), which is synthesized in Example 4, was selected as a measurement object. The solubility was investigated.

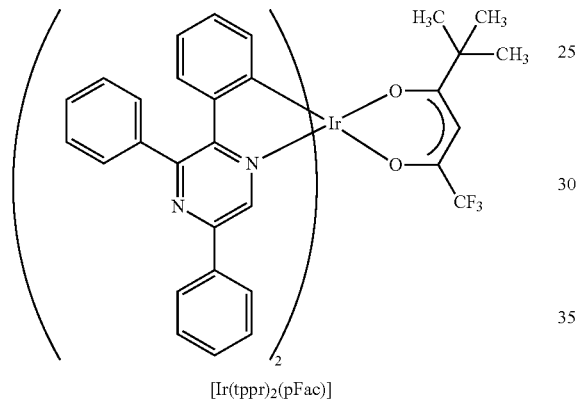

[Ir(tppr)$_2$(pFac)]

The solubility test results of the sample are shown in Table 2 below. In Table 2, a cross indicates that the solubility x (g/L) is x<0.6, a triangle indicates that 0.9>x≥0.6, a circle indicates that 1.2>x≥0.9, and a double circle indicates that x≥1.2.

TABLE 2

| Structural formula No. | Compound abbreviation | Ethers dioxane | Solvents not having aromatic ring | | Solvents having aromatic ring toluene |
|---|---|---|---|---|---|
| | | | chloroform | DMF | |
| (148) | Ir(tppr)$_2$(pFac) | ◎ | ◎ | ◎ | ◎ | solubility x (g/L)
x ≥ 1.2 ◎
1.2 > x ≥ 0.9 ○
0.9 > x ≥ 0.6 △
x < 0.6 X

[Ir(tppr)$_2$(pFac)] represented by the structural formula (148), which is synthesized in Example 4 has high solubility, and therefore, is preferably used for a composition for coating which is used for a light emitting element manufactured a wet process.

In specific, it is found that [Ir(tppr)$_2$(pFac)] represented by the structural formula (148) also has extremely high solubility (equal to or greater than 1.2 g/L) in dioxane, which is ether. In addition, it is found that [Ir(tppr)$_2$(pFac)] also has extremely high solubility (equal to or greater than 1.2 g/L) in chloroform and dimethylformamide (DMF), which are an organic solvent not including an aromatic ring. In addition, [Ir(tppr)$_2$(pFac)] also has extremely high solubility (equal to or greater than 1.2 g/L) in toluene, which is an aromatic hydrocarbon-based solvent. Accordingly, since [Ir(tppr)$_2$(pFac)] represented by the structural formula (148) has solubility in many kinds of solvents, [Ir(tppr)$_2$(pFac)] is preferably used for a composition for coating.

As described above, the inventors of the present invention have found that solubility becomes higher when a ligand represented by the general formula (L1) is introduced.

This application is based on Japanese Patent Application serial no. 2007-133341 filed with Japan Patent Office on May 18, 2007, the entire contents of which are hereby incorporated by reference.

What is claimed is:

1. A light emitting element comprising:
   a pair of electrodes, and
   a first light emitting layer and a second light emitting layer between the pair of electrodes;
   wherein at least one of the first light emitting layer and the second light emitting layer comprise an organometallic complex,
   wherein the organometallic complex is represented by a general formula (G1):

(G1)

wherein, Ar represents an arylene group;
   R$^1$ represents an alkyl group or an aryl group;
   R$^2$ represents an aryl group;
   R$^3$ represents hydrogen or an alkyl group;
   M is a central metal and represents either an element belonging to Group 9 or an element belonging to Group 10;
   n is 2 when the M is an element belonging to Group 9, and n is 1 when the M is an element belonging to Group 10; and
   one of R$^{21}$ and R$^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

2. The light emitting element according to claim 1, wherein an emission color of the first light emitting layer and an emission color of the second light emitting layer are complementary colors.

3. The light emitting element according to claim 1, wherein a charge generation layer is provided between the first light emitting layer and the second light emitting layer.

4. The light emitting element according to claim 1, wherein at least one of the first light emitting layer and the second light emitting layer comprises a polymer.

5. The light emitting element according to claim 1,
wherein at least one of the first light emitting layer and the second light emitting layer further comprises an organic semiconductor material.

6. A light emitting device comprising the light emitting element according to claim 1.

7. An electric apparatus comprising the light emitting element according to claim 1.

8. A lighting device comprising the light emitting element according to claim 1.

9. A light emitting element comprising:
a pair of electrodes; and
a first light emitting layer and a second light emitting layer between the pair of electrodes;
wherein at least one of the first light emitting layer and the second light emitting layer comprise an organometallic complex,
wherein the organometallic complex is represented by a general formula (G2):

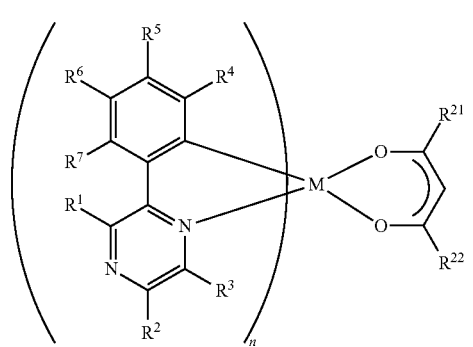

(G2)

wherein, $R^1$ represents any one of an alkyl group, a phenyl group, or a phenyl group having a substituent;
$R^2$ represents a phenyl group or a phenyl group having a substituent;
$R^3$ represents hydrogen or an alkyl group;
each of $R^4$ to $R^7$ represents any one of hydrogen, an alkyl group, a halogen group, a haloalkyl group, an alkoxy group, or an alkoxycarbonyl group;
M is a central metal and represents either an element belonging to Group 9 or an element belonging to Group 10;
n is 2 when the M is an element belonging to Group 9, and n is 1 when the M is an element belonging to Group 10; and
one of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

10. The light emitting element according to claim 9,
wherein an emission color of the first light emitting layer and an emission color of the second light emitting layer are complementary colors.

11. The light emitting element according to claim 9,
wherein a charge generation layer is provided between the first light emitting layer and the second light emitting layer.

12. The light emitting element according to claim 9,
wherein at least one of the first light emitting layer and the second light emitting layer comprises a polymer.

13. The light emitting element according to claim 9,
wherein at least one of the first light emitting layer and the second light emitting layer further comprises an organic semiconductor material.

14. A light emitting device comprising the light emitting element according to claim 9.

15. An electric apparatus comprising the light emitting element according to claim 9.

16. A lighting device comprising the light emitting element according to claim 9.

17. A light emitting element comprising:
a pair of electrodes; and
a first light emitting layer and a second light emitting layer between the pair of electrodes;
wherein at least one of the first light emitting layer and the second light emitting layer comprise an organometallic complex,
wherein the organometallic complex is represented by a general formula (G3):

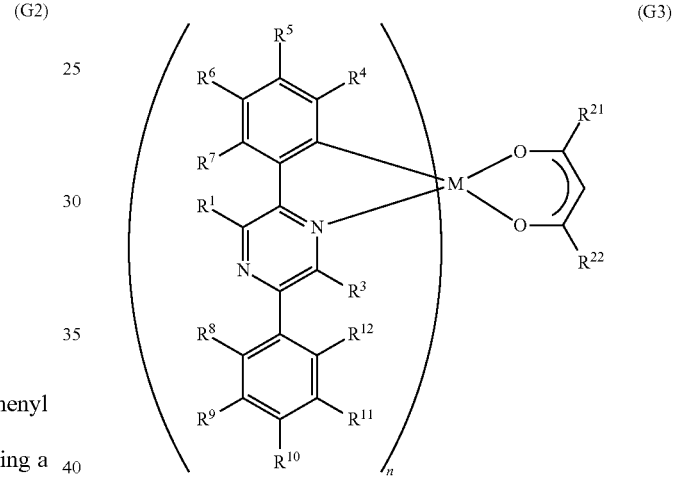

(G3)

wherein, $R^1$ represents any one of an alkyl group, a phenyl group, or a phenyl group having a substituent;
$R^3$ represents hydrogen or an alkyl group;
each of $R^4$ to $R^{12}$ represents any one of hydrogen, an alkyl group, a halogen group, a haloalkyl group, an alkoxy group, or an alkoxycarbonyl group;
M is a central metal and represents either an element belonging to Group 9 or an element belonging to Group 10;
n is 2 when the M is an element belonging to Group 9, and n is 1 when the M is an element belonging to Group 10; and
one of $R^{21}$ and $R^{22}$ represents an alkyl group having 2 to 10 carbon atoms or a haloalkyl group having 2 to 10 carbon atoms and the other one represents an alkyl group having 1 to 10 carbon atoms or a haloalkyl group having 1 to 10 carbon atoms.

18. The light emitting element according to claim 17,
wherein an emission color of the first light emitting layer and an emission color of the second light emitting layer are complementary colors.

19. The light emitting element according to claim 17,
wherein a charge generation layer is provided between the first light emitting layer and the second light emitting layer.

20. The light emitting element according to claim 17, wherein at least one of the first light emitting layer and the second light emitting layer comprises a polymer.

21. The light emitting element according to claim 17, wherein at least one of the first light emitting layer and the second light emitting layer further comprises an organic semiconductor material.

22. A light emitting device comprising the light emitting element according to claim 17.

23. An electric apparatus comprising the light emitting element according to claim 17.

24. A lighting device comprising the light emitting element according to claim 17.

* * * * *